(12) United States Patent
Lee-Sepsick

(10) Patent No.: US 11,744,729 B2
(45) Date of Patent: Sep. 5, 2023

(54) METHODS AND DEVICES FOR CONTROLLED DELIVERY

(71) Applicant: FEMASYS INC., Suwanee, GA (US)

(72) Inventor: Kathy Lee-Sepsick, Suwanee, GA (US)

(73) Assignee: FEMASYS INC., Suwanee, GA (US)

( * ) Notice: Subject to any disclaimer, the term of this patent is extended or adjusted under 35 U.S.C. 154(b) by 1066 days.

(21) Appl. No.: 16/402,193

(22) Filed: May 2, 2019

(65) Prior Publication Data

US 2019/0336325 A1  Nov. 7, 2019

Related U.S. Application Data

(60) Provisional application No. 62/665,725, filed on May 2, 2018.

(51) Int. Cl.

| | |
|---|---|
| *A61F 6/22* | (2006.01) |
| *A61L 24/06* | (2006.01) |
| *A61L 24/00* | (2006.01) |
| *A61M 25/01* | (2006.01) |
| *A61M 25/10* | (2013.01) |
| *A61M 25/00* | (2006.01) |
| *A61B 17/12* | (2006.01) |
| *A61F 6/18* | (2006.01) |
| *A61F 6/20* | (2006.01) |

(52) U.S. Cl.
CPC ............ *A61F 6/22* (2013.01); *A61B 17/1204* (2013.01); *A61F 6/18* (2013.01); *A61F 6/20* (2013.01); *A61L 24/0015* (2013.01); *A61L 24/0042* (2013.01); *A61L 24/06* (2013.01); *A61M 25/0074* (2013.01); *A61M 25/0136* (2013.01); *A61M 25/10* (2013.01); *A61L 2400/06* (2013.01); *A61M 2210/1425* (2013.01); *A61M 2210/1433* (2013.01)

(58) Field of Classification Search
CPC ..... A61F 6/22; A61F 6/18; A61F 6/20; A61B 17/1204; A61M 25/0074; A61M 25/0136; A61M 25/10; A61M 2210/1425; A61M 2210/1433
See application file for complete search history.

(56) References Cited

U.S. PATENT DOCUMENTS

| | | | |
|---|---|---|---|
| 3,875,939 | A | 4/1975 | Bolduc et al. |
| 3,972,331 | A * | 8/1976 | Bolduc ............ A61M 25/10181 604/196 |
| 4,611,602 | A | 9/1986 | Bolduc |
| 6,749,617 | B1 | 6/2004 | Palasis et al. |
| 7,695,467 | B2 | 4/2010 | Breznock et al. |
| 2009/0024108 | A1* | 1/2009 | Lee-Sepsick ......... A61P 15/00 424/9.1 |
| 2009/0024155 | A1 | 1/2009 | Lee-Sepsick et al. |
| 2009/0277455 | A1* | 11/2009 | Lee-Sepsick .... A61B 17/12186 128/831 |
| 2010/0049192 | A1* | 2/2010 | Holtz ................ A61N 1/36071 606/41 |
| 2013/0035664 | A1* | 2/2013 | Mojdehbakhsh . A61M 5/31596 604/506 |
| 2014/0024934 | A1 | 1/2014 | Lee-Sepsick |
| 2014/0163610 | A1 | 6/2014 | Zhang |
| 2018/0070985 | A1* | 3/2018 | Lee-Sepsick .... A61B 17/12186 |

FOREIGN PATENT DOCUMENTS

| | | |
|---|---|---|
| CA | 2817330 | 5/2012 |
| WO | PCT/US2019/030491 | 11/2019 |

OTHER PUBLICATIONS

International IPRP, issued Nov. 3, 2020, for PCT/US2019/030491, Applicant Femasys, Inc., 8 p.
Partial European supplementary search, dated Feb. 2, 2022, for EP1975794.7, Applicant Femasys, Inc., 10 p.
Extended European search report, dated May 4, 2022, for EP1975794.7, Applicant Femasys, Inc., 10 p.
FER, issued Jun. 9, 2022, for IN 202017052349, Applicant Femasys, Inc., 6 p.
PCT/US2019/030491, PCT, May 2, 2019, Kathy Lee-Sepsick.
3097934, CA, May 2, 2019, Kathy Lee-Sepsick.
19795794.7, EP, May 2, 2019, Kathy Lee-Sepsick.
202017052349, IN, May 2, 2019, Kathy Lee-Sepsick.
International Search Report, dated Jul. 15, 2019, for PCT/US2019/030491, Applicant Femasys, Inc., 2 p.
International Written Opinion, dated Jul. 15, 2019, for PCT/US2019/030491, Applicant Femasys, Inc., 7 p.

* cited by examiner

*Primary Examiner* — Robert A Wax
*Assistant Examiner* — William Craigo
(74) *Attorney, Agent, or Firm* — Mary Anthony Merchant

(57) ABSTRACT

Disclosed herein are exemplary medical devices for controlled delivery of material compositions, particularly occlusive, therapeutic, or diagnostic compositions.

9 Claims, 29 Drawing Sheets

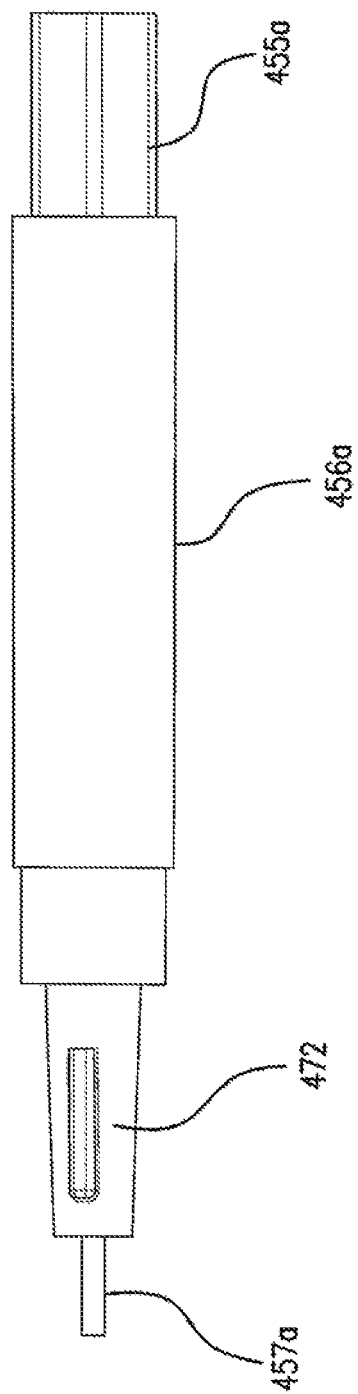

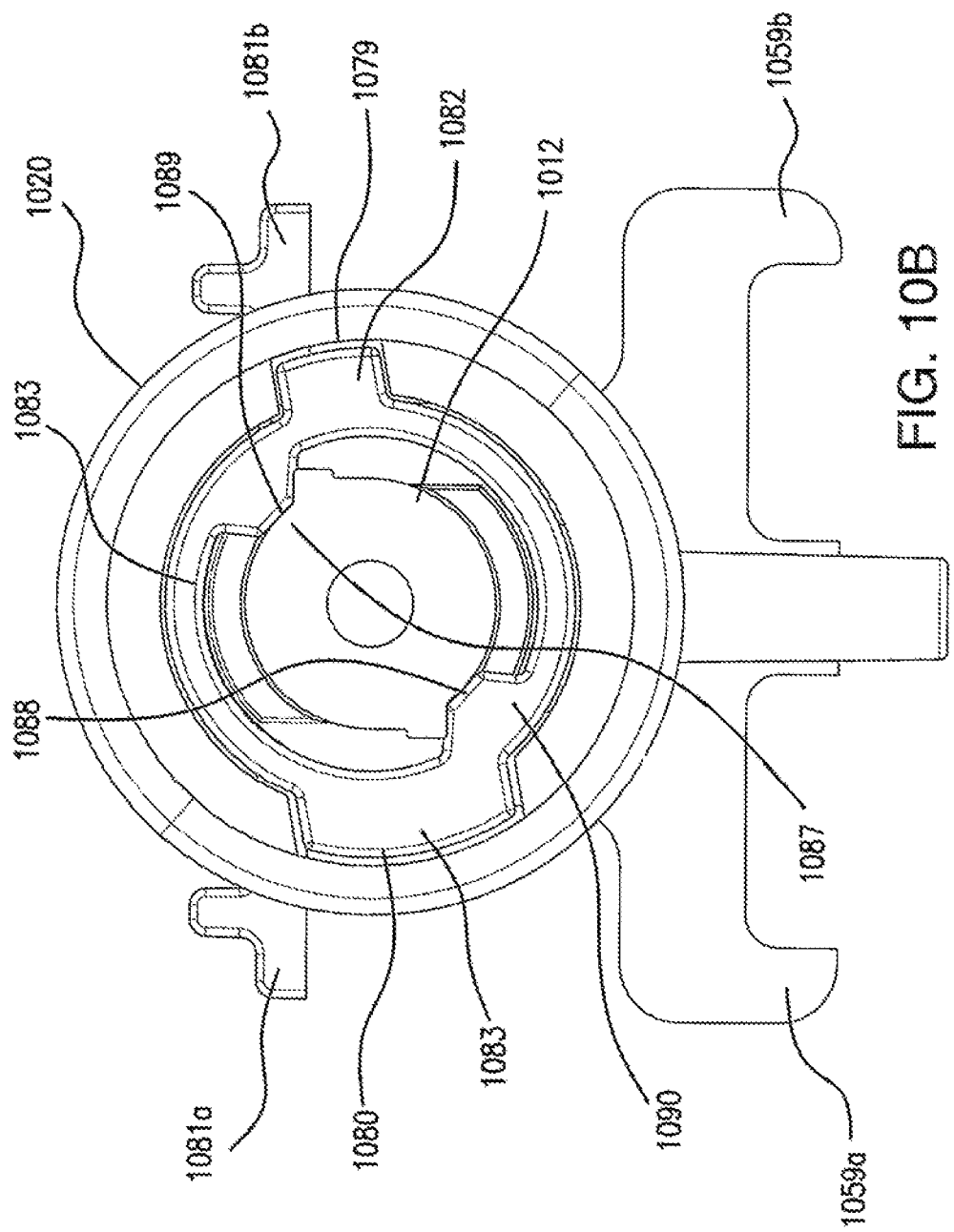

METHODS AND DEVICES FOR CONTROLLED DELIVERY

RELATED APPLICATIONS

Figure 1:
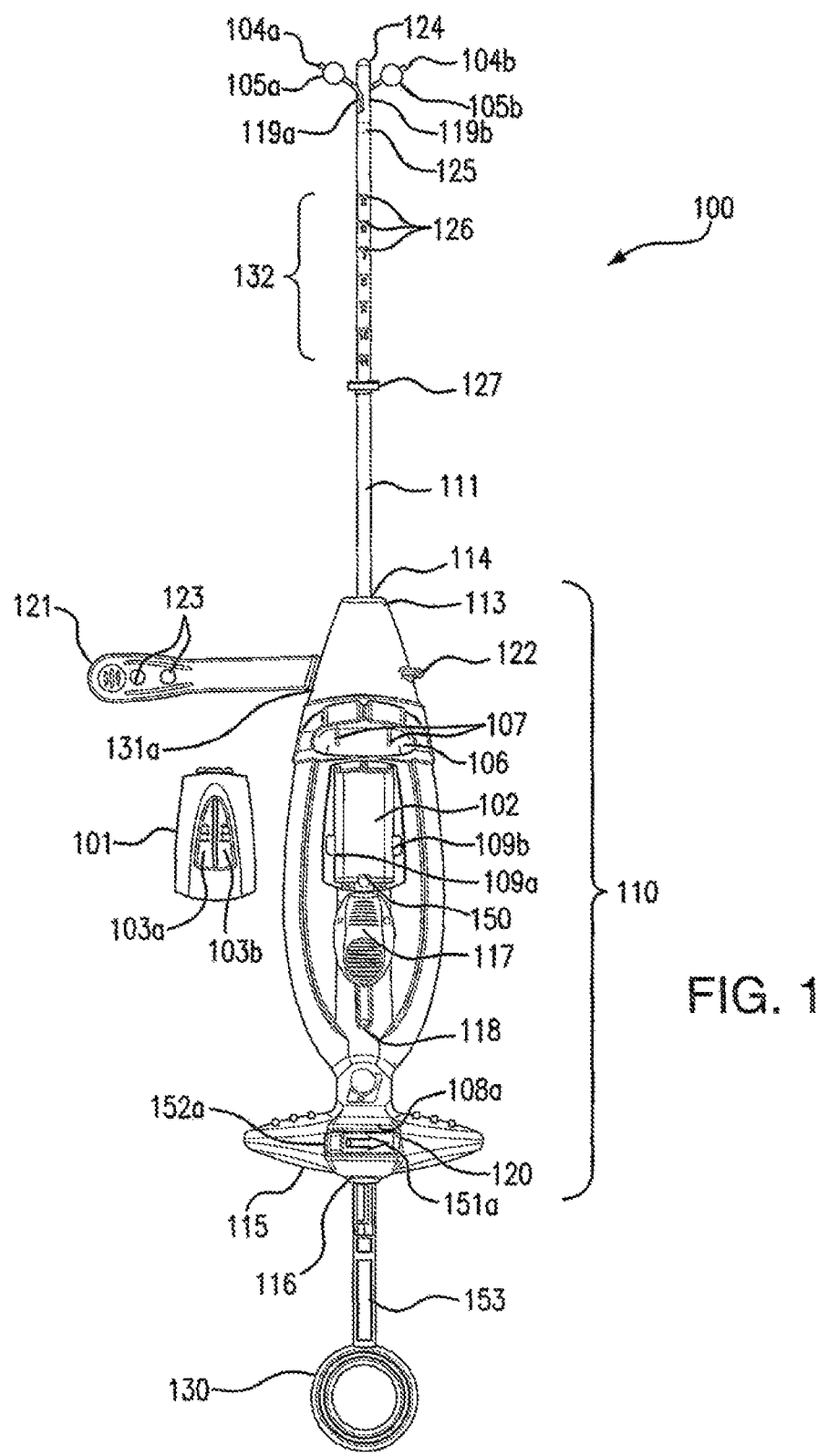

The present disclosure is nonprovisional patent application claiming the priority of and benefit of filing of U.S. Provisional Patent Application Ser. No. 62/665,725, filed 2 May 2018, which is herein incorporated by reference in its entirety.

TECHNICAL FIELD

The present disclosure is directed to devices having specific components that are effective in methods for controlled delivery of compositions to conduits in the body, particularly controlled delivery to one or more mammalian fallopian tubes.

BACKGROUND OF THE INVENTION

Medical devices can be designed in many different ways to achieve the same effect in the body. Medical device design and development is a complex process that is complicated with considerations of regulations, specifications, application requirements, and end user needs. All of these must be taken into account and then adhered to for a successful product. If the device lacks usability, market share will suffer, but if the device doesn't meet regulatory guidelines, it cannot be marketed at all. Much more goes into designing, developing, and introducing a medical device to the market than simply coming up with an innovative idea, building the product, obtaining regulatory approval and selling it to the users.

The idea for new medical devices, like most new product innovations, often stems from the discovery of an unmet market need. For medical devices, the need is for products that can help people better monitor and manage their health, aid providers in improving care delivery, or devices that enable better treatment administration. These needs aren't always obvious to the target user, as common problems are often regarded as inconveniences that must be tolerated.

Additionally, devices that are generally usable may be used by healthcare providers without any particular issues, but design issues may become apparent when consistent or standardized use of a device is intended. Humans bring individualized approaches to use of any tool, and sometimes consistency in use is a preferred approach for a better medical outcome. What is needed are medical devices that are designed to control how the device is used, for example, to control the rate of use and/or the sequencing of actions of the user.

SUMMARY

Disclosed herein are controlled delivery devices and methods for controlled delivery of a material. The present disclosure comprises methods, compositions, systems, and devices for the delivery of compositions for the occlusion of conduits. In particular, the present invention comprises methods, systems, and devices for the occlusion of conduits in humans or other animals. The devices of the present invention are used to deliver compositions comprising materials that occlude the conduit. The occlusive material may be a permanent implant or may be a material that is degraded or resorbed by the body and allows for tissue ingrowth to maintain the occlusion.

One aspect is a method that comprises introduction of a controlled delivery device for delivery of occlusive material to one or both fallopian tubes without the necessity to remove, reinsert, or substantially reposition the delivery device. The implanted occlusive material may be permanent or may be degraded or resorbed by the body and replaced by ingrowth of tissue.

The present disclosure also comprises delivery systems, methods, and devices for the delivery of therapeutic compositions to one or more fallopian tubes to enhance fertility, such as for artificial insemination or ovulation stimulation, to treat tubal disorders, such as ectopic pregnancy, treat infections, such as pelvic inflammatory disease, or treat cancer near, in, around, at the cornua or fimbriae exit of the tube.

FIGURES

FIG. 1 shows a drawing of the top exterior of an exemplary controlled delivery device 100.

Figure 2A:
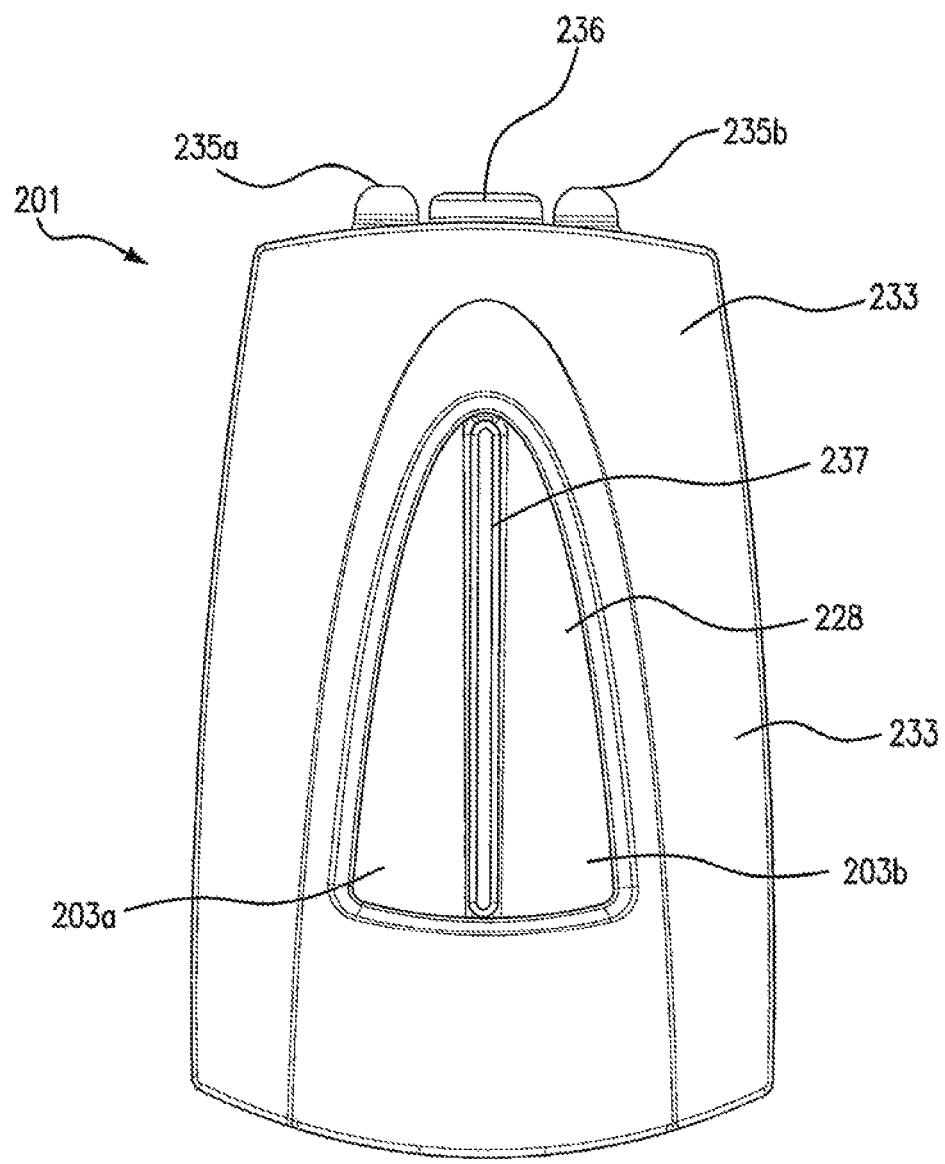
Figure 2B:
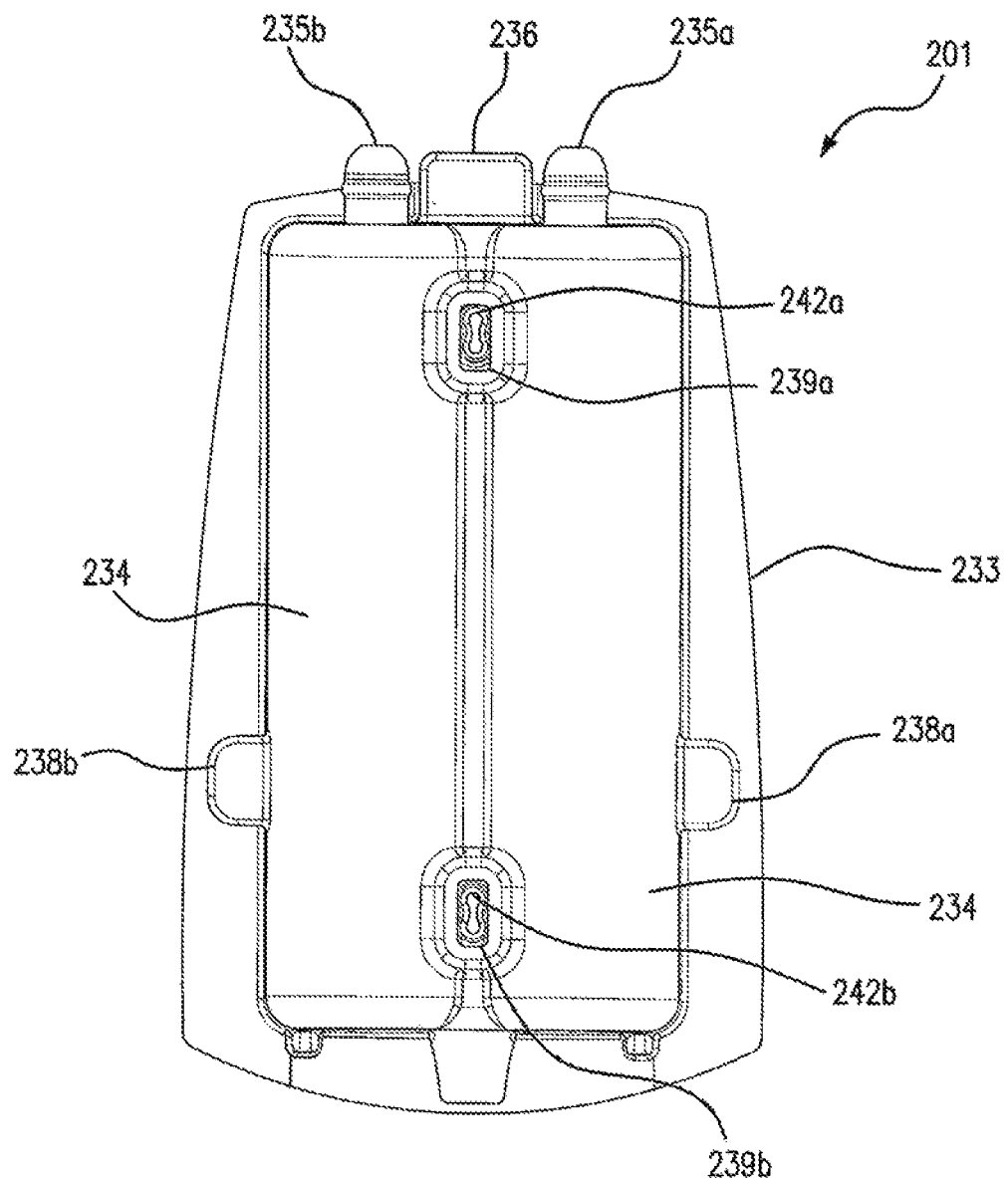
Figure 2C:
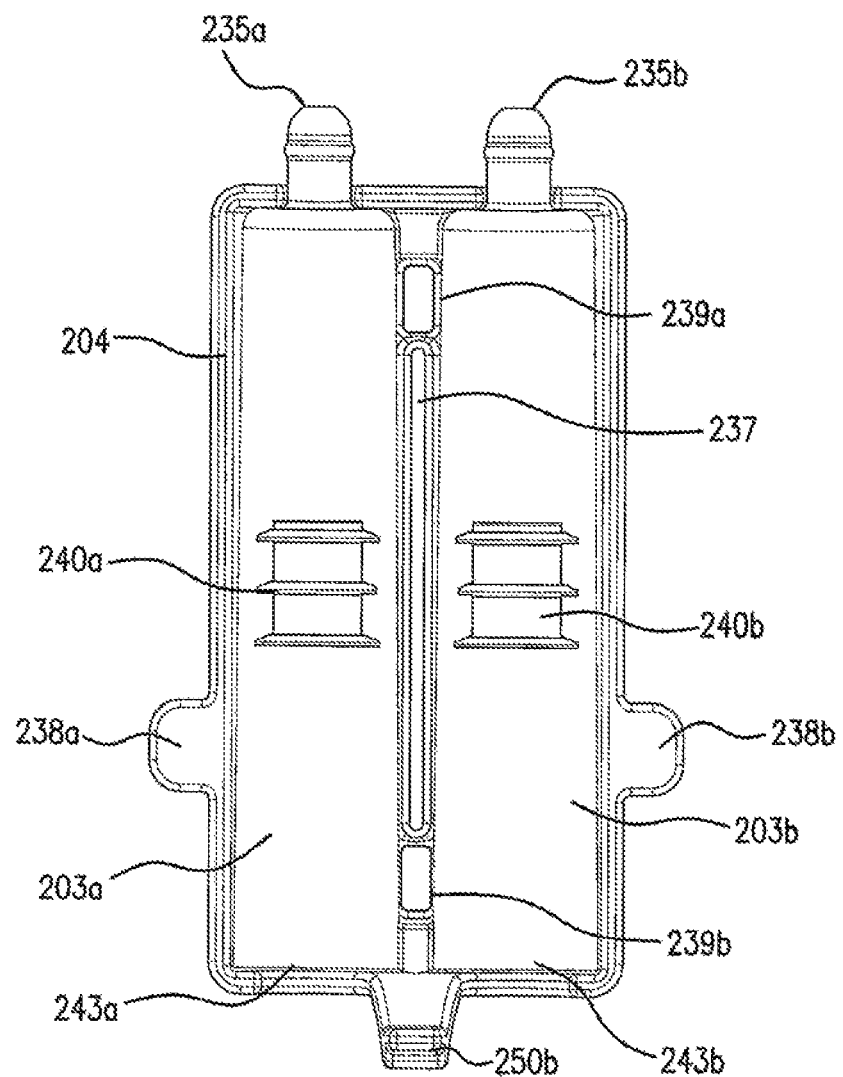
Figure 2D:
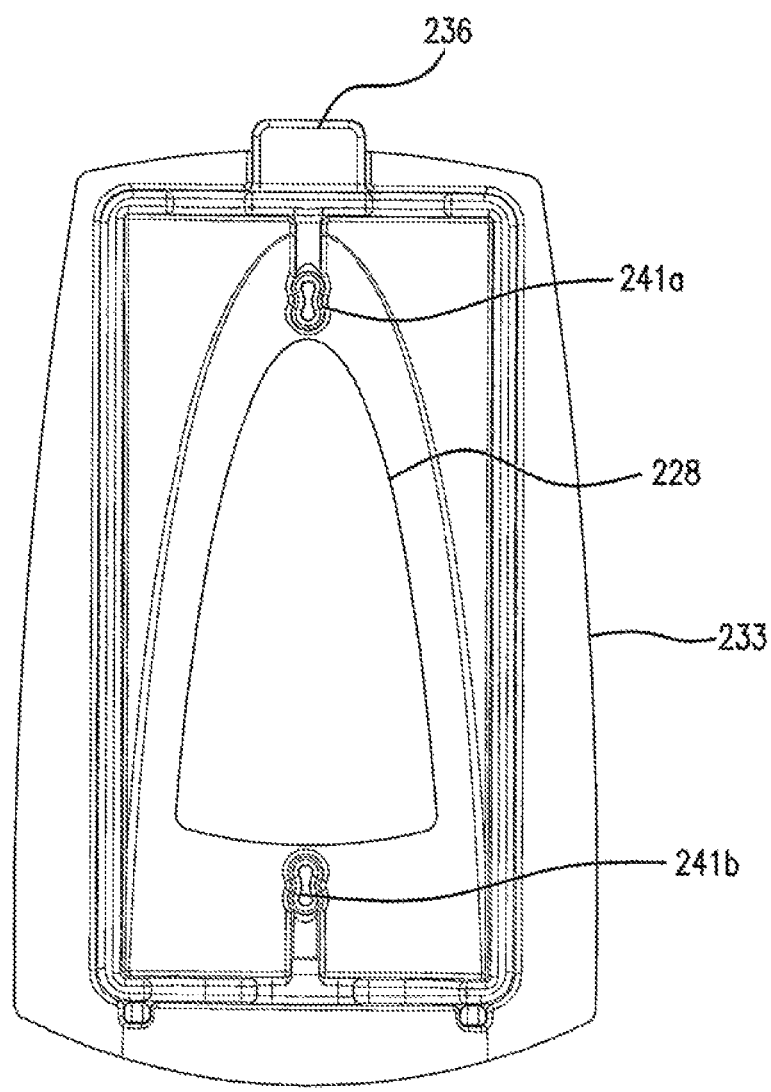
Figure 2E:
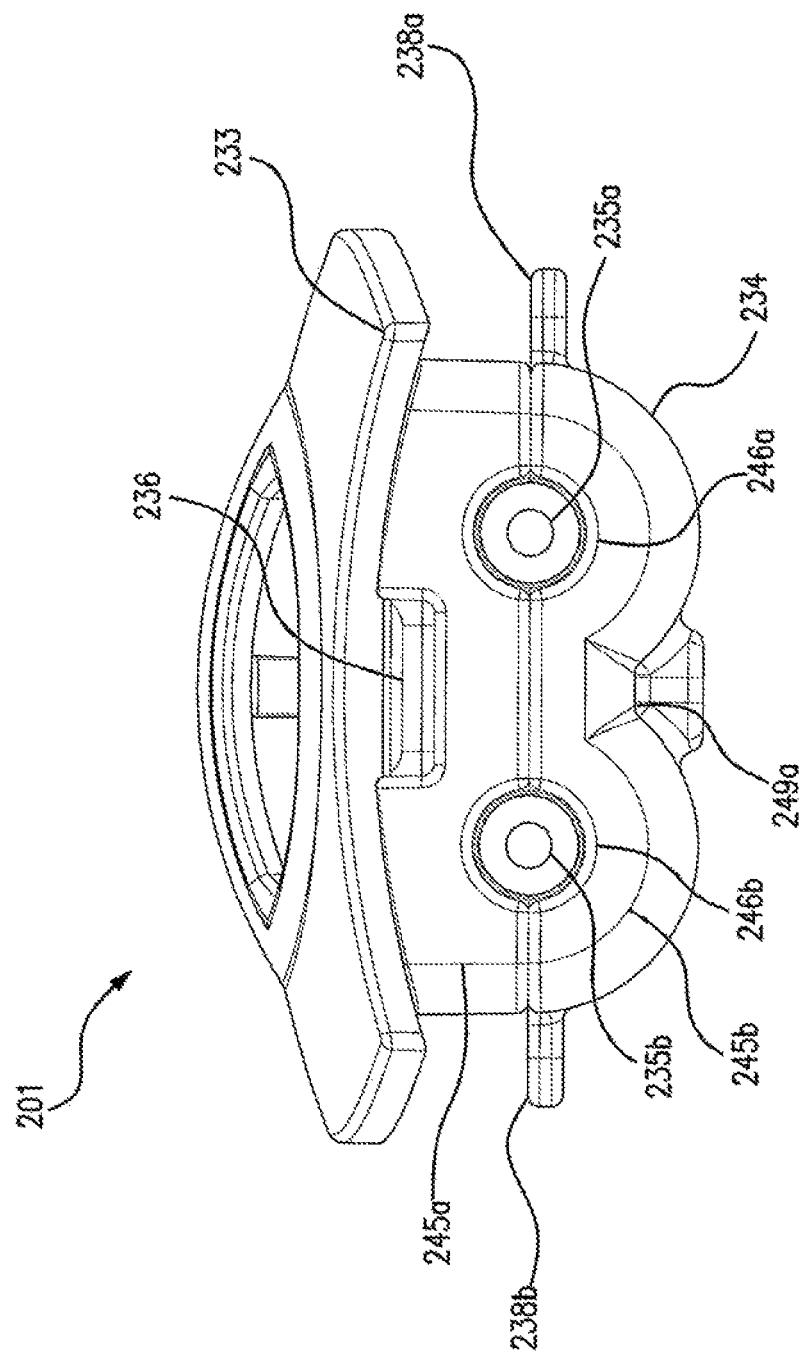
Figure 2F:
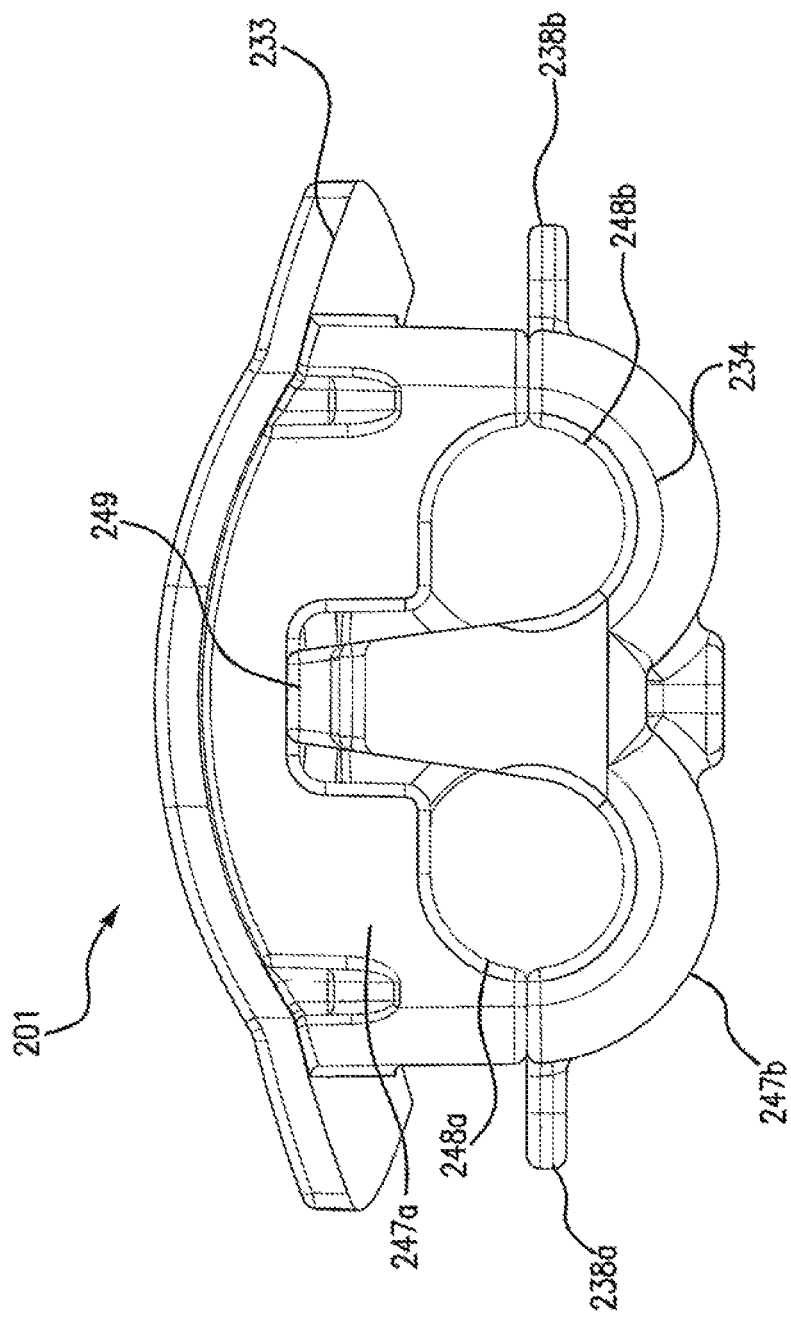

FIGS. 2A-2F show aspects of an exemplary material cartridge and a material container. FIG. 2A shows a top view, FIG. 2B shows a bottom view, FIG. 2C-D shows the top casing removed to show the interior of the material cartridge with 2C showing the interior of top casing and 2D showing the material containers positioned on the interior of the back casing, FIG. 2E shows a front (distal) view, and FIG. 2F shows a back (proximal) view of an exemplary material cartridge.

Figure 3A:
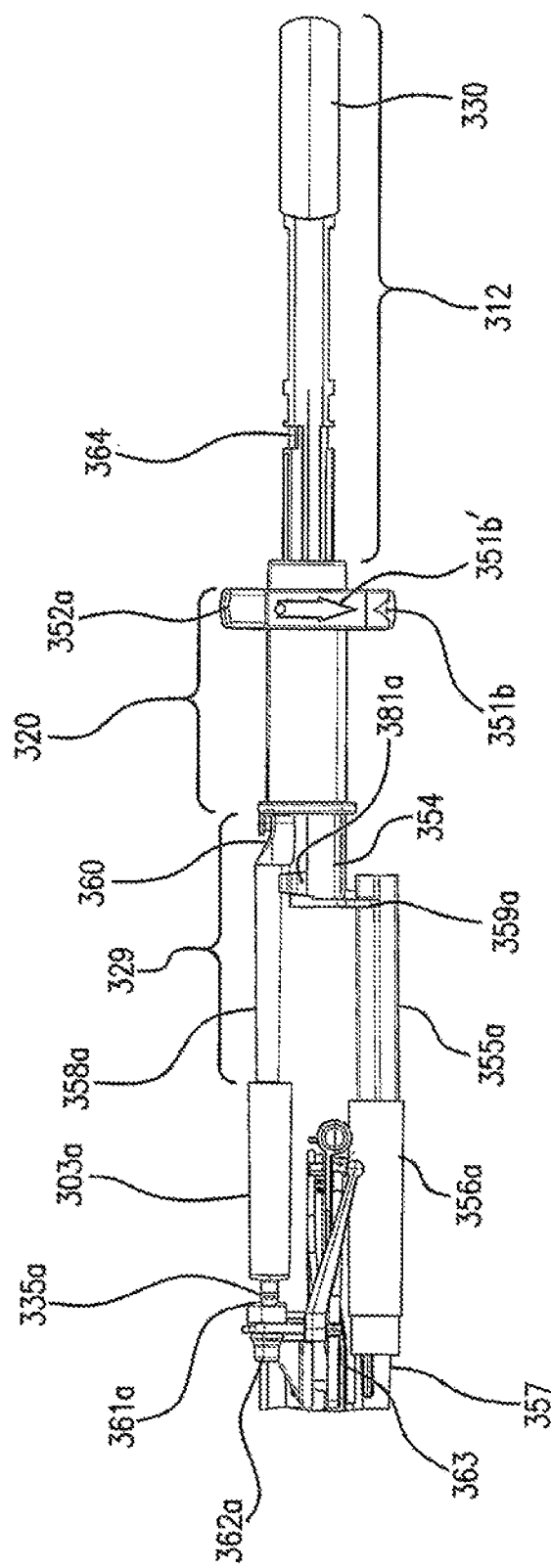
Figure 3B:
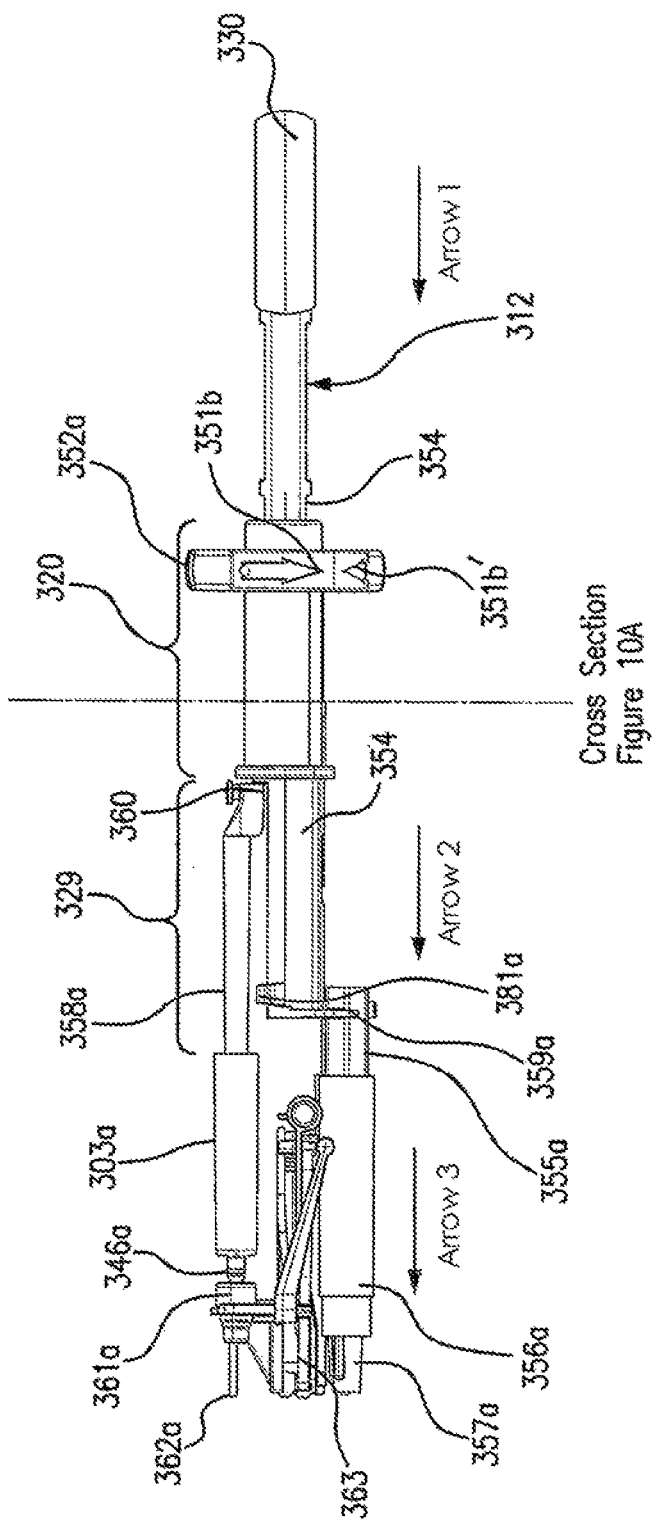
Figure 3C:
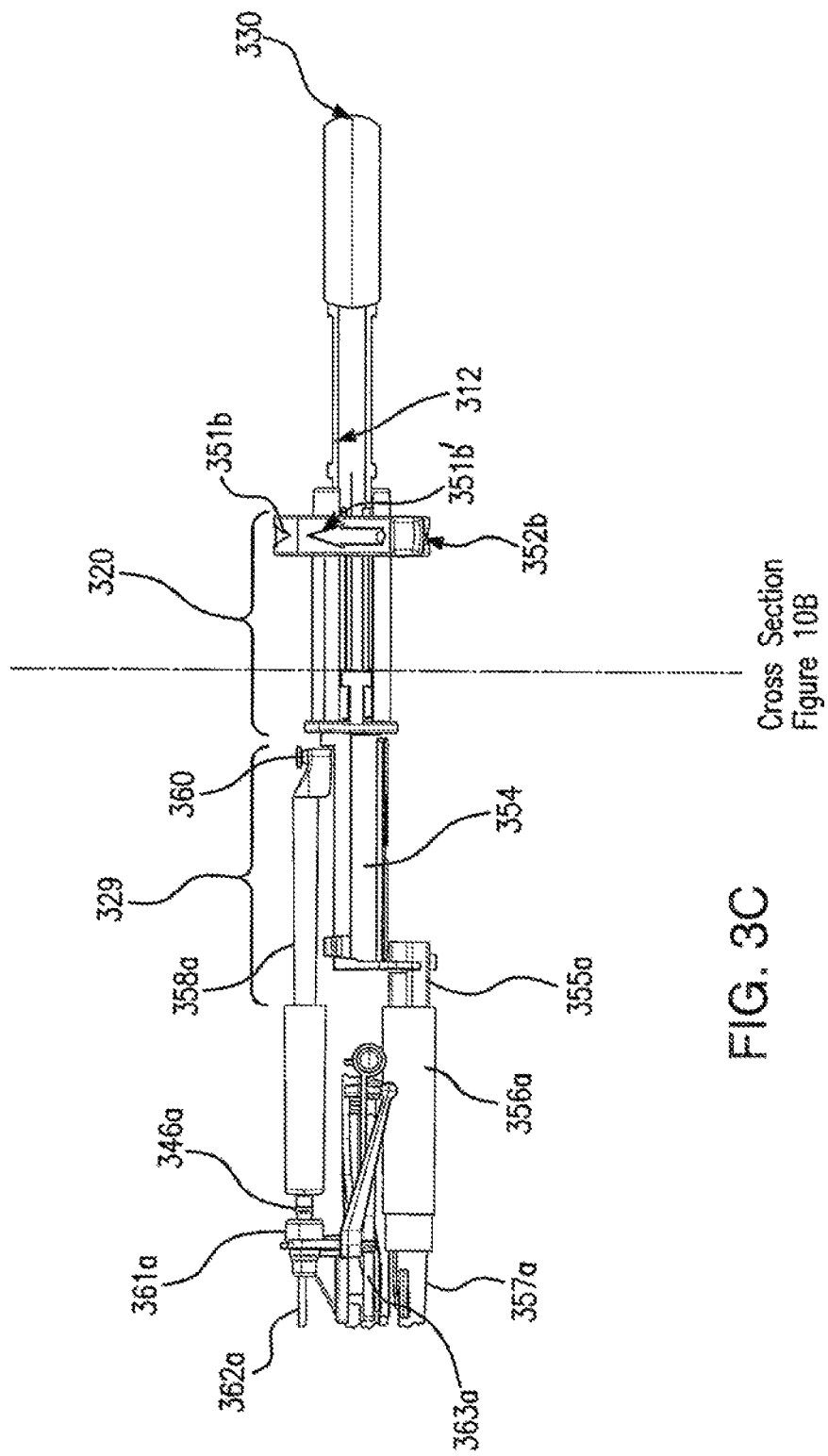
Figure 3D:
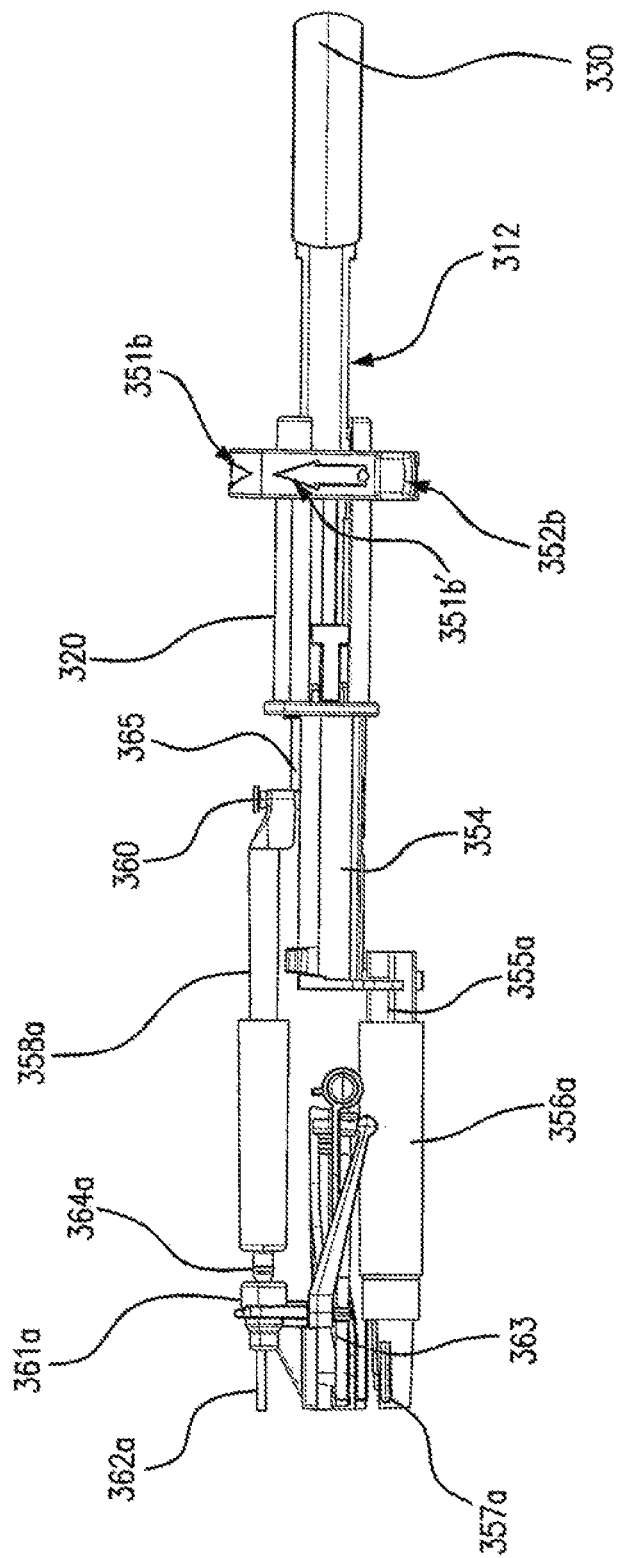
Figure 3E:
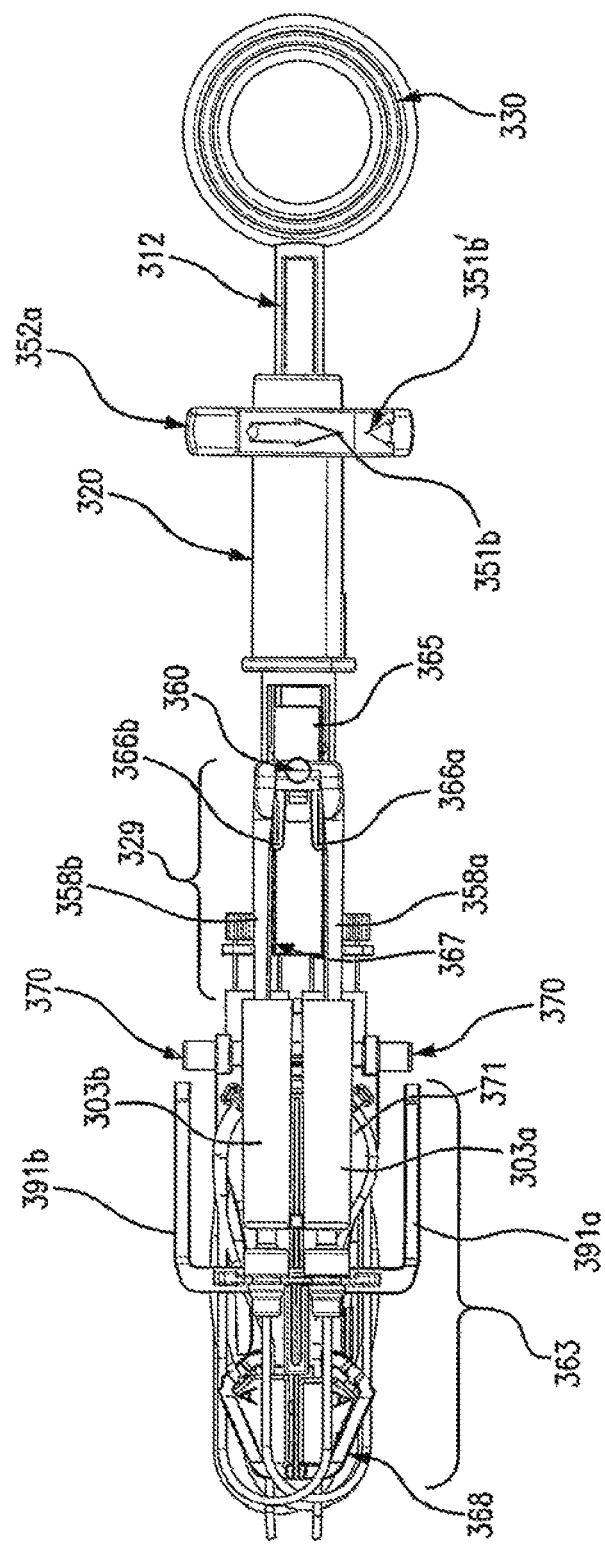
Figure 3F:
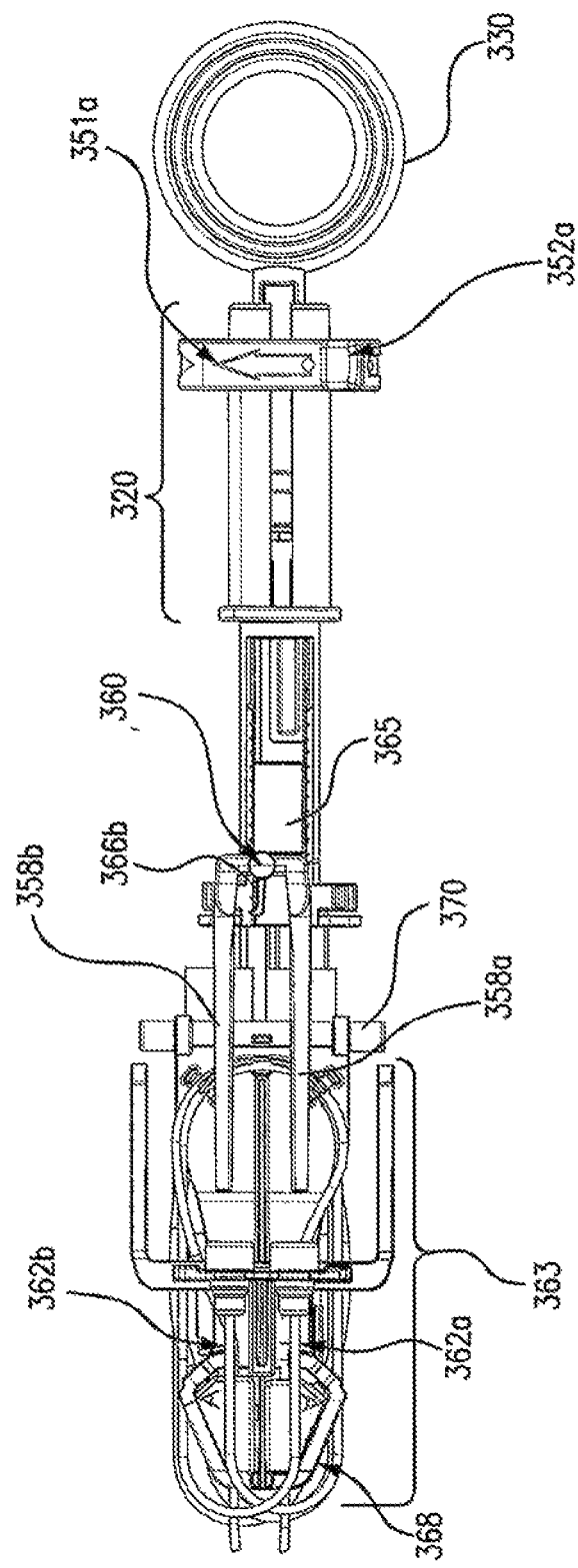
Figure 3G:
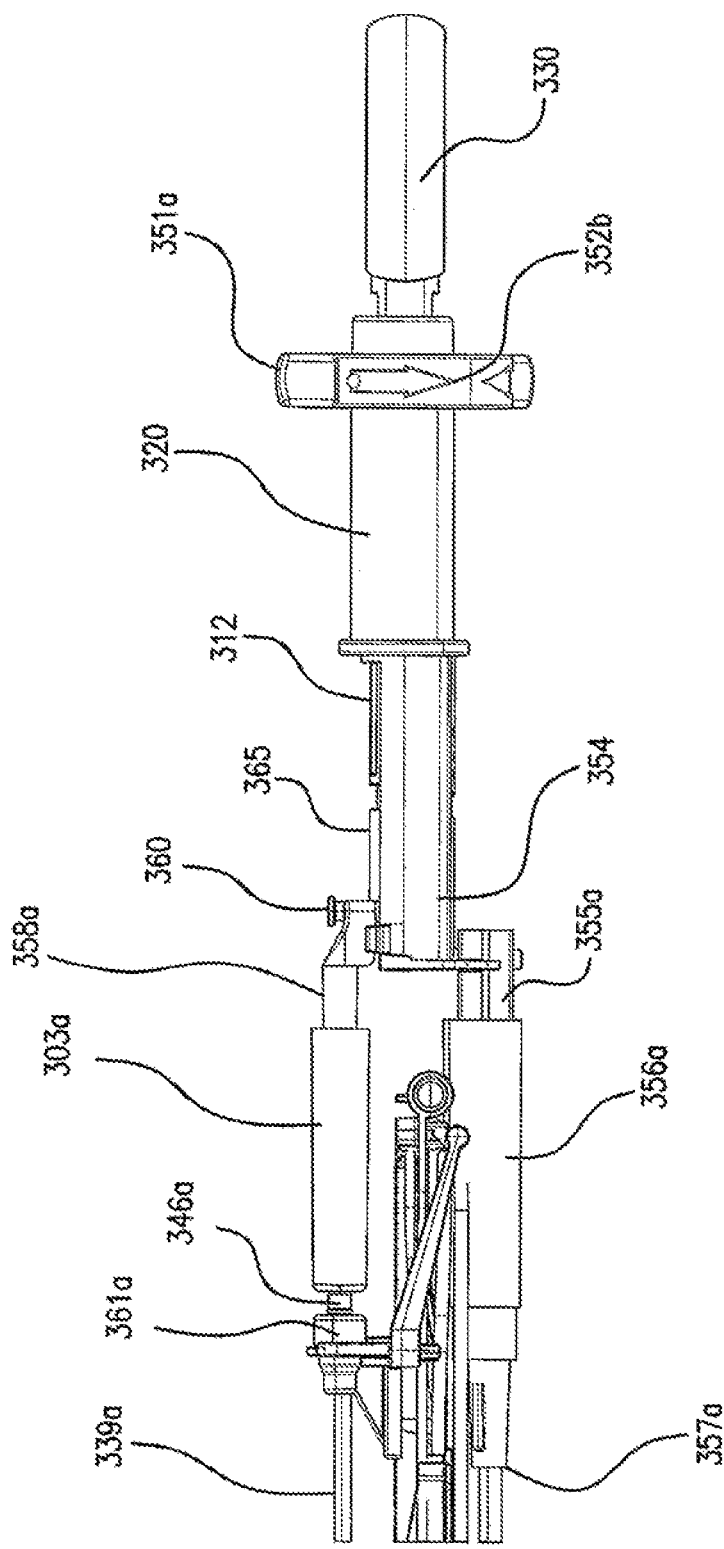

FIGS. 3A-3G show interior elements of exemplary controlled delivery device, 100. FIG. 3A is a side view that shows elements positioned before initial steps leading to filling the double lumen catheter balloons (not shown) wherein the lock is in lock position 1, and system plunger is in system plunger position 1. FIG. 3B is a side view that shows the position of elements at the completion of filling the catheter balloons (not shown), lock in lock position 1, and system plunger in position 2. FIG. 3C is a side view that shows lock rotation to lock position 2, system plunger at position 2, and interior elements. FIG. 3D is a side view that shows advancement of the material plunger arms to system plunger going the system plunger position 3 and the lock is in lock position 2. FIG. 3E shows a top view of the interior elements of exemplary controlled delivery device 100 and the positions of elements after the filling of the catheter balloons with the lock in position 1, system plunger in position 2. FIG. 3F shows a top view of interior elements of an exemplary controlled delivery device 100 and the positions of elements after the movement of the material from the material containers with the lock in position 2, and system plunger in position 3. FIG. 3G is a side view of the interior elements of exemplary controlled delivery device 100 and the positions of elements after the movement of the material from the material containers with the lock returned to position 1, and system plunger is at position 3, but ready for return to position 2.

Figure 4A:
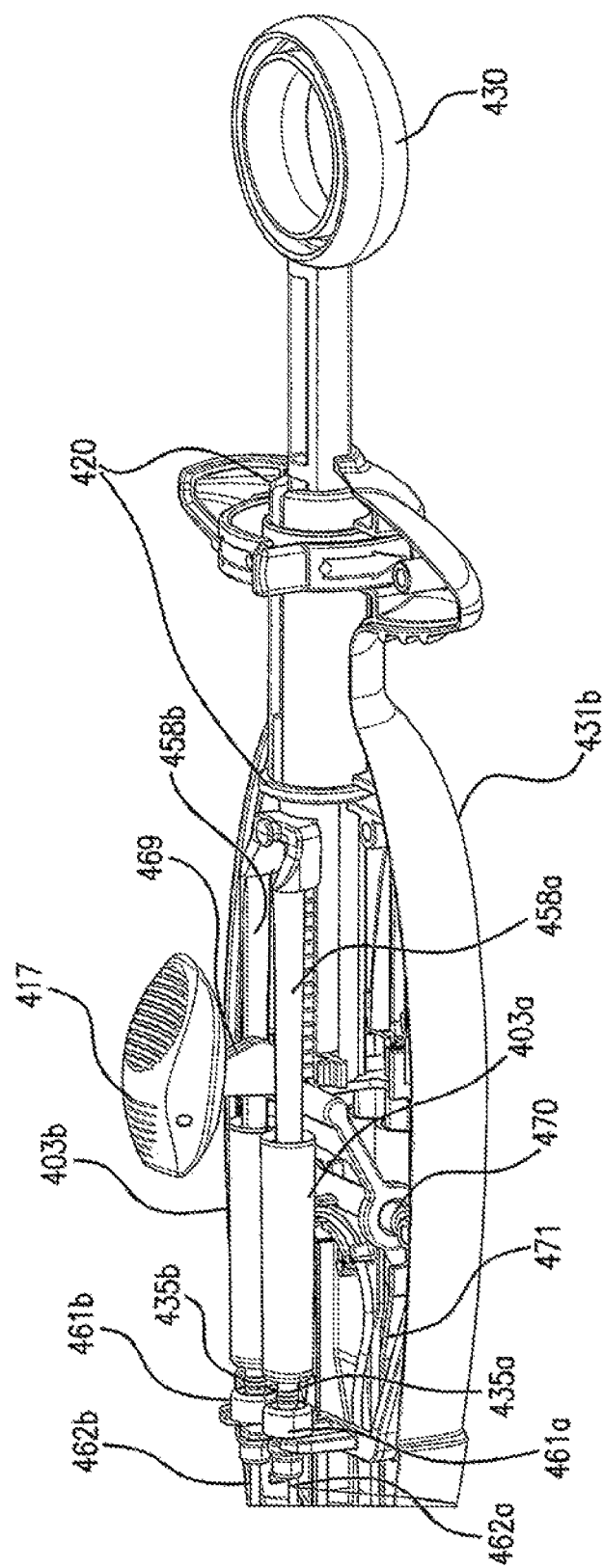
Figure 4B:
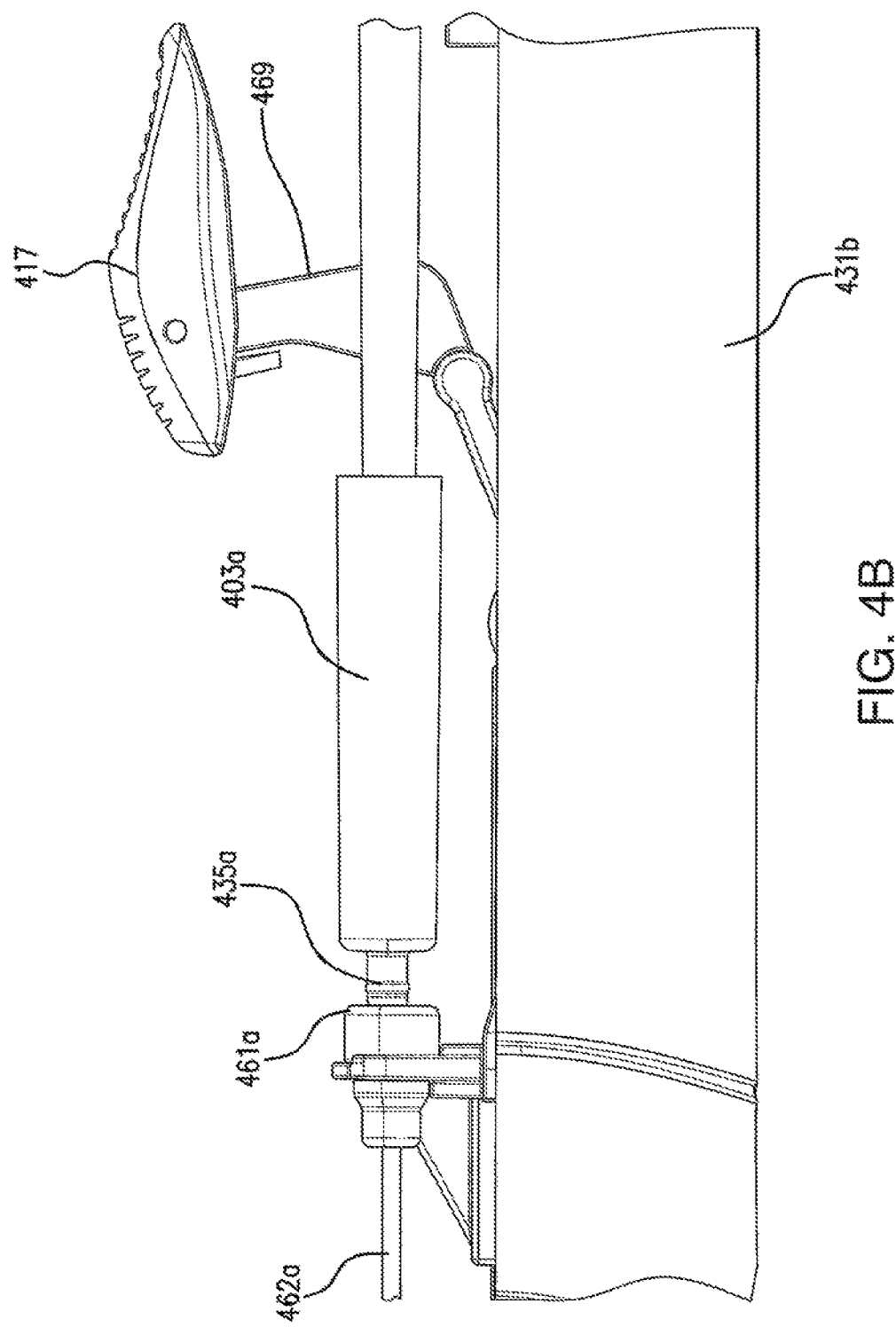

FIGS. 4A-4C show perspective view of interior elements of exemplary controlled delivery device 100 with the top casing removed. FIG. 4A shows a perspective view of the elements for moving catheters so that the catheter distal ends move in and out of the device through exit ports in the insertion tube, and material containers with the material cartridge casings removed. FIG. 4B shows a close-up side view of an exemplary material container (with material cartridge casings removed) and its gasket connection to the material lumen of a catheter. FIG. 4C shows a close-up view of an exemplary air syringe and its connection element for connecting to an air lumen of a catheter for filling a balloon end structure of the catheter (not shown).

Figure 5A:
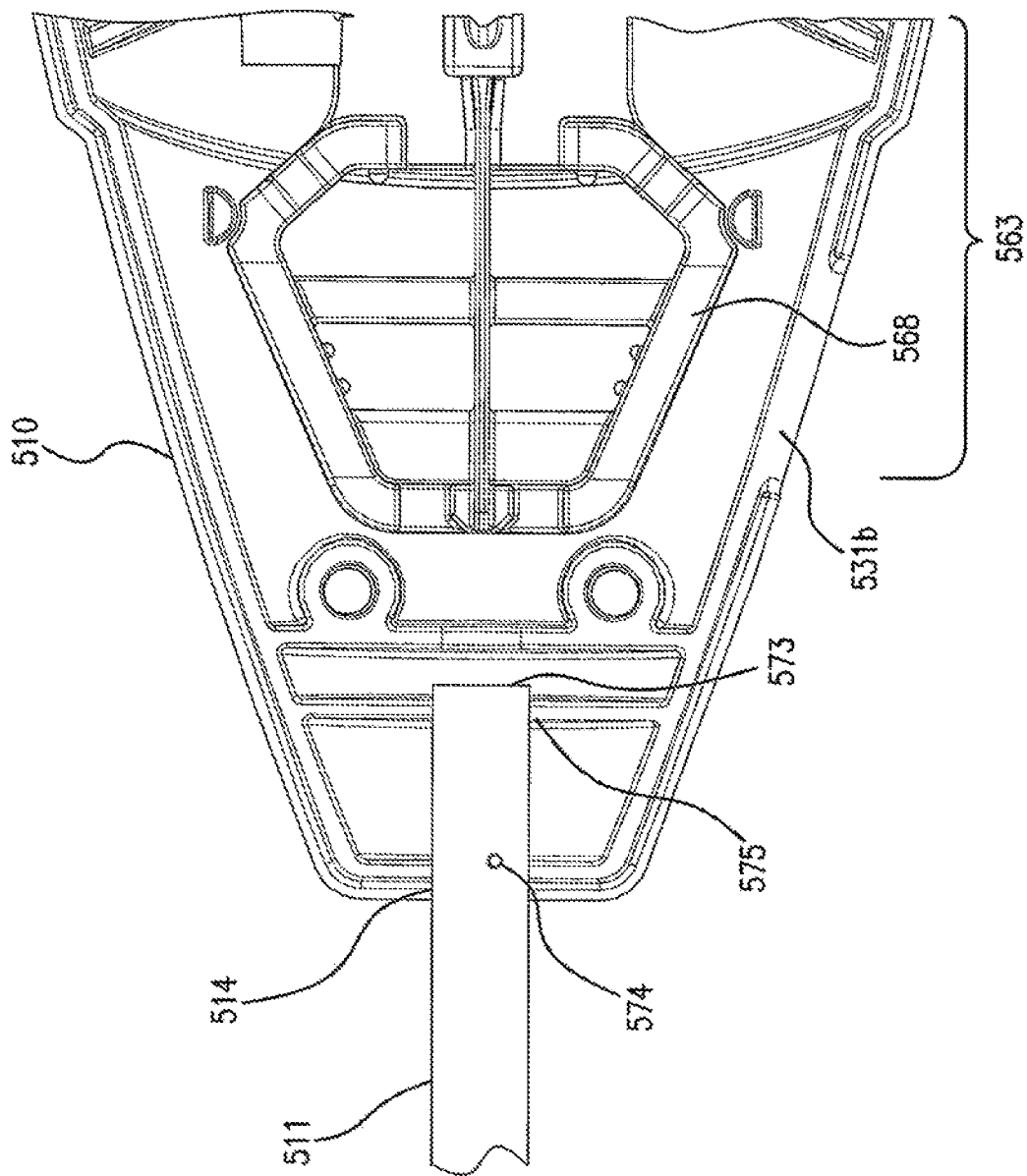
Figure 5B:
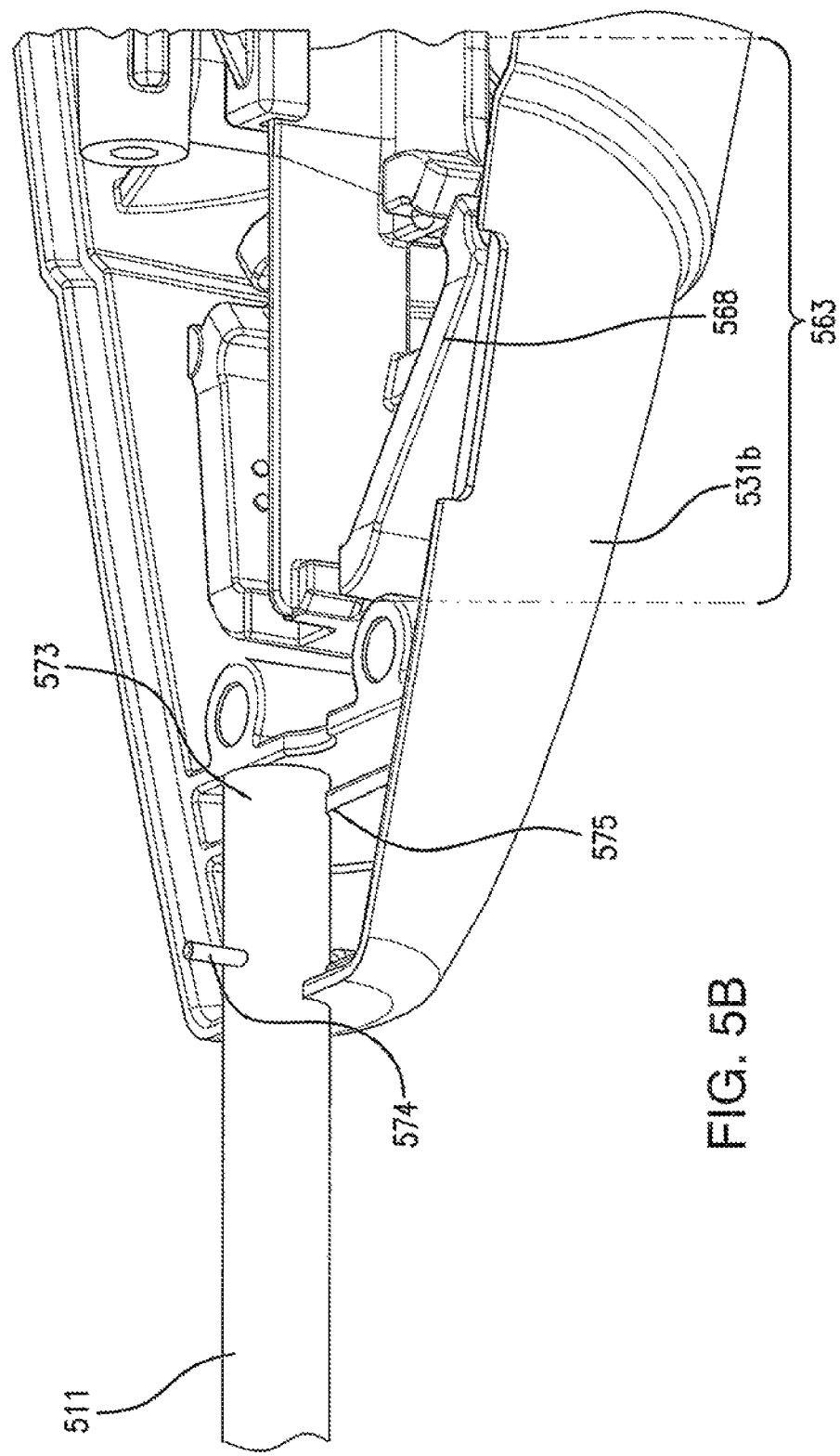

FIGS. 5A-5B show views of the interior of the proximal end of an exemplary controlled delivery device 100. FIG. 5A shows a top view of the interior of the proximal end of the bottom casing of an exemplary controlled delivery device 100. FIG. 5B shows a side perspective view of the interior of the proximal end of the bottom casing of an exemplary controlled delivery device 100.

Figure 6A:
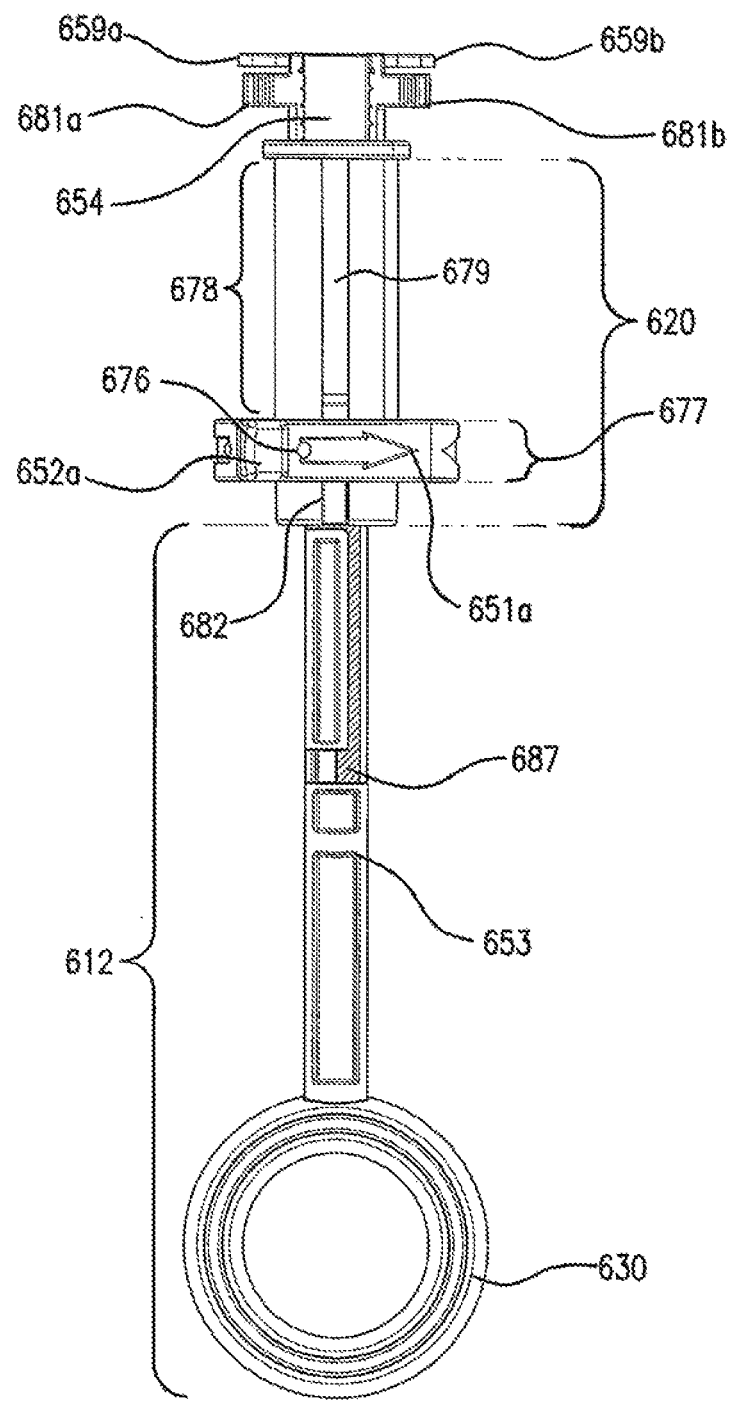
Figure 6B:
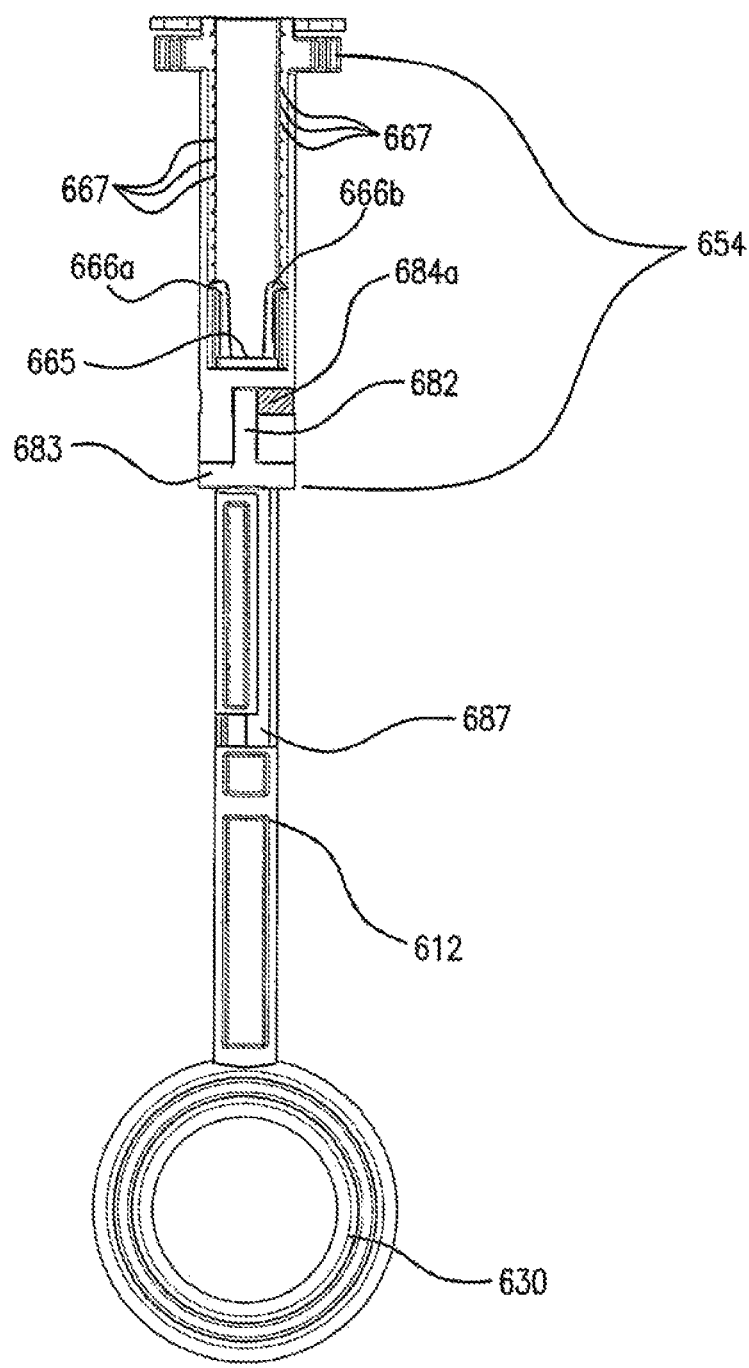

FIGS. 6A and 6B shows a top view of a lock and system plunger of exemplary controlled delivery device 100. FIG. 6A shows a top view of the lock in position 1, and system plunger in position 1. FIG. 6B shows a top view of the lock in position 1, system plunger in position 1, with the lock removed to show interior elements.

Figure 7A:
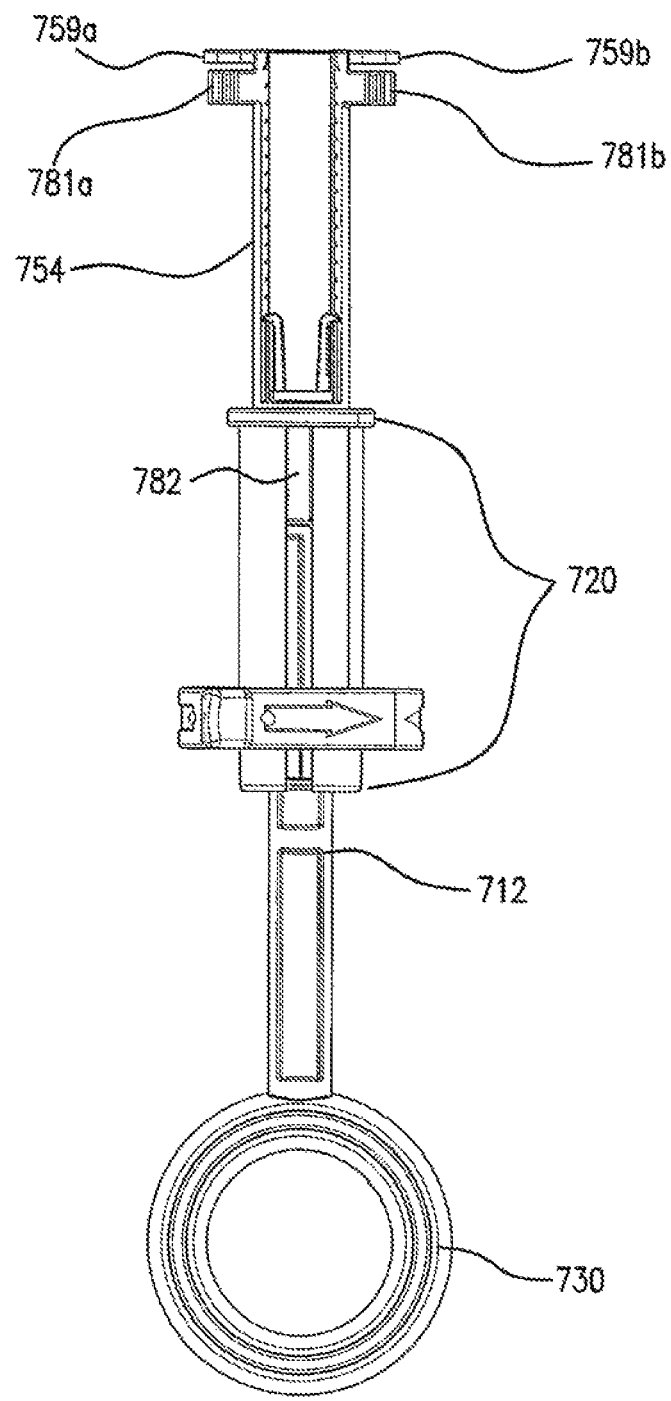
Figure 7B:
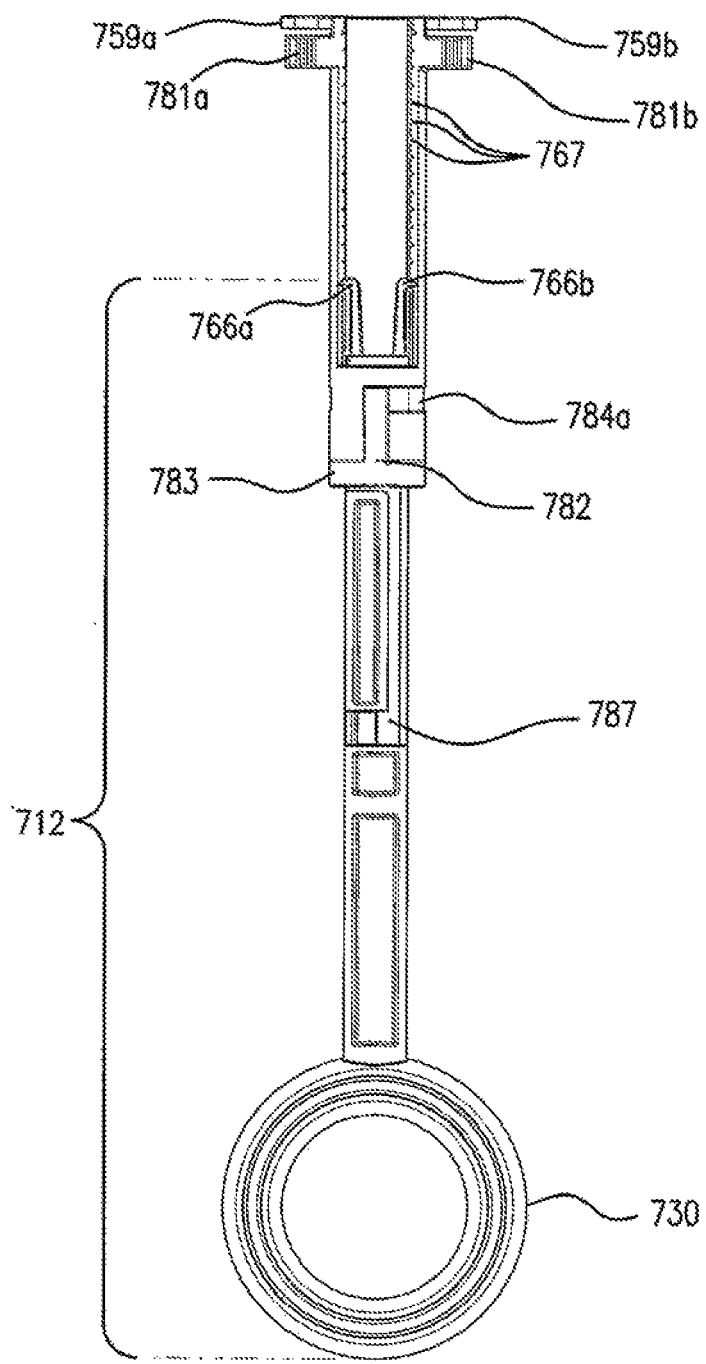

FIGS. 7A and 7B show a top view of the lock and system plunger of exemplary controlled delivery device 100. FIG. 7A shows the lock in position 1, and system plunger in position 2. FIG. 7B shows a top view of the lock in position 1, system plunger in position 2, with the lock removed to show interior elements.

Figure 8A:
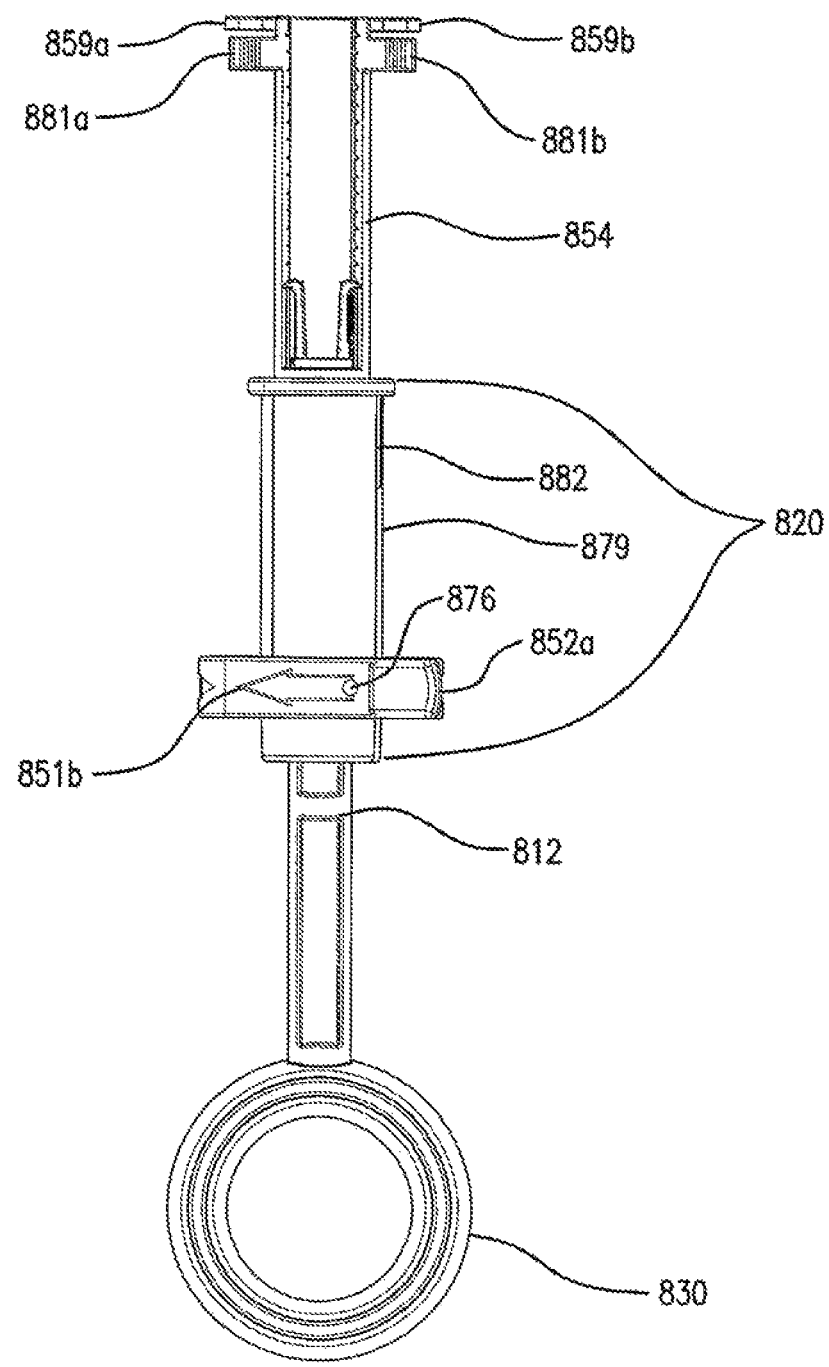
Figure 8B:
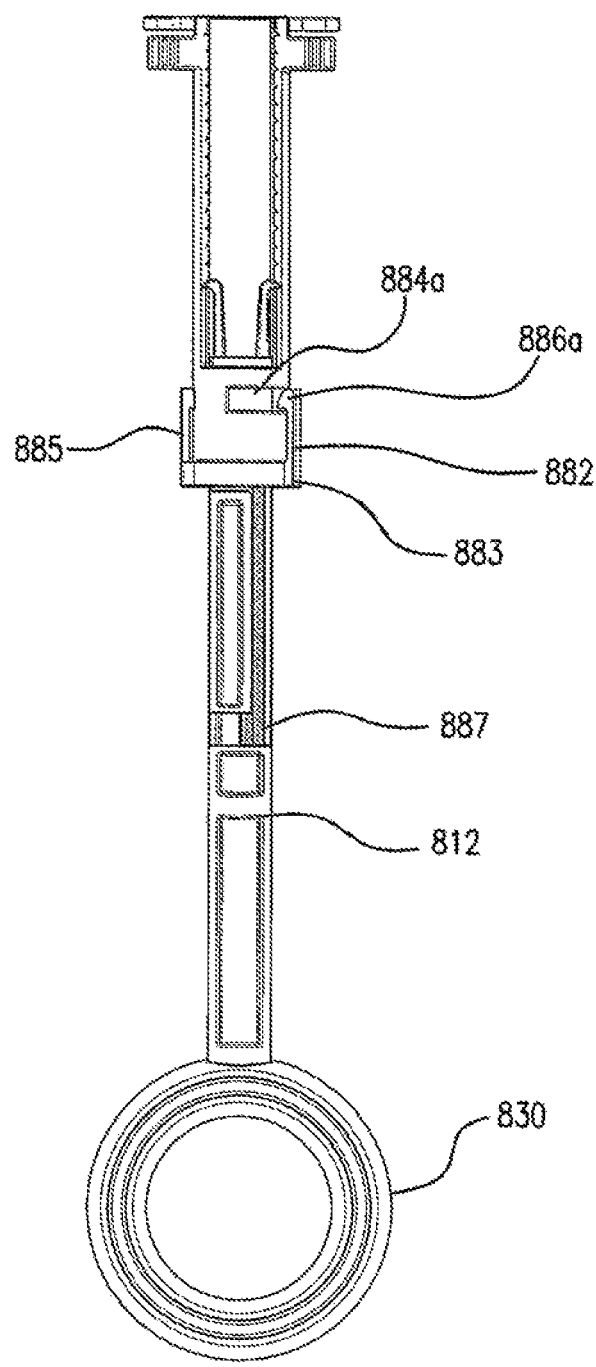

FIGS. 8A and 8B show a top view of the lock and system plunger of exemplary controlled delivery device 100. FIG. 8A shows the lock in position 2, and system plunger in position 2. FIG. 8B shows a top view of the lock in position 2, system plunger in position 2, with the lock removed to show interior elements.

Figure 9A:
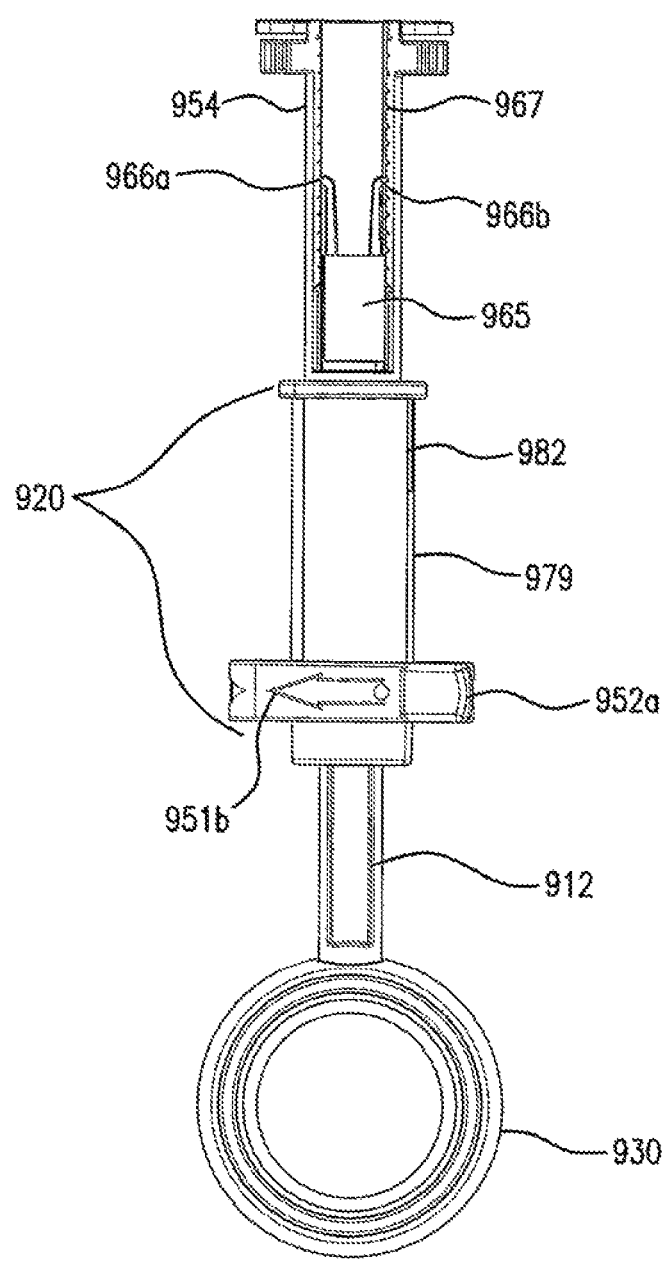
Figure 9B:
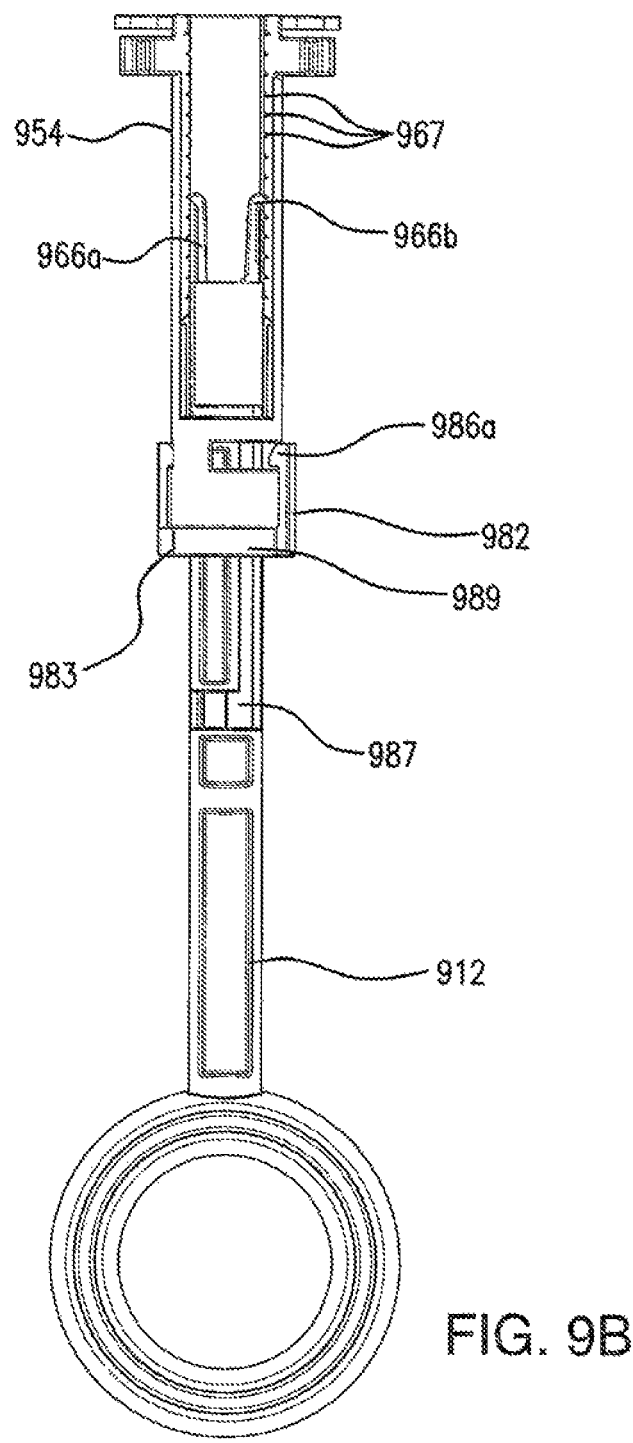

FIGS. 9A and 9B show a top view of the lock and system plunger of exemplary controlled delivery device 100. FIG. 9A shows the lock in position 2, and the system plunger moving to position 3. FIG. 7B shows a top view of the lock in position 2, system plunger moving to position 3, with the lock removed to show interior elements.

Figure 10A:
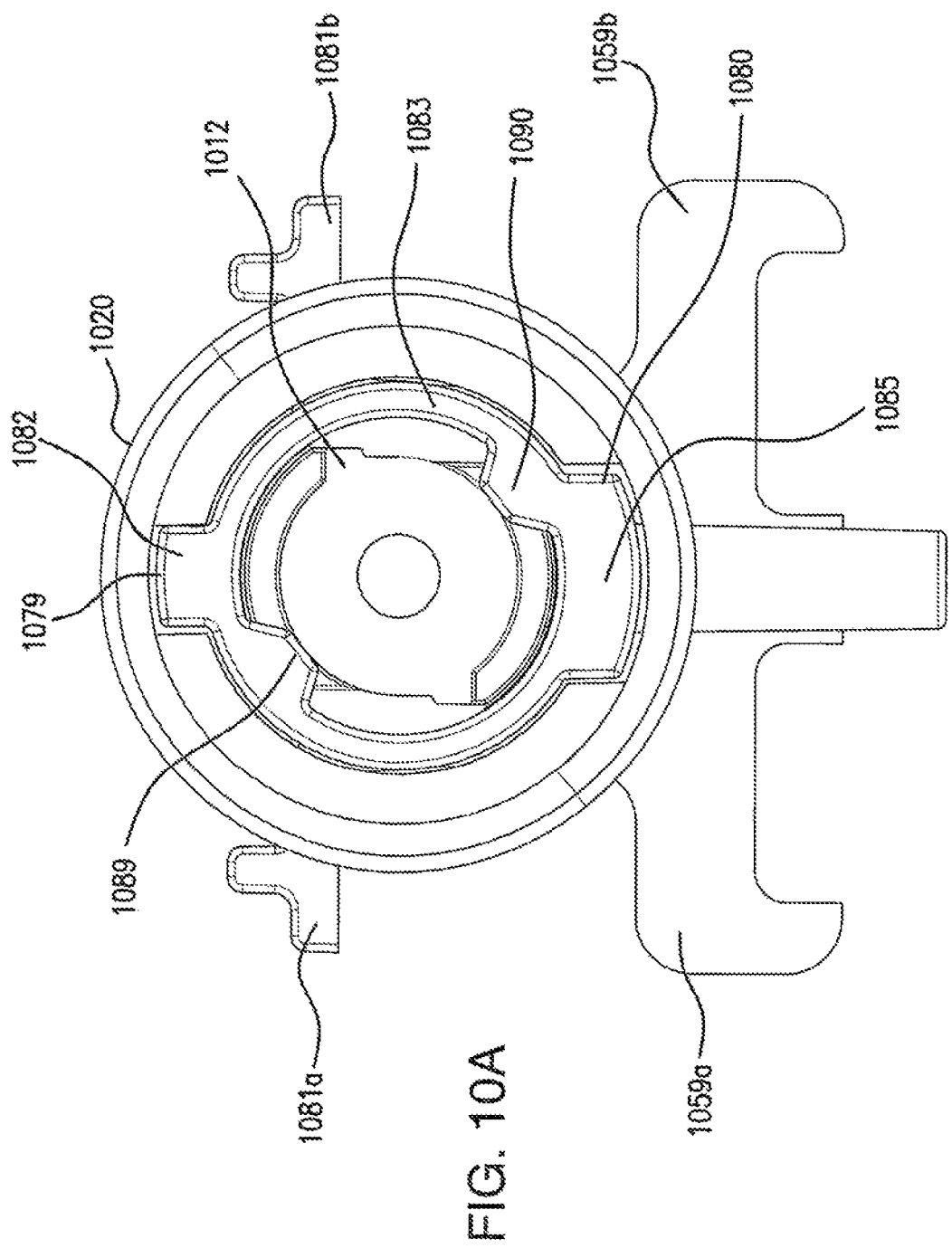

FIGS. 10A and 10B show cross-section views of the lock, coupler and system plunger. FIG. 10A a cross-section view made as indicated in FIG. 3 B, with the lock in position 1 and system plunger in position 2. FIG. 10B shows a side view made as indicated in FIG. 3C, which shows the lock in position 2, and the system plunger in FIG. 2.

DETAILED DESCRIPTION

The present disclosure is directed to devices having specific components that are effective in methods for controlled delivery of compositions to conduits in a mammalian body, particularly controlled delivery to one or more mammalian fallopian tubes. As used in the various figures herein, like numbers are used to describe like elements.

FIG. 1 shows a top view of the exterior of an exemplary controlled delivery device 100 comprising
a) handle 110 comprises a two-part casing 131a/b that encloses interior elements of the device, of which only had casing 131a is visible;
b) hollow insertion tube 111; and
c) system plunger 112; and
d) a rotatable lock 120.

As shown in FIG. 1, an exemplary disclosed controlled delivery device comprises handle 110 which comprises a two-part casing, each comprising a wall that defines an interior compartment (not shown in FIG. 1). Shown in FIG. 1, handle 110 comprises top casing 131a (and bottom casing 131b, not shown), and in an exemplary device, handle 110 may be assembled from two casing parts to form handle 110 and to define openings therein. Handle 110 has a distal end 113 at which casing 131a/b defines opening 114 through which insertion tube 111 traverses from the interior to the exterior of handle 110. Handle 110 has proximal end 115 at which the casing 131a/b defines opening 116 through which system plunger 112 resides and slidably moves. Casing 131a of handle 110 comprises slot opening 118 in which slider 117 is positioned above and slidably moves in a proximal and distal direction. As used herein proximal is closest to the user of the device and towards proximal end 115 of handle 110, and distal is the direction away from the user and closer to distal end 113 of handle 110.

Adjacent to and removed in a proximal direction from distal end 115, casing 131a defines opening 108a (not shown is opening 108b in bottom casing 131b) through which a portion (finger lever 152a) of lock 120 protrudes outwardly, and lock arrow 151a is visible. Lock 120 is in contact with system plunger 112 so as to control the extent of the system plunger 112 movement or the direction of movement, which is shown in later figures.

Handle 110 comprises level 106 which comprises level markings 107. Level 106 functions like known tubular spirit or bubble levels, wherein a container with markings on it contains a mineral oil-like composition that entraps a gas bubble. The gas bubble remains between the level markings when the device with the level is held horizontally, and if the device is rotated leftwardly or rightwardly (counterclockwise or clockwise around an axis line drawn centrally through the insertion tube 111 and handle 110) so that the top of the device is no longer in the horizontal plane, the bubble shifts from its middle position between level markings 107 (the location where the bubble floats when the device is horizontal). For example, a bubble level of an exemplary device may be marked so that each marking indicates a three degree movement from the horizontal plane.

Handle 110 may further comprise tenaculum stabilizer strap 121. Strap 121 may have one or more strap openings 123 therethrough that can mate with prong 122 located on a substantially opposing side of handle 110 or casing 131a. In use, strap 121 is moved so that at least one of opening 123 is in contact with prong 122 (mates with prong 122) so that strap 121 is held stationary by prong 122 inserted through one of opening 123. Strap 121 can be used to hold a tenaculum (not shown) in close contact with controlled delivery device 100 during use of the device.

Insertion tube 111 is a hollow tube having an open proximal end (not shown, see FIG. 5A) which is inserted through opening 114 and is attached in the interior of handle 110, and a closed distal end 124. Closed distal end 124 may be an atraumatic tip. Adjacent to and removed in a proximal direction from closed distal end 124, insertion tube 111 defines two catheter exit ports, 119a and 119b (not shown), which are shown located off-center of an axis line drawn centrally through insertion tube 111 and handle 110. Optionally, located in the hollow core of insertion tube 111, each catheter exit port 119a/b may be proceeded by a ramp (not shown) that aids in positioning the catheters. Located within the hollow core of insertion tube 111 is an optional hollow tube-shaped catheter collar 125 (shown by dotted lines in FIG. 1). Catheter collar 125 comprises a wall that defines a tube having an interior space, and which has a proximal and a distal end. The distal end terminates proximally to the catheter exit ports 119a/b (and catheter ramps, not shown) of insertion tube 111. A distal portion of catheters 104a and 104b reside within the interior space of catheter collar 125, if present. From a proximal to distal direction, portions of the continuous bodies of catheters 104a and 104b traverse through the interior space of insertion tube 111 and through the interior of catheter collar 125, if present, traverse the catheter ramps, if present, and exit insertion tube 111 through exit ports 119a or 119b. Alternatively, insertion tube 111 may internally comprise two individual channels in each of which a catheter resides (i.e., one catheter per channel). A channel may be formed by a centerly positioned septum through the hollow interior of insertion tube 111 which may divide the hollow interior of insertion tube 111 to form two side-by side channels or may divide the hollow of the interior of insertion tube 111 to form two channels located one over the other (using the top of the device for reference of directions—an anterior channel and a posterior channel). Catheters 104a and 104b comprise end structures 105a and 105b, which as shown in FIG. 1 may be balloons. For example, catheters 104a and 104b are dual lumen catheters, wherein one lumen is for delivery of a material composition and the second lumen is for delivery of gas (air) to catheter end structure 105a/b, which are shown in FIG. 1 as balloon end structures.

Insertion tube 111 may further comprise one or more indicator markings 126 which together form uterine depth scale 132 which is used to show the depth of insertion into a uterus of insertion tube 111. Insertion tube 111 may further comprise a slidable flange 127 or depth stop, which may be moved to an indicator marking 126 to indicate to a user that the device's insertion tube 111 is inserted to that particular depth in a uterus.

System plunger 112 has rod-shaped body 153, a distal end (not shown) and a proximal end 130. The distal end (shown in later figures) is shaped to interact with internal elements for filling balloon 105a and 105b with air, and for dispensing a material composition from cartridge material containers 103a/b and through and out catheters 104a and 104b. Proximal end 130 may be shaped so that it can be grasped and moved by one hand of an operator of device 100. As shown in FIG. 1, proximal end 130 is ring-shaped for ease of movement by an operator's thumb or finger. As shown in later figures, system plunger 112's distal end may comprise ratchet pawls so that when system plunger 112 is moved from a second position to a third position in a measured manner, the movement of system plunger 112 in a proximal direction can be controlled and can be heard.

As shown in FIG. 1, an exemplary disclosed controlled device may further comprise material cartridge 101 which snap-fits in cartridge compartment 102, a receptacle defined by an cavity formed in casing 131a. When mating material cartridge 101 in cartridge compartment 102, cartridge material containers 103a and 103b are in fluid connection with the material lumens of catheters 104a and 104b, respectively. Further, cartridge compartment 102 may comprise one or more indents 109a/b. Indents 109a/b each may receive a flange located on material cartridge 101 (see discussion below) and are located in cartridge compartment 102 so that material cartridge 101 is correctly oriented in cartridge compartment 102 so that the lumens of cartridge material containers 103a/b are aligned with material lumens of catheters 104a/b. As shown in FIG. 1, each indent 109 is located proximally of a transverse horizontal axis through cartridge compartment 102. Additionally, on the proximal edge of cartridge compartment 102 is located attachment receptacle 150, shaped to receive an attachment element of material cartridge 101. Material cartridge 101 is described more fully below. A material that may be contained includes, but is not limited to, biopolymers, occlusive agents, therapeutic agents, and diagnostic agents.

FIGS. 2A-F show aspects of an exemplary material cartridge 201. FIG. 2A shows a top view of material cartridge 201, where top casing 233 defines an opening 228 through which material containers 203a and 203b are visible, and central flange 236. Seen are outlet ports 235a and 235b of material containers 203a and 203b, respectively. Central ridge 237 separates the two containers. FIG. 2B shows a bottom (exterior) view of material cartridge 201 which shows the underside of top casing 233 and central flange 236, and the exterior of bottom casing 234, which is shaped to receive material containers 203a and 203b (not visible), and defines two slots 239a and 239b, which are shaped to receive free ends 242a/b of attachment elements 241a/b (not visible), respectively. Bottom casing 234 also defines two attachment flanges, 238a/b which, when material cartridge is placed within device 100, attachment flanges reside within indents 109a/b respectively. Material container outlet ports 235a and 235b of containers 203a and 203b, respectively, protrude beyond the edge of back casing 204 of material cartridge 201. FIGS. 2C and 2D show top casing 233 removed from bottom casing 234 to show the interiors of front casing 233 (FIG. 2D) and bottom casing 234 (FIG. 2C) on which material containers 203a and 203b are positioned. In FIG. 2C, the interior of back casing 234 is shaped so that material containers 203a and 203b are retained therein (not shown). Central ridge 237, protruding outwardly from the interior of back casing 234, separates material container 203a and 203b, aiding in maintaining their positions. Slots 239a and 239b are defined in back casing 234 and are positioned to receive free ends 242a/b, respectively. Also defined on each lateral side of top casing 233 is attachment flange 238a and 238b. Material containers 203a and 203b are hollow cylinders, each having material container outlet ports 235a and 235b, respectively, and each outlet port is open and shaped to mate with a catheter gasket so a fluid connection is formed between the interior of each material container 203a/b and the material lumen of each catheter (not shown). Each material container 203a/b has a proximal end 243a and 243b, each of which is open. Slidably disposed within the cylinders of each of material containers 203a and 203b are material container plungers 240a and 240b. As shown, material container plungers 240a/b are midway along the interior course of material containers 203a and 203b. At the outset of providing material from the containers, plungers 240a/b would be located adjacent to the proximal openings 243a/b of each container 203a/b, respectively, with material contained within the remainder of the interior of the container, distal to the plungers 240a/b. Like known plungers in syringes, plungers 240a/b substantially fill the interior of the respective container in the area where each is located and are used to move material out the material container outlet ports 235 a/b. FIG. 2C shows each plunger as smaller than the interior space only for illustration of fins that may be present on a plunger. Material container plungers 240a/b are moved from a proximal to a distal position in material containers 203a/b by material plunger actuators 358a/b (shown in FIG. 3A) and move the material contained within the material containers 203a and 203b into the material lumen of a catheter (not shown) having a gasket with which material container outlet ports 235a and 235b are mated and form a fluid connection. Attachment element 250b is positioned on the proximal end of back casing 234, and is shaped to mate with attachment receptacle 150 formed in cartridge compartment 102 of top casing 133 of exemplary device 100. FIG. 2D shows the interior face of top casing 233, which defines two upwardly extending casing attachment elements, 241a and 241b, for attaching top casing 233 to bottom casing 234 by inserting the free ends 242 a/b of attachment elements 241a and 241b into slots 239a and 239b in back casing 234. Central flange 236 is positioned on the distal end of top casing 233 and functions to aid in holding material cartridge 101 in receptable 102 by fitting with the distal center edge of receptable 102.

FIG. 2E shows a front view of material cartridge 201 wherein front surface 245a of top casing 233 and front surface 245b of back casing 234 are shaped so that when top casing 233 and bottom casing 234 are attached together, form outlet port openings 246a and 246b through which material container outlet ports 235a and 235b of material containers 203a and 203b (not shown) protrude. Outlet ports 235a and 235b are open so that material contained with material containers 203a and 203b can be extruded. Also seen is attachment element 236 (e.g., a protrusion) for holding the front end of material cartridge 201 in receptacle 102 of controlled delivery device 100 (see FIG. 1). Also shown are attachment flanges 238a/b and the proximal side of attachment element 249.

FIG. 2F shows the side of material cartridge 201 opposing the view in FIG. 2E, a back view of material cartridge 201 wherein bottom surface 247a of top casing 233 and bottom surface 247b of bottom casing 234 are shaped so that when top casing 233 and bottom casing 234 are attached together, form openings 248a and 248b through which container material plungers 240a and 240b can be contacted (respectively) and if desired, moved (not shown). Also shown is attachment element 249 for holding the back end of material cartridge 201 by snap-fitting with attachment element receptacle 150 defined by top casing 131a in receptacle 102 of controlled delivery device 100 (see FIG. 1). Also shown are attachment flanges 238a/b.

FIGS. 3A-3G show side and top views of interior elements of an exemplary controlled delivery device 100 and their movements during use of the device, with the top and bottom casings removed. FIGS. 3A-3G display movements of elements in the controlled order used in operating device 100 for controlled delivery of a material to the cornua of fallopian tubes of a mammal. FIG. 3A shows a side view of the interior elements of controlled delivery device 100 prior to initiating use. System plunger 312 is fully extended in a proximal direction (proximal end 330 is extended to the right in FIG. 3A), which is system plunger position 1. Lock 320 is in lock position 1. As shown in FIG. 1, from the top surface, lock arrow 151a is pointing to the right, whereas from a side view in FIG. 3A, lock arrow 351b is seen and points in the opposite direction. The head portion of lock arrow 351b' is seen in FIG. 3A. From the bottom view of device 100, which is not shown, arrow 351b' and finger lever 152b would be visible through slot 108b formed in back casing 131b, which corresponds to slot 108a in front casing 131a. Finger lever 152a of FIG. 1 is shown as 352a in FIG. 3 (finger lever 152b is not visible). Rod portion 353 of system plunger 312 includes lock engaging elements 362, generally a notch, indentation or groove in rod 353, which in conjunction with lock 320, control the movement of system plunger 312 and thus other interior elements. Moving in a distal direction, the tubular portion of lock 320 is followed by control rod 354, which is a hollow tube having attachment elements 359a and 359b (not shown) on its distal posterior end and positioning elements 381a and 381b (not shown) on its distal anterior end (see later figures). On its proximal end, control rod 354 is connected to a distal portion of system plunger 312 by a coupler, and the distal ends of system plunger 312 are inserted within an interior portion of control rod 354. See later figures. On its distal end, control rod 354 defines two sets of parallel connecting elements, posteriorly attachment elements 359a and 359b, and anteriorly, positioning elements, 381a and 381b. Distally, control rod 354, on its posterior end (towards the bottom of device 100) has attachment elements 359a/b to connect to the proximal ends of air syringe plungers 355a and 355b respectively (only one plunger is visible in FIG. 3A side view). The distal ends of air syringe plungers 355a and 355b reside within air syringes 356a and 356b (not shown), respectively. The proximal ends of air syringes 356a and 356b are closed by the respective air syringe plungers and the distal ends are connected to air lumens 357a and 357b (not shown) in catheters 104a and 104b and the air moved from the air syringes is used to fill end structures (balloons) 105a and 105b of catheters 104a and 104b (see FIG. 1), respectively.

Distally, control rod 354, on the anterior (towards the top of device 100) has positioning elements 381a/b on which are positioned material plunger actuators 358a and 358b respectively (only one actuator is visible in FIG. 3A side view). Control rod 354 is substantially a hollow tube, which in its central and distal portions, has an anterior open top, ratchet teeth on opposing lateral sides and having a substantially flat posterior lower surface throughout, and in the initial proximal portion is a closed hollow tube with no ratchet teeth. Material plunger control 329 comprises proximal end 360 and two material plunger actuators 358s and 358b. Proximal end 360 is slidably positioned in the interior of control rod 354 so that proximal end 360 is movable along the lower interior surface of control rod 354, distal to the closed top portion of control rod 354. The distal ends of material plunger actuators 358a/b can movably contact material plungers 240a and 240b (not shown here) located within material containers (see FIG. 2) when proximal end 360 is moved in a distal direction. Material plunger actuators 358a/b will simultaneously move material plungers 240a and 240b (not shown), which reside inside cartridge material containers 303a/b. Material containers 303a and 303b are located inside material cartridge 101, but the material cartridge is not shown in FIG. 3A-3G so that interior elements and their relationships can be shown. It is assumed that material cartridge 101 (not shown) is fitted in place so that outlet ports 335a/b of material containers 303a and 303b are in fluid communication with material catheter gasket 361a and 361b which fluidly connects to material catheter lumens 362a and 362b of catheters 104a and 104b (FIG. 1), so that material contained in material containers 303a and 303b is moved from material containers 303a and 303b through outlet ports 335a/b, through material catheter gaskets 361a and 361b into material catheter lumens 362a and 362b of catheters 104a and 105b (not shown) and finally, out distal ends of catheters 104a and 105b. In FIG. 3A, material containers 303a/b are shown not in contact with gaskets material catheter gaskets 361a and 361b to illustrate outlet ports 335a/b of material containers 303a, though in actual use, container outlet ports 335a/b mate with material catheter gaskets 359a/b once material cartridge 101 is mated with device 100. Generally, one of the elements, e.g., the "b" elements, are not shown in several of these drawings because of the side angle view, and the generally parallel relationship between "a" and "b" elements means that only one, either "a" or "b" would be visible from a side (or top/bottom) view. Catheter slide 363 is shown positioned medially between the anteriorly located material cartridge 101 (not shown but indicated by material container 303a) and posteriorly located air syringes 341a and 341b. Catheter slide 363 is movable in a proximal to distal direction and distal to proximal direction as moved by slider 117 (not shown). Portions of the bodies of catheters 104a and 104b are positioned on catheter slide 363. Catheter slide 363 is described more fully below.

FIG. 3B shows a side view of interior elements of controlled delivery device 100 after system plunger 312 has moved in a distal direction to system plunger position 2 (see Arrow 1 to indicate movement in the distal direction, left in the FIG. 3B). System plunger position 2 is confirmed to the user by one of lock engaging elements 362 (not shown) contacting lock 320. Tactilely, a click is felt or heard, and system plunger 312 cannot advance further in a distal direction, nor can system plunger 312 be moved in a proximal direction to return to system plunger position 1. Lock 320 is shown more fully below. Because system plunger 312 and control rod 354 are coupled together to form a connected rigid system, the lateral distal movement of system plunger 312 advances control rod 354 in a distal lateral direction, see arrow 2, which moves air syringe plungers 355a/b through the interior of air syringes 356a/b, respectively. Movement of air syringe plungers 355a and 355b in a distal direction in air syringes 356a and 356b (see arrow 3), moves air from the air syringes 356a and 356b into the air lumens 357a and 357b of catheters 104a and 104b, respectively, and extends end structures, e.g., balloons, 105a and 105b, respectively. Also shown is catheter slide 363, and other elements as shown in FIG. 3A.

FIG. 3C shows a side view of interior elements of controlled delivery device 100 with elements positioned similarly to those shown in FIG. 3B except that lock 320 has been rotated from lock position 1 to lock position 2, wherein from the side view finger lever 352 and arrow 351b' are seen. From a top view, arrow 351b is visible. Moving lock 320 to lock position 2 disconnects, via a coupler (shown in later figures), the movement of system plunger 312 from the movement of control rod 354. Once disconnected, as seen in following figures, the distal ends of system plunger 312 can move in a distal direction interacting with the rachet teeth in the interior of control rod 354 and control rod 354 remains stationary.

FIG. 3D shows a side view of the interior elements of controlled delivery device 100 with system plunger 312 leaving position 2 and moving distally towards position 3. With lock 320 in lock position 2, distal end 365 of system plunger 312 moves distally to contact proximal end 360 of material plunger control 329 so that material plunger actuators 358a/b are moved in a distal direction, while control rod 354 remains stationary. The other elements and positions are the same as in FIG. 3C.

FIG. 3E shows a top view of interior elements of controlled delivery device 100 in positions similar to those seen in FIG. 3B above, except that system plunger 312 is in system plunger position 2 and lock 320 is in lock position 2. Rachet pawls 366a/b extend from distal end 365 of system plunger 312. Distal end 365 is contacting and positioned to push, in a distal direction (to the left in FIG. 3E) proximal end 360 of material plunger control 329 causing material plunger actuators 358a/b to move into the open end of material containers 303a/b wherein material plungers 240a/b are contacted (not shown), and material plungers 335a and 335b is shown. Material plunger actuators 358a/b and proximal end 360 form a U-shaped material plunger control 329, in which the proximal end 360 is the closed U section, and the posterior surface of proximal end 360 is slidably positioned at the proximal-most location in the anterior open area of the hollow tube of control rod 354 (not shown) and the material plunger actuators 358a/b are positioned parallel with the edges of the open top portion of control rod 354. Catheter slide connector 363 is shown extending from its proximal end 371 to its distal end 368, and is a substantially flat member. Proximal end 371 of catheter slide 363 is slidably connected to catheter slide connector 370 so that when catheter slide connector is moved in a distal or proximal direction, catheter slide 363 moves similarly. Catheter slide 363 bears the bodies of catheters 105a/b which are wound around the top surface catheter slide 363.

FIG. 3F shows a top view of the interior elements of controlled delivery device 100, illustrating the positions of elements after movements following the steps shown in FIGS. 3D and 3E. As shown in FIG. 3F, system plunger 312 is in system plunger position 3 and lock 320 has been returned to lock position 1 by rotating the lock levers counterclockwise. Just prior to FIG. 3F, system plunger 312 moved in a distal direction (leftward in FIG. 3F) to reach system plunger position 3, while lock 320 was in lock position 2. System plunger 312 moved laterally in a distal direction, which moved rachet pawls 366 along rachet teeth 367 located on the interior opposing sides of control rod 354. Control rod 354 remained stationary. The movement of the rachet elements (teeth and pawls) gives tactile notice to the user by potentially feeling and hearing the "clicking" of the rachet pawls moving over the rachet teeth. Distal lateral movement of distal end 365 of system plunger 312 moves proximal end 360 of material plunger control 329 advancing material plunger actuators 358a/b which then contact the material plungers 240a/b in the material containers (not shown in FIG. 3F) to move material from the containers. Container material plungers 240a and 240b are moved from a proximal to distal position, moving the contained material, e.g., a biopolymer or occlusive agent, therapeutic agent or diagnostic agent, from inside material containers 303a and 303b, out outlet ports 335a/b, through material gasket 361 a/b, and into material lumens 362a and 362b, respectively, of catheters 104a and 104b, respectively, and then an effective amount is moved through and out distal ends of catheters 104a and 104b, respectively. Once an effective amount of material has moved through and out the distal ends of catheters 104a and 104b, lock 320 is rotated in a clockwise direction to return lock 320 to lock position 1, as shown in FIG. 3F. The rotation to position 1 of lock 320 re-establishes the rigid connection between control rod 354 and system plunger 312 so that control 354 and system plunger 312 will move simultaneously together and in the same direction. This reconnection allows system plunger 312 and control rod 354 to move in a proximal direction (retract) which causes the air plungers 355a/b, attached to control rod 354, to move in a distal to proximal direction, which will deflate end structures 105a/b on catheters 104a and 104b respectively. If lock 320 is not rotated to position 1, system plunger 312 and control rod 354 cannot retract. In use in a patient, once end structures 105a/b are deflated, device 100 may be removed.

FIG. 3G shows a side view of interior elements of controlled delivery device 100 as positioned in FIG. 3F. System plunger 312 is in system plunger position 3, (it has moved in a lateral distal direction (leftward in FIG. 3G) to reach system plunger position 3). Distal end 365 of system plunger 312 has moved proximal end 360 so that material plunger actuators 358a/b are substantially positioned within material containers 303a/b. Lock 320 has been rotated clockwise to position 1, which occurs after material has been provided through the catheters. Other labeled elements are as described above.

FIG. 4A-C show exemplary views of interior elements of controlled delivery device 100, illustrating elements involved in catheter movements and air movement. Shown in FIG. 4A is a perspective view of handle 110, with top casing 133a removed, to show placement relationships of interior elements such as lock 420, material containers 403a and 403b, and material lumens 462a and 462b of catheters 104a and 104b, to catheter movement elements of slider 417, slide advancement lever 469 catheter slide connector 470 and catheter slide 471. Slider 417, which is generally ovoid in shape and, as shown, has a ridged ramp on its anterior surface for finger placement for movement, is located along the central axis of device 100, positioned to protrude above and between material plunger actuator 458a and 458b, and is connected on its posterior side to catheter slide advancement lever 469. Slide advancement lever 469 is a perpendicularly extending rod (perpendicular to the central axis) and extends from the posterior side of slider 417 and is connected to catheter slide connector 470, which is slidably connected to proximal end 471 of catheter slide 463. Slider 417 can be moved in a proximal to distal direction and distal to proximal direction, and movement of slider 417 in turn moves catheter slide advancement lever 469 in the same direction, which moves catheter slide connector 470, which slidably moves catheter slide 463, which advances or retracts the distal ends of catheters 104a and 104b into or out of catheter exit ports 119a and 119b, respectively, in insertion tube 111 (see FIG. 1). The bodies of catheters 104a and 104b are wrapped on and around catheter slide 463, which aids in orienting the catheters. Distal ends of catheters 104a and 104b are initially positioned at the catheter exit ports 119a and 119b, and the remainder of the catheter bodies, in a distal to proximal direction, are positioned inside catheter collar 125 (positioned in a proximal portion of insertion tube 111) and through the length of the insertion tube 111, enter handle 110, and are wound on and about catheter slide 463, leaving the proximal ends of each of the lumens for attachment to each respective gasket. For example, catheters 104a and 104b are dual lumen catheters, each having an air lumen and a material lumen. When catheter slide 463 is moved in a distal direction, catheter ends move out of exit ports 119 a/b, and when catheter slide 463 is moved in proximal direction, catheters ends are drawn toward and to exit ports 119a/b. As shown in FIG. 4B, the proximal ends of catheters 104a and 104b, dual lumen catheters, (not shown) are attached so that material lumens 462a/b are in fluid connection with material containers 403a and 403b, respectively, so that an effective amount of material can be moved from material containers 403a and 403b, through outlet ports 435a/b, through catheter gaskets 461a/b through the material lumens 462a/b of the catheters and out the catheters' respective distal openings. Material containers 403a/b each have a distal material container outlet port 435 a/b shaped to mate with material catheter gaskets 461a/b to make a fluid connection between material container 403a/b and material catheter lumen 462a/b of a respective dual lumen catheter, 104a or 104b. Material catheter lumens 462a/b are proximally fluidly connected to material catheter gaskets 405a or 405b, respectively, which may be a Pebax® gasket. The proximal side of material catheter gaskets 461a/b mate with material container outlet ports 435a and 435b (See FIG. 2). Though not shown as mated in FIG. 4B, when material cartridge 101 is inserted into receptacle 102 of handle 110, material outlet ports 435a and 435b press fit with catheter gaskets 461a/b, respectively, to mate and form a fluid connection. Catheter material gaskets 461a and 461b may be attached to material catheter lumens 462a and 462b by any known attachment methods, such as bonded or insert molded.

FIG. 4C shows a closeup of air syringe 456a (which is mirrored by air syringe 456b, not shown) and elements for expanding and deflating catheter end structures 105a and 105b. Air syringe plunger 455a movingly seals the open end of air syringe 456a. The connector end 472a (distal end, on the left of FIG. 4C) of air syringe 456a fluidly connects with air lumen 457a of a dual catheter. As shown, connector 472a, for example, a luer lock, is used to connect air syringe 456a with air lumen 457a. Air syringe 456a may be prefilled with air or gas, is initially filled with air by atmospheric pressure. For example, catheter air lumen 457a has a female luer lock on its proximal end and air syringe 356a has a male luer lock on its distal end to form a fluid connection for gas transmission through the catheter air lumen 457a.

FIGS. 5A and 5B shows a top and a side perspective views of the interior elements of controlled delivery device 100, illustrating elements involved in attachment of insertion tube 511 to structural elements formed in the interior of bottom casing 531b of controlled delivery device 100. Insertion tube 511 enters handle 510 at opening 514 defined by the top and bottom casings 531a/b of handle 110 and is held in place by an insertion tube pin 574 traversing two aligned holes defined by the wall of insertion tube 511. The opposing ends of insertion tube pin 574 mate with bosses on the interior of the top casing 531a and bottom casing 532b of handle 110 (not shown). The proximal end 573 of insertion tube 511 is positioned on bottom housing rib 575, formed on the interior of bottom casing 531b. Not shown is the interior of top casing 531a of handle 110 which has a matching rib to encircle insertion tube 511. Insertion tube pin 574 prevents rotation of insertion tube 511. In placing catheters within device 100, the distal ends of catheters (not shown) are fed into proximal end 573 and then to the exit ports adjacent to the closed distal end 124 of insertion tube 511 (not shown). Also shown in FIG. 5A is distal end 568 of catheter slide 563. FIG. 5B shows similar elements in a perspective view, with top casing 531a removed to show positions of elements with bottom casing 531b, including insertion tube 511, insertion tube pin 574, bottom housing rib 575 and distal end 568 of catheter slide 563. 6A and 6B are top views of elements involved in the movements of system plunger 612, control rod 654 and lock 620 with each positioned at an initial time, system plunger position 1 and lock position 1, prior to any movement of system plunger 612, similar to positions as shown in FIG. 1. Lock 620 is a one-piece lock comprising a hollow annular lock proximal end 677 followed distally by lock collar 678, a hollow tube. Lock proximal end 677 is an annular ring that defines two protruding finger levers which space apart two pairs of indicia (shown as two pairs of facing arrows, e.g., arrow point to arrow point). In FIG. 6A, lock 620 is in lock position 1, with arrow 651a visible and finger lever 652a protruding outwardly in a leftward direction. Detent 676, of which one detent is located at the tail end (opposite the pointed end of the arrow) of each arrow of lock 620, is visible. If casing 131a were in place, only the finger lever, the arrow and and detent would be visible through slot 108a. A detent 676 is located at the tail end of each arrow (total of 4 arrows and 4 detents) of lock 620 and are used to hold lock 620 stationary once the lock has been rotated, by maintaining a portion of top casing 131a between a detent 676 (of an arrow not shown) and finger lever 652a. Similar arrows, finger lever and detents are mirrored on the opposite side of the lock and a detent on the opposite arrow holds bottom casing 131b between that detent and finger lever 652b (not shown). When rotated to lock position 2, visible detent 676 of FIG. 6A will hold lock 620 stationary by holding the edge of slot 108a in casing 131a between finger lever 652a and the now-visible detent 676 (after rotation, now-visible detent 676 will no longer be visible). Lock 620 further comprises lock collar 676, which is shaped as a hollow tube having two slots therein, wherein shown slot 679 is more narrow in width than is slot 680 (not shown). Control rod coupling protrusion 682 is sized to protrude and fit within slot 679. Both lock slot 679 and coupling protrusion 682 are positioned on the central axis of device 100 at lock position 1 and system plunger position 1. Groove 687 is defined in system plunger rod 653. Distal end of control rod 654 is visible with its positioning elements 681a/b anteriorly and attachment elements 659a/b posteriorly.

FIG. 6B shows the same view as FIG. 6A, except that lock 620 has been removed. A top view of control rod 654 and system plunger 612 is shown. Distal end 665 of system plunger 612, which comprises two rachet pawls 666a/b, extends into the proximal end of control rod 654, and the rachet pawls 666a/b are positioned on the first of rachet teeth 667, which line the interior lateral sides of hollow tube control rod 654, and are seen through the anterior opening of control rod 654. The proximal end of control rod 654, which is continuous with the rest of control rod 654, is not open anteriorly, and instead is a hollow tube having two opposing slots 684a/b defined therein. Each slot starts on the midline (along the central axis, as used herein is drawn from proximal end of system plunger through insertion tube) of control rod 654, one anteriorly and one posteriorly, and proceeds approximately 90 degrees in a rightward (counterclockwise) direction in the rounded tube. In FIG. 6B only slot 684a is partially visible. Rotationally slidably fitted on the proximal end of control rod 654 is control rod coupling 683, which comprises a ring-shaped base and narrow control rod coupling protrusion 682 and wider control rod coupling protrusion 685 (not shown). The protrusions, 682 and 685, extend perpendicularly in a distal direction from the ring-shaped base of control rod coupling 683, and are shaped to protrude above the plane of the ring-shaped base of control rod coupling 683, and to fit within slots 679 and 680, respectively, of lock 620, with narrower protrusion 682 fitting within slot 679 and protrusion 685 fitting within slot 680. Not shown in this figure but at the distal end of each protrusion 682 and 685, opposite the ring-shaped base, each protrusion has a small perpendicular projection 686a/b, extending inwardly towards the center of control rod 654 that is slidably positioned within a slot of control rod 654, either slot 684a or slot 684b. Coupling 683 can rotate from its midline starting position rightward approximately ninety degrees because the perpendicular protrusion 686a/b is stopped by the end of the slot in which the protrusion resides respectively. Not shown in FIGS. 6A and 6B, but on the interior of the ring base of coupling 683 are two groove projections, 689 and 690, which project inwardly towards system plunger 612, and generally rest on the surface of system plunger 612. Groove projection 689 is located interiorly on the ring-shaped base at a site substantially adjacent to, but removed in a clockwise direction from, the proximal end of coupling protrusion 682, and groove projection 690 is located interiorly on the ring-shaped base at a site substantially adjacent to, but removed in a clockwise direction from, the proximal end of coupling protrusion 685. Defined in the anterior surface of the rod portion of system plunger 612 is groove 687, and a corresponding groove 688 is defined in the posterior surface of the rod portion of system plunger 612. In later figures, it will be seen that groove projection 689 will be positioned in groove 687 and groove projection 690 will be positioned in groove 688.

FIGS. 7A and 7B show top views of lock 720 and control rod 754 after system plunger 712 has moved to position 2, by moving in a proximal to distal direction until system plunger 712 is positioned so that lock 720 can be moved. In system plunger positions 1 and position 2, system plunger 712 and control rod are connected via the coupler (see below) so that the two elements form a rigid combined rod-plunger system such that when system plunger 712 moves in a proximal to distal direction, control rod 754 moves the same distance in a proximal to distal direction. Not shown in FIG. 7A, is that the movement of system plunger 712 to position 1 and its associated movement of control rod 754, has caused the air syringe plungers (not shown), which are connected to attachment elements 759a and 759b, respectively, of control rod 754 to advance and expel air out of the air syringes and into the air lumen of the two catheters so that the end structures, e.g., balloons, are inflated. As shown in FIG. 7A, lock 720 now surrounds a central section of the rigid combined control rod 754 and system plunger 712. Compare to FIG. 6A where lock 620 substantially surrounded control rod 654. The other numbered elements are the same as in FIG. 6A and FIG. 6B.

FIG. 7B shows the same top view as FIG. 7A, except that lock 720 has been removed. A top view of control rod 754 and system plunger 712 is shown. Like elements are numbered as in 7A, and FIGS. 6A and 6B.

FIGS. 8A and 8B show top views of top views of lock 820 and control rod 854 after system plunger 712 has moved to position 2, and lock 820 has moved to lock position 2. In FIG. 8A, now visible is arrow 851b (pointing to the left) and detent 876, and finger lever 852a has rotated clockwise to the right.

FIG. 8B shows the same top view as FIG. 8A, except that lock 820 has been removed. A top view of control rod 854 and system plunger 812 is shown in position after lock 820 was moved to lock position 2 by rotating lock 820 rightwardly from lock position 1. Movement of lock 820 to position 2 also rotates coupling 883 because protrusion 882 is positioned within lock collar slot 879 (protrusion 885 positioned in slot 880, not shown, has also rotated) and both slots and coupling 883 move in concert. In FIG. 8B, the side of protrusion 882 is visible, showing projection 886a positioned within control rod slot 884a. Coupling protrusion 885 is also visible.

FIGS. 9A and 9B are top views of lock 920 and control rod 954 with system plunger 912 moving to position 3, and lock 820 is in lock position 2. See arrow 951b pointing to the left and finger lever 952a rotated to the right. Moving lock 920 to position 2, rotates lock 920 so that slot 979 rotates rightwardly (clockwise), moving coupling protrusion 982 rightwardly. Moving lock 920 to position 2 uncouples the rigid system plunger-rod connection of system plunger 920 and control rod 954, so that further movement of system plunger 912 in a distal direction does not move control rod 954. Instead, in moving to system plunger position 3, distal end 965 of system plunger 912 moves distally in the interior of control rod 954 with the rachet pawls 966 a/b connecting with rachet teeth 967, while control rod 954 remains stationary. FIG. 9A shows distal end 965 less than halfway in its transit through the interior of control rod 954.

FIG. 9B shows the same top view as FIG. 9A, except that lock 920 has been removed. A top view of control rod 954 and system plunger 912 is shown. Control rod coupling 983 has rotated rightwardly so that groove projection 989 (not shown but indicated by arrow pointing to the interior of the ring base of coupling plunger 983) is now positioned in groove 987, and not shown is groove projection 990 positioned in groove 988 in the posterior (or bottom) surface of system plunger 912. Positioning groove projection 989 in groove 987, and similar positioning of groove projection 990 in groove 988 on the posterior side (not shown) allows system rod 912 to advance distal end 965 and its rachet pawls 966*a/b* through the interior of control rod 954, and control rod 954 does not move.

FIGS. 10A and 10B show a cross-section, looking from a proximal to a distal direction, of lock 1020, coupling 1083, and system rod 1012. FIG. 10A shows a cross-section at the position shown in FIG. 3B, with lock 1020 in position 1, wherein system plunger 1012 and control rod 354 (not shown) are coupled together for uniform movement. Lock slot 1079 (more narrow slot) is positioned anteriorly on the midline (central axis) and lock slot 1080 (wider slot) is positioned posteriorly on the central axis. Coupling protrusion 1082 is positioned within lock slot 1079, and coupling protrusion 1085 is positioned within lock slot 1080, and each are located on the midline. Groove projection 1089 projects inwardly from the interior surface of ring-shaped base of coupling 1083, and is adjacent to and removed in a counterclockwise direction from coupling protrusion 1082, which projects outwardly from the from ring-shaped base of outer surface of coupling 1083. Similarly, groove projection 1090 projects inwardly from the interior surface of coupling 1083, and is adjacent to and removed in a counterclockwise direction from coupling protrusion 1085, which projects outwardly from the from ring-shaped base of outer surface of coupling 1083. For reference, control rod positioning element 1081*a/b* and attachment element 1059*a/b* are shown.

FIG. 10B shows a cross-section of lock 1020 rotated clockwise about 90 degrees to lock position 2, as shown in FIG. 3C, and system plunger 1012 is uncoupled from movement with control rod 354 (not shown), so that system plunger 1012 is now capable of moving its distal end 1065 through the interior of control rod 354 (not shown). Lock 1020 surrounds coupling 1083 which surrounds system plunger 1012. Lock slot 1079 has moved almost 90 degrees from the midline, and so has lock slot 1080. Coupling protrusion 1082, which is positioned within lock slot 1079, and coupling protrusion 1083, which is positioned within lock slot 1080, and coupling 1083 have also rotated about 90 degrees from the midline. Not shown at this level of cross-section, is that groove projection 1089, which projects from the interior surface of coupling 1083, is now positioned in groove 1087. Similarly, groove projection 1090, which projects from the interior surface of coupling 1083, is now positioned in groove 1088, which allow system plunger 1012 to advance distally through the interior of control rod 1054, while the control rod does not move (not shown).

In using a controlled delivery device, the following is an exemplary method to be used. The order of specific steps is controlled by the lock, the system plunger, the coupler and other elements of the controlled delivery device.

An aspect of a method disclosed herein may comprise pre-steps before treatment with a material. Before use of a controlled delivery device, the uterine depth of a mammalian subject may be determined, such as with an uterine sound and/or by sonography. In an aspect, a tenaculum may be used to manipulate the cervix or straighten the uterus while operating a controlled delivery device 100.

An aspect of a method disclosed herein may comprise pre-steps for assessing a controlled delivery device 100. Figure numbers refer to FIG. 1 unless otherwise noted. Testing the functioning of the balloons (end structures) 105*a* and 105*b*, of the dual lumen catheters 104*a* and 104*b* is a pre-step. A step of testing the balloon functioning comprises moving system plunger 112 from position 1 to a position proximal to position 2, or until resistance is felt due to the movement of system plunger 112, to inflate the balloons. Maintain that system plunger 112 position for a period time, e.g., 5-15 seconds, and assess the enlargement, inflation or filling of the balloons 105*a* and 105*b* and whether the inflation is maintained at the current pressure provided by that position of system plunger 112. Slowly retract system plunger 112, (move in a proximal direction), to deflate the catheter balloons.

Optionally, material cartridge 101 may be provided with an end cap (not shown) on material container outlet ports 235*a* and 235*b* (see FIG. 2). If present, the end cap is removed. Mate material cartridge 101 in cartridge receptacle 102 so that material container ends 235*a* and 235*b* mate with gaskets 461*a* and 461*b*, respectively (see FIG. 3A). Flange 127 may be moved to the uterine depth, optionally measured in a pre-step, to provide visual information to the user about the depth of insertion desired for insertion tube 111.

After pre-steps, if any, material cartridge 101 is inserted in receptacle 102 so that the material containers 103*a* and 103*b* are in fluid connection with material lumens of the catheters. See FIGS. 2A-F for material containers positioned within material cartridge 101. Inserted within material containers 203*a/b* are material cartridge plungers 240*a/b* respectively, which are positioned at the open proximal end of each material container prior to contact by material plunger actuators. See FIGS. 3A-G for illustration of contacting plungers 240 *a* and 240*b* to move the contained material from material containers 103*a* and 103*b*.

Material cartridge containers may be provided preloaded with a material to be provided to the cornua of at least one fallopian tube, or to two fallopian tubes. Material cartridge containers may contain from 0.5 mL to less than 10 mL of material.

Direction of insertion of material cartridge 101 is controlled by two indents in receptacle 102, which are located opposite of each other on lateral sides of receptacle 102 and proximally displaced from a lateral medial axis through receptacle 102. This controls the orientation of material cartridge 101 and ensures that, when inserted in receptacle 102, material container outlet ports 235*a/b* are aligned with material lumen gaskets for a fluid connection with material lumens of catheters. Additionally, material cartridge 101 is held in receptacle 102 by attachment element receptacle 150 receiving attachment element 249 on the proximal end of material cartridge 101 (see FIGS. 2A-F). Further, material cartridge 101 comprises central flange 236 on its distal end that is positioned in the distal edge of receptacle 102. Once material cartridge 101 is positioned in receptacle 102, movement of elements of device 100 is initiated.

Slider 117 is moved to the most proximal position in slot 118 to retract catheters 104*a* and 104*b* into the exit ports 119*a* and 119*b*, respectively, of insertion tube 111. The medical care provider securely holds device handle 110 in the palm of a hand with the uterine depth scale, indicator markings 126, visible, and orient controlled delivery device 100 in the horizontal or uterine plane. Level 106 should indicate the orientation of device 100, and the medical care provider maintains the level bubble between level markings 107 to ensure a horizontal orientation of device 100. While maintaining gentle traction on the cervix with a tenaculum (if used) insertion tube 111 is advanced through the cervix into the uterine cavity until flange 127 touches the external cervical os and/or fundal resistance is felt. The closed tip 124 of insertion tube 111 should be positioned at the desired fundal position and remain there for the remainder of the method until an effective amount of the contained material has been delivered to the cornua of at least one fallopian tube. If used, the tenaculum may be secured to controlled delivery device 100 by fastening tenaculum stabilizer 121 across top surface 131*a* of handle 110 and positioning the tenaculum between the tenaculum stabilizer and top surface 131*a* of handle 110 by inserting hook 122 into one of openings 123.

Slider 117 is moved from a proximal position to the most distal position in slot 118. Slider 117 is connected on its posterior surface to slide advancement lever 469 (see FIG. 4A and FIG. 3E) which is connected to and moves catheter slide connecter 470. Catheter slide connector 470 is slidably connected to the proximal end of catheter slide 471, and when catheter slide connector 470 is moved distally, it moves catheter slide 471 distally. Portions of the bodies of the catheters are retained on and around catheter slide 471, which aids in appropriate orientation of the catheters. Movement of catheter slide 471 in a distal direction moves the delivery ends (distal ends) of catheters 104 *a* and 104*b* outwardly away from exit ports 119*a* and 119*b*, respectively. Movement of slider 117 to its fullest extent in a distal direction, which moves catheter slide 471 to its most distal position, and having catheter slide 471 maintained at its most distal position by a rocker bar 391*a/b* (see FIG. 3E) and a detent located at the proximal end 470 of catheter slide 471, provides a feedback to the user, such as a click. The movement of catheter slide 470 extends the catheter ends 104*a* and 104*b* so that end structures 105*a/b*, respectively, are positioned in the uterine cornua and maintain the catheter distal ends at their controlled distance, their final position for delivery of the material.

Once the catheter ends are in place, system plunger 112 is moved from system plunger position 1, in a distal direction, to system plunger position 2, at which point, system plunger 112 cannot move any farther distally. When proximal end 130 of system plunger 112 is extended to its furthest point proximally, system plunger 112 is in system plunger position 1. System plunger 112 moving from system plunger position 1 to system plunger position 2 is only possible if lock 120 is in lock position 1. Lock position 1 is shown in FIG. 1 wherein finger lever 152*a* is visible on the lefthand side of lock opening 108*a* (looking at FIG. 1 from a proximal direction), arrow 151*a* is visible and pointing to the right. Internally, lock position 1 is shown in FIGS. 6A and 6B, where coupler protrusions 682 and 685 are positioned within lock slots 679 and 680, respectively, and lock slots 679 and 680 are aligned with the central axis line that is drawn from the system plunger through the insertion tube. Lock 620, comprising lock collar 678 and proximal end 677, substantially encircle and cover control rod 654.

The movement of system plunger 112 from system plunger position 1 to system plunger position 2 moves control rod 354 the same distance distally (see FIG. 3A-E). Control rod 354 has on its distal posterior end, two attachment elements, 359*a* and 359*b*, which are connected to and which move air syringe plungers 355*a* and 334*b* in air syringes 355*a* and 355*b*, respectively. Movement of air syringe plungers 355*a/b* pushes air (e.g., prefilled air or gas) into air lumens 357*a* and 357*b*, which causes balloons 105*a* and 105*b* to inflate. In one application of force to system plunger 112, air is moved from air cylinders, through fluid connections to air lumens and inflates ends structures, 105*a/b*, on the distal ends of catheters 104*a/b*, respectively.

Once air has been provided to the end structures of the catheters, and system plunger 112 is in system plunger position 2, lock 120 is rotated from lock position 1 to lock position 2. In lock position 1, system plunger 112 and control rod 354 are coupled in rigid system such that movement of system plunger 112 moves control rod 354, whether the movement is in a proximal to distal direction or distal to proximal direction. Once lock 120 is rotated to lock position 2, system plunger 112 and control rod 354 are uncoupled from joint movement, and system plunger 112 can move independently of control rod 354. Lock position 2 is shown internally in FIG. 8A and FIG. 8B. In FIG. 8A, arrow 851*b* is visible, and finger lever 852*a* is on the righthand side, each of which would be seen through lock opening 108*a*. FIG. 8B shows rightward rotation of lock 820's lock slot 879 to a lateral position (from its midline position) also moved coupler protrusion 882 to a lateral position, thus rotating coupler 883. Correspondingly, lock slot 880 also moved laterally, which moved coupler protrusion 885 which is positioned in lock slot 880. The lateral rotation of coupling 883 aligns the two groove projections, present on the interior surface of the ring-shaped base of coupler 883, with groove 887, seen in FIG. 8B for example, and corresponding groove 888 on the posterior side of system plunger rod (not shown). See FIGS. 10A and 10B, which illustrate groove projection positions relative to coupler protrusions, groove projection 1089 projects inwardly from the interior surface of ring-shaped base of coupling 1083, and is adjacent to and removed in a counterclockwise direction from coupling protrusion 1082, which projects outwardly from the from ring-shaped base of outer surface of coupling 1083. Similarly, groove projection 1090 projects inwardly from the interior surface of coupling 1083, and is adjacent to and removed in a counterclockwise direction from coupling protrusion 1085, which projects outwardly from the from ring-shaped base of outer surface of coupling 1083. In a cross-section, groove projection 1089, which projects from the interior surface of coupling 1083, is now positioned in groove 1087. Similarly, groove projection 1090, which projects from the interior surface of coupling 1083, is now positioned in groove 1088, which allow system plunger 1012 to advance distally through the interior of control rod 1054, while the control rod does not move (not shown).

With lock 120 in lock position 2, so that system plunger 112 can move distally while control rod 354 remains stationary, system plunger 112 is moved in a distal direction from system plunger position 2 to system plunger position 2, in which rachet teeth 967 located on the interior of control rod 954 and rachet pawl 966*a* and 966*b* located on distal end of system plunger 912 to interact, which causes distal movement to occur slowly. See FIGS. 9A and 9B. The distal movement of system plunger system plunger 112 is shown in FIG. 3D. Distal end 365 of system plunger 312 enters the proximal open end of interior of control rod 354 where proximal end 360 of material plunger control 329 is positioned. Material plunger control 329 comprises proximal end 360 and two material plunger actuators 358*s* and 358*b*. Proximal end 360 is slidably positioned in the interior of control rod 354 so that proximal end 360 is moved by distal end 365 of system plunger 312 along the lower interior surface of control rod 354, distal to the closed top portion of control rod 354. The distal ends of material plunger actuators 358*a/b* can movably contact material plungers 240*a* and 240*b* (not shown here) located within material containers (see FIG. 2) when proximal end 360 is moved in a distal direction. Material plunger actuators 358*a/b* will simultaneously move material plungers 240*a* and 240*b* (not shown), which reside inside cartridge material containers 303*a/b*. Material containers 303*a* and 303*b* are located inside material cartridge 101, but the material cartridge is not shown in FIG. 3A-3G so that interior elements and their relationships can be shown. It is assumed that material cartridge 101 (not shown) is fitted in place so that outlet ports 335a/b of material containers 303a and 303b are in fluid communication with material catheter gasket 361a and 361b which fluidly connects to material catheter lumens 362a and 362b of catheters 104a and 104b (FIG. 1), so that material contained in material containers 303a and 303b is moved from material containers 303a and 303b through outlet ports 335a/b, through material catheter gaskets 361a and 361b into material catheter lumens 362a and 362b of catheters 104a and 105b (not shown) and finally, out distal ends of catheters 104a and 105b and into the uterine cornua.

In a method of blocking conduits such as fallopian tubes of a mammal, the contained material is delivered to the cornua of the uterus at or adjacent to the opening of each fallopian tube. It is believed that an effective amount of the contained material may enter the fallopian tube and may have an effect at the cornua, and/or at the fallopian tube opening to the uterus, or within the fallopian tube. Material that may be contained by the material containers 203a and 203b include, but are not limited to, any material for treating or diagnosing uterine or fallopian tube physiology or pathology, and those disclosed in PCT/US2018/017484, which is herein incorporated in its entirety for its teaching of biopolymer compositions. After delivery of the contained material, optionally, allow for a pause of about 5-20 seconds. The tenaculum can be detached from the controlled delivery device 100 at this time by removing hook 122 from an opening 123.

Lock 120 is rotated to lock position 1 by rotating lock 120 in a counterclockwise direction, which reengages the rigid connection between lock 120 and control rod 354, returning lock and control rod elements to positions seen as described above. System plunger 112 is moved from position 3 in a proximal direction to position 2, which causes control rod 354 to move in a proximal direction, moving air syringe plungers 355a and 355b in a proximal direction. This proximal retraction of air syringe plungers 355a and 355b deflates the balloons 105A and 105b. Insertion tube 111 can then be removed from the patient. Optionally, prior to removal from the patient, both catheters may be retracted by moving slider 117 in a proximal direction so that the catheter ends are pulled into and reside within insertion tube 111. Once the catheters are retracted, insertion tube 111 is retracted from the patient.

The present disclosure comprises delivery systems, methods and devices for occluding conduits. The present disclosure comprises delivery systems and methods for occluding conduits in the body through the placement of occlusive material using a controlled delivery device disclosed herein. One aspect of the present disclosure comprises occluding conduits permanently. Another aspect of the present invention comprises methods, delivery systems and compositions to occlude at least one fallopian tube of a female mammal. Methods, systems and compositions of the present invention may be used in embodiments that permit non-surgical, office-based permanent contraception.

The present disclosure comprises delivery systems, methods and devices for delivering a composition to the cornua of one or both fallopian tubes of a mammal. The present disclosure comprises delivery systems and methods for controlled delivery to the cornua of at least one fallopian tube in the body using a controlled delivery device disclosed herein. Compositions, also referred to herein as materials, are disclosed herein.

As used herein, "occlude" refers to blocking, partially or fully, the transport of gas, fluids, or solids through a conduit. The term "occlusion," as used herein, refers to blockage within a conduit wherein such blockage results in partial restriction or complete interruption of the transport of gas, fluids, or solids through the conduit. As used herein, "occlusive material" refers to a composition that is capable of occluding a conduit by effecting an occlusion therein. As used herein, occlusive or occluding material means the initial composition that is placed or inserted into the conduit, as well as the composition, whether the physical, biological, or chemical nature of the composition has changed or not, that is in place in the conduit and provides for the interruption of flow through the conduit. The meaning of the term can be determined from its use in the sentence. Occlusive compositions, occlusion compositions, occlusive materials and occlusion materials are terms used interchangeably herein.

As used herein, occlusive material comprises any natural or synthetic compositions or any combination of natural and synthetic compositions that can be placed at the desired site in the conduit using the delivery systems of the present invention. Occlusive materials of the present invention may comprise materials that are fluid, semi-solid, gels, solids, and combinations thereof. Occlusive materials may further comprise compositions that cure in situ at the desired site in the conduit. The occlusive compositions may further comprise materials that polymerize in situ, wherein the polymerization may be initiated either at the site of interest in the conduit or prior to placement at the site. Occlusive compositions may further comprise combinations of two or more of any of the foregoing materials. Disclosed herein are exemplary compositions and materials suitable for use as occlusive compositions.

As used herein, "cure" means a change in the physical, chemical, or physical and chemical properties of the occlusive material following placement or insertion at the desired site in a conduit.

As used herein, non-invasive visualization or imaging refers to all forms of imaging that do not require the use of ionizing radiation or direct visualization such as by hysteroscopy. Examples of non-invasive imaging include all forms of ultrasound or magnetic resonance imaging, which are incorporated within the scope of this definition.

As used herein, the term "delivery system" comprises all components necessary to deliver an occlusive material or a material disclosed herein, and may comprise material to be provided, a material cartridge and a controlled delivery device such as those disclosed herein.

In general, the methods of the present invention comprise administration of delivery systems comprising a controlled delivery device that are capable of providing an occluding composition to at least one cornua of the uterus for occluding at least one fallopian tube of a female mammal. The delivery systems comprise devices that are capable of delivering occlusive compositions or other compositions to the desired site. Disclosed herein are exemplary methods, delivery systems, and compositions for occlusion of conduits of the reproductive tracts of mammals. Such methods and compositions may be used in other physiological systems and biological sites of humans or other animals, and delivery systems for such biological sites are contemplated by the present disclosure.

One aspect of the present disclosure comprises pre- and/or post-steps before use of a controlled delivery device disclosed herein. Such a pre-step or post-step includes visualization of the uterus and/or fallopian tubes, such as with sonography, before a material is delivered by a controlled delivery device, or after delivery of the material by a controlled delivery device. The present disclosure comprises post-procedure methods and compositions. Post-procedure methods may comprise, for example, ultrasound or X-ray visualization, to allow for confirmation that the occlusive material continues to provide an occlusion over time. Post-procedure methods and compositions may further comprise the use of hormonal agents to prohibit menstrual shedding of the endometrium is also contemplated to minimize the risk of expulsion for a period of time, for example to allow for a period of time for resorption of the occlusive material and tissue ingrowth. For example, use of a long-acting hormonal medication such as an injectable medroxyprogesterone acetate depot may serve the function of both the pre- and post-operative hormonal therapy without the need for reliance on patient compliance. Post-operative methods and compositions may further comprise antibiotic or steroidal compositions.

The present disclosure further comprises methods for occluding fallopian tubes for providing female sterilization. It is well known in the art that a primary cause of naturally occurring infertility in females is blockage of the oviducts from the ovary to the uterus. Females having this natural condition normally do not even realize it exists and do not suffer any adverse side effects besides being infertile. Aspects of the present disclosure comprise a delivery system, compositions comprising one or more occlusive materials, and a method for tubal occlusion and more particularly occlusion of the fallopian tubes of a female mammal for the purpose of sterilization. A resorbable occluding composition is delivered to the uterine cornua at the opening of one or both fallopian tubes. The composition flows into the fallopian tube and occludes the fallopian tube. A polymeric composition may cure in situ and be resorbed. Over time, fibrous tissue grows into the material as it resorbs, leaving an occlusion fashioned of the patient's own tissue.

It is contemplated that the methods taught herein are effective with one application of occlusive material to at least one conduit, though the methods comprise at least one application to at least one conduit. Embodiments also comprise one or more applications of occlusive material to at least one conduit during one delivery cycle. For example, once the delivery device is in place in the uterus, with at least one end of the device at the site or sites to be occluded, occlusive material may be applied once, and then, without removal, one or more other applications of occlusive material are performed. Alternatively, occlusive materials may be placed at the site or sites for occlusion over multiple treatments. For each treatment, the delivery device would be inserted and removed. Such multiple applications may occur on consecutive days of insertion and removal or the days of insertion and removal may be interspersed with days of no applications of occlusive material. Such treatment regimens may be designed with individual patient needs taken into account by those skilled in the art, such as the treating physicians. Such treatment regimens may utilize the same or different occlusive compositions at each application.

The occlusive compositions may include natural or synthetic materials. Natural materials include those found in animals or plants and not necessarily in the species in which they are used. Synthetic materials include any materials that can be made by humans or machines in laboratory or industrial settings. The compositions may comprise materials that are initially mostly fluid that polymerize in situ to become solid materials, may comprise solid materials that may or may not change properties such as flexibility, once placed at the site or sites for occlusion, may comprise a mixture of fluids with gas, solid articles or both, dispersed therein. The compositions may comprise occlusive material that starts as a liquid or semi-solid that cures in situ.

One aspect of the present disclosure comprises an occluding composition comprising a liquid that is mixed prior to delivery or does not require pre-mixing such as the single liquid composition, may or may not be ultrasound visible, and cures upon delivery into and through the tubal ostia within 5 cm of the ostium to provide mechanical blockage and is at least 75% resorbed at a range of between about 30 to about 365 days. In one embodiment, the occluding composition is not hydrophilic and does not swell in the presence of fluids in the environment. In another aspect, the occlusive composition forming the occlusion may aid in the initiation or stimulation of tissue growth into the occluded site, wherein the occlusion is replaced by tissue that maintains the occlusion after resorption of the occlusion material.

The present disclosure comprises compositions that form an occlusion in a conduit, wherein the occluding material is resorbed or biodegraded by the body in a range from at least about 20% to about 100%, or in a range from at least about 20% to about 80%, from a range of at least about 20% and about 60%, from a range of at least about 30% to about 50%, from a range of at least about 30% to about 80%, from a range of about 70% to about 100%, and from a range of about 40% to about 100%. Such resorption may occur substantially over a period of time from about 30 days to 365 days, from about 30 days to 180 days, from about 30 days to 90 days, from about 60 days to 365 days, from 60 days to 180 days, or from about 90 days to 365 days. A composition comprises a material that is resorbed or biodegraded by the body in a range of at least about 20% to substantially 100% in a period of time of about 30 days to 365 days, where the initial mechanical occlusion formed by the material is maintained thereafter by the tissue that grows into the site.

An end structure of a catheter used in a controlled delivery device may have alternative shapes that aid in maintaining the catheter end at the site, aid in delivery of occlusive or other material, aid in removal of the delivery device from the site, aid in localizing the occlusion, and other shapes and designs for functions by the end. For example, in a controlled delivery device used for occluding the fallopian tubes in a mammal, having an end that is placed within the uterine cornua at or near the tubal ostia, may have end structures that comprise a shape that aids in delivery of the occlusive or other material, for example by maintaining the material in position. This end structure may function to guide tip placement of the delivery system or anchor the arm ending to and/or cover the ostium of the tube and may take the form of a nozzle, cup, or balloon. A nozzle, cup or balloon is useful for preventing leakage of compositions of in situ curable material or other material away from the implantation site. Preferably, the end structures do not adhere to the implantable material although the use of an absorbable, detachable end structure that may adhere to the implantable material and be left in place after removal of the remainder of the delivery system is also contemplated. Using a device having a structure that conforms to the shape of the uterine cornua, maintaining localized delivery to at least one ostia eliminates the need to cannulate into the fallopian tube.

The present invention comprises methods for female sterilization wherein the delivery device is not inserted into the fallopian tube and in which the occlusive material is introduced within the uterine cornua at or near the tubal ostia affecting portions of the endometrium and/or tubal epithelium. The extent of the occlusion, such as the portion of the uterine cornua and fallopian tube blocked by the occlusive material, may be controlled by modification of the curing time, viscosity, and amount of material delivered. The current disclosure comprises methods for effective blockage of a conduit, such as a fallopian tube, by occluding a minimal portion of the fallopian tube. Such occlusion may block a conduit for less than 1.0 mm of the length of the conduit, for less than 1 cm of the length of the conduit, for less than 3 cm of the length of the conduit, or for less than 5 cm of the length of the conduit. For example, in occluding a fallopian tube, an embodiment of the present disclosure comprises methods of application of an occluding material such that no more than 5 cm of the fallopian tube is occluded. In affecting this length of tube, the anatomical areas of the fallopian tube targeted for occlusion include the areas within the uterine wall (the interstitial segment) and early portions of the isthmic section. The present invention may not be dependent on the length, width or depth of the solidified occluding material, and the extent of the solidified occluding material may be dependent on whether subsequent reversal of the occlusion is desired.

The compositions of the present invention may comprise occlusive materials or other materials which comprise one or more agents that are capable of providing other functions. The present disclosure comprises delivery systems, methods and devices for delivering one or more compositions to fallopian tubes. The present invention comprises delivery systems and methods for diagnosing or treating conduits in the body through the placement of diagnostic or therapeutic material (compositions) using a controlled delivery device. One aspect of the present disclosure comprises treating conduits. In another aspect, the present invention comprises diagnosing conduits followed by treatment. Yet another aspect of the present invention comprises methods, delivery systems and compositions to diagnose or treat the fallopian tube(s) of a female mammal, and methods and systems to treat physical structures reached by passage through the fallopian tube(s). Methods, systems and compositions of the present invention may be used in embodiments that permit non-surgical, office-based procedures.

The present disclosure comprises methods for diagnosing or treating conduits, particularly fallopian tubes found in human or other animal bodies. For example, therapeutic compositions may be provided to a fallopian tube or both fallopian tubes to enhance fertility. Therapeutic compositions comprise sperm, which can be processed or washed, hormones for fertility, fertility enhancing compounds, gametes, ova, combinations of sperm and ova, one or more zygotes, or one or more embryos, gamete and embryo deposition, ovarian stimulating compounds or gonadotropins (i.e., Follistim, Gonal-F, Repronex, Menopur, Bravelle, letrozole), ovulation induction compounds (I.e., Clomiphene citrate, such as Clomid or Serophene), oviductal glycoproteins, compounds to reduce the likelihood of implantation failure (fertilized egg) or miscarriage (i.e., granulocyte colony stimulating factor, additives from the group consisting of cytokines that suppress TH1 immune response, enhance TH2 immune response, anti-inflammatory agents, inhibitors of pro-inflammatory cytokines), hormones, fertility enhancing compounds, fertility interfering compounds, motility enhancing compounds, motility interfering compounds, compounds affecting the cilia/deciliation cycle, cilia growth enhancing or interfering compounds, ovarian follicle treatment compounds or combinations thereof.

For example, therapeutic compositions may be provided to a fallopian tube or both fallopian tubes to treat disorders, infections or cancer near, in, around, at the cornua or fimbriae exit of the tube, such as for treating ectopic pregnancy, salpingitis (i.e., pelvic inflammatory disease), tubal spasm, tubal occlusion (i.e., providing shockwaves, chemical means including solvents, biological means including enzymes, or mechanical means including stiff or cutting catheter ends), tubal obstruction, tubal obliteration (i.e., silver nitrate), tubal disease, manage tubal condition pre, during or post treatment, tubo-ovarian abscess, paratubal cysts, ovarian cysts, benign tubal tumors, benign ovarian tumors, tubal cancer, ovarian cancer, prophylactic treatment of tube or ovaries. Therapeutic compositions comprise compounds to treat ectopic pregnancies (i.e., methotrexate, PGF2a, or hypertonic glucose solution), compounds to treat fallopian tube occlusions (i.e., Ringer's lactate solution, Solu-Cortef, heparin to cleanse and maintain fallopian tube patency), compounds for pain management (i.e., lidocaine, lignocaine, bupivacaine, mepivacaine), antibiotics (i.e., Doxycycline), narcotics, medications, hydrocortisone, anti-inflammatory, antibacterial, antimicrobial, antifungal, antiviral, antimycoplasmal, or antiparisital compounds, compounds that reduce inflammation or scar tissue formation, composition comprising one or more antibiotics, antimycoplasma agents, or antiviral compounds; compositions comprising mucoproteins, electrolytes or enzymes to enhance or inhibit fertility, progesterone, estrogen, adrenergic active compounds, noradrenergic active compounds, nonsteroidal anti-inflammatory drug, prostaglandins, compounds for cancer or anti-cancer drugs (i.e., paclitaxel, cisplatin, platinum-taxane, carboplatin, cyclophosphamide, docetaxel), other compounds that may treat or prevent conditions related to the fallopian tube, uterus, ovaries, peritoneum, or other organs or coverings reached by a composition flowing from the cornua or ostia of a fallopian tube or combinations thereof.

Compositions used as described herein with devices of the present invention can be incorporated in a carrier, depot, injectable, capsule, particles, vessel, gels, fibers, or equivalent means for immediate, controlled, extended or sustained release of one or more compositions. Compositions may display a narrower therapeutic range, where controlling the release of the compound is necessary to effectively treat. For example, extending the release of a compound may be achieved through the manipulation of physiochemical properties, the use of formulation technologies such as microspheres and nanospheres, and balancing the in vivo properties of the compound (such as half-life). Post-procedure methods and compositions may further comprise the use of hormonal agents to prohibit menstrual shedding of the endometrium is also contemplated to minimize the risk of expulsion for a period of time, for example to allow for a period of time for resorption of the composition. For example, use of a long-acting hormonal medication such as an injectable medroxyprogesterone acetate depot may serve the function of both the pre- and post-operative hormonal therapy without the need for reliance on patient compliance. Post-operative methods and compositions may further comprise antibiotic or steroidal compositions.

In methods where delivery of such therapeutic or diagnostic compositions are provided by directly providing such compositions to structures, the compositions may further comprise multiple steps of delivery with delivery of a diagnostic compound initially, followed by a therapeutic composition, and the delivery of the diagnostic or therapeutic compositions may be monitored, viewed or assisted by techniques such as ultrasound. A composition comprising therapeutic agents or diagnostic compounds may be provided as one composition or may be sequentially provided in separate compositions using a delivery device of the present invention and may provide both treatment and diagnosis of the condition of a structure in one step or multiple steps of delivering the composition. Alternatively, the sole or combined therapeutic agent composition may be delivered to limit or locate the medicament in the targeted structure with or without the support of imaging allowing for treatment to occur with or without diagnosis sequentially or simultaneously.

A method of the present invention comprises delivering to a body tube, such as a fallopian tube, living cells or tissues, for example, for artificial insemination. Artificial insemination has been used in clinical medicine for more than 200 years through a variety of different techniques for the treatment of infertile couples. The original technique used for over a century was intravaginal insemination, where a semen sample was placed high in the vagina. Techniques then progressed to include intracervical insemination where semen was placed into the endocervix or endocervical canal. In the 1960s, a major breakthrough came when methods were developed for purifying sperm samples and for placement within the uterus, termed intrauterine insemination (IUI). The rationale for performing IUI is that it increases the number of motile spermatozoa at the site of fertilization by placing directly in the uterus at the time of ovulation with a catheter. Bypassing the cervix, which also acts as a reservoir and a barrier for sperm, brings the spermatozoa closer to the released oocyte. Since conception occurs in the fallopian tube, direct tubal catheterization has been utilized for injection of spermatozoa, either by laparoscopy or transvaginally by ultrasound guidance or by tactile sensation, also termed intratubal insemination. Since this method is technically challenging, it has been performed by an infertility specialist with the appropriate skill set. Another technique involves the use of intrauterine catheters or devices placed into the uterine cavity, similar to those used for hysterosalpingography, which forces the passage of sperm through the fallopian tubes once pressure has increased in the uterine cavity. Depending on the device configuration, prevention of inseminate reflux from the cervix can also be accomplished, either by a fixture on the catheter (i.e., balloon at the cervix) or specialized speculum that clamps the cervix and cervical canal. Direct passage through the fallopian tubes, bypassing possible obstacles in the fallopian tubes from membranes to mucus, of the prepared sperm increases the density of capacitated spermatozoids near the oocyte and the intraperitoneal cavity and may positively impact the pregnancy success rate. Fallopian tube sperm perfusion and intrauterine tuboperitoneal insemination are other terms used to describe the same method of filling the uterine cavity followed by passage through the interstitial part of the tubes and the ampulla, finally reaching the peritoneal cavity and pouch of Douglas, where the inseminate would be mixed with the peritoneal and follicular fluids. Results of such techniques have varied and are attributed to the wide range of different instruments used to facilitate the method. It has been reported that preventing leakage of inseminate leading to a higher fallopian sperm perfusion provides results twice as promising as standard IUI. The devices described herein allow for the effect of directed delivery of the sperm to the fallopian tube(s) but without the skill and equipment required for direct cannualization or the need to fill the entire uterine cavity to force delivery into the tubes, which will ensure that performance of the treatment can be performed by a general physician (i.e., gynecologist) as well as a specialist. In contrast to the devices that deliver sperm into the uterine cavity, the amount of sperm required by the devices described herein is considerably less as the delivery is directly to the opening of the fallopian tube(s).

A method of the present invention comprises use of a device of the present invention for delivery to a body tube for the selective delivery of ovulation stimulating hormones to induce ovulation, which is necessary for pregnancy. Therapeutic compositions to stimulate the ovaries to produce multiple eggs, include but are not limited to, follicle stimulating hormones (FSH), such as Follistim, Gonal-F, Repronex, Menopur and Bravelle, which can be given to prior to an assisted reproduction procedure, such as In Vitro Fertilization (IVF). For the treatment of ovulation dysfunction, therapeutic compositions include Clomiphene citrate, such as Clomid or Serophene, which can restore normal ovulation in about 80% of the patients whose only factor is ovulatory dysfunction. There is an increased incidence of multiple births by these methods. The devices described herein would allow for the direct delivery to and through the fallopian tube(s) to the ovaries to stimulate and induce ovulation, in a single application or in a few applications, as opposed to multiple injections. Further, providing an overall lower amount of a therapeutic compound may reduce the likelihood of ovarian hyperstimulation syndrome, a potentially life threatening complication resulting from overstimulation of the ovaries, requiring hospitalization and aggressive treatment.

A method of the present invention comprises use of a device of the present invention for delivery to a body tube for the diagnosis and treatment of an ectopic pregnancy. The incidence of ectopic pregnancy has significantly increased over the past two decades but the mortality rate has decreased, likely due to better awareness. Ectopic pregnancy results from a delay in the passage of the fertilized ovum through the fallopian tube, with the ectopic occurring in the tube located at its distal parts, particularly in the ampulla section. Diagnosis of an early ectopic pregnancy has been accomplished by determining by the rate of fluoroscopic imaging of an ampullary radiolucency upon injection of contrast material through a selective salpingography catheter. The devices described herein can achieve evaluation by allowing delivery of diagnostic compounds that are visible by fluoroscopy or sonography to one or both fallopian tubes at a time. Medical therapy may be systemic where an intramuscular dose of methotrexate is given over days or local delivery into the affected tube with a single-dose of methotrexate (or an equivalent therapeutic compound). Treatment can be at the same time or at a later time from the diagnostic evaluation. Methods that have been used to deliver methotrexate to the fallopian tube include selective salpingography under fluoroscopy, transcervical tubal catheterization/cannualization, ultrasound guided local injection, laparoscopic salpingotomy, and transvaginal injection under sonographic control. All methods were deemed feasible but those not requiring laparoscopy or operative intervention bear a lower cost as a less invasive approach. The devices described herein eliminate the need for laparoscopy or cannualization of the fallopian tube, greatly simplifying the procedure.

A method of the present invention comprises use of a device of the present invention for directed delivery to a body tube for delivery of drugs for cancer treatment of the fallopian tubes or ovaries. Fallopian tube cancer is very rare and its symptoms can resemble other problems which makes diagnosis difficult. There is evidence to suggest that the fallopian tube could be the source of ovarian cancer. Since the ovaries and tubes are closely related to each other, it is thought that these fallopian cancer cells can mimic ovarian cancer. Ovarian cancer is the second most common gynecologic cancer and the deadliest in terms of absolute numbers. In addition to local therapy and systemic chemotherapy, intraperitoneal chemotherapy is employed, where the drug is given directly into the abdomen and pelvis through a tube inserted into the abdomen. Although clinical studies have demonstrated that there is a 25 percent reduction in the risk of death with intraperitoneal treatment in comparison to the intravenous therapy group, reduced quality of life during the treatment was noted to affect the likelihood of the patient enduring all planned intraperitoneal doses. Many complications and patient discomfort/pain have been noted directly related to the access device through the abdomen and abdominal pain during infusion. In addition, to remove the intraperitoneal catheter once treatment is complete or not deemed necessary, the woman must undergo minor surgery under local anesthesia to open the previous incision down to the port, cut and remove the device. The devices described herein would allow for delivery of the drug to and through the fallopian tube to the ovaries and peritoneal cavity in a much less invasive technique and can be performed repeatedly without leaving the device in place. The methods described would provide for the effect of intraperitoneal delivery, however, transcervically by providing the drug from within the uterine cavity as opposed to the peritoneum. This will increase compliance and possibly improve outcomes.

A method of the present invention comprises use of a device of the present invention for directed delivery to a body tube for delivery of medications for tubal disease, infections, or for the management of pain. Women with the clinical diagnosis of pelvic inflammatory disease (PID) were to be evaluated by laparoscopy would usually have visual evidence of acute tubal inflammation, therefore, the clinical diagnosis of PID has been argued to represent women with visually confirmed acute salpingitis. Salpingitis is an infection and inflammation in the fallopian tubes that usually has its origin in the vagina and ascends to the fallopian tube, affecting both tubes typically by spreading of the infection via the lymph vessels. Salpingitis can lead to formation of scar tissue, which may block the tubes completely leading to infertility or partially increasing the risk of an ectopic pregnancy. Diagnosis of acute PID is usually based on clinical criteria and can be challenging for even the most astute clinicians. An approach to its diagnosis includes the need to intervene with antimicrobial therapy early on the course of this ascending infection. The CDC recommends Doxycycline be administered for treatment orally or intravenously, which when administered by these methods may lead to esophageal ulcers, gastrointestinal irritation, and local inflammation, which may lead to premature cessation of treatment. Drug delivery has successfully been accomplished transcervically with Doxycycline encapsulated in nanoparticles made of biodegradable chitosan to improve sustained delivery of the drug, minimize adverse effects and improve drug efficacy. With the devices described herein, greater emphasis of delivery to the fallopian tube(s) can be accomplished. For the management of pain, pre, during or post procedure, transcervically delivered analgesia has been found to be more effective than that administered topically, leading to quicker time to discharge and less pain.

As used herein, "diagnose" refers to evaluating with imaging the transport of gas, fluids, or solids to and through a conduit. As used herein, "diagnostic material" refers to a composition that is capable of being imaged in a conduit once delivered or during delivery. As used herein, diagnostic material means the initial composition that is placed or inserted into the conduit, as well as the composition, whether the physical, biological, or chemical nature of the composition has changed or not, that is in place in the conduit and provides for the evaluation of the conduit or flow through the conduit for evaluation. The meaning of the term can be determined from its use in the sentence. Diagnostic compositions, diagnostic compounds, and diagnostic materials are terms used interchangeably herein.

As used herein, diagnostic material comprises any synthetic or natural compositions or any combination of synthetic and natural compositions that can be placed at the desired site in the conduit using the delivery systems of the present invention. Diagnostic materials of the present invention may comprise materials that are fluid, fluid and gas, gas, semi-solid, gels, solids, and combinations thereof. The diagnostic materials may further comprise a pre-formed material that is of a shape or size that travels to the conduit. Disclosed herein are exemplary compositions and materials suitable for use as diagnostic compositions.

As used herein, "therapeutic" refers to treating without or with imaging assistance the transport of gas, fluids, or solids to and through a conduit. As used herein, "therapeutic material" refers to a composition that is capable of being imaged if imaging assistance is used in a conduit once delivered or during delivery. As used herein, therapeutic material means the initial composition that is placed or inserted into the conduit, as well as the composition, whether the physical, biological, or chemical nature of the composition has changed or not, that is in place in the conduit and provides for the treatment of the conduit or areas beyond the conduit. The meaning of the term can be determined from its use in the sentence. Therapeutic compositions, therapeutic compounds, and therapeutic materials are terms used interchangeably herein.

As used herein, therapeutic material comprises any synthetic or natural compositions or any combination of synthetic or natural compositions that can be delivered to the desired site in or around the conduit using the delivery systems of the present invention. Therapeutic materials of the present invention may comprise materials that are fluid, semi-solid, gels, solids, and combinations thereof. The therapeutic materials may further comprise a pre-formed material that is of a shape or size that travels to or out of the conduit. Therapeutic compositions may further comprise combinations of two or more of any of the therapeutic materials. Disclosed herein are exemplary compositions and materials suitable for use as therapeutic compositions.

As used herein, non-invasive visualization or imaging refers to all forms of imaging. Examples of non-invasive imaging include all forms of ultrasound, fluoroscopy, or magnetic resonance imaging, which are incorporated within the scope of this definition.

As used herein, the term "delivery system" comprises all components necessary to deliver a diagnostic or therapeutic material, using a controlled delivery device disclosed herein.

In general, the methods of the present invention comprise administration of delivery systems that deliver compositions that are capable of diagnosing or treating conduits. The delivery systems comprise devices that are capable of delivering diagnostic or therapeutic compositions to the desired site. Disclosed herein are exemplary methods, delivery systems, and compositions for diagnosis or treatment of conduits of the reproductive tracts of mammals. Such methods and compositions can be used in other physiological systems and biological sites of humans or other animals, and delivery systems for such biological sites are contemplated by the present invention.

In an aspect, the disclosed method can comprise diagnosing at least a portion of one or two conduits. In an aspect, one conduit can be diagnosed. In an aspect, two conduits can be diagnosed. In an aspect, diagnosing at least a portion of one or two conduits can comprise delivering an effective amount of the composition comprising a diagnostic material such that the material enters the lumen of the one or two conduits. In an aspect, the disclosed method can comprise treating at least a portion of one or two conduits. In an aspect, one conduit can be treated. In an aspect, two conduits can be treated. In an aspect, the method can comprise diagnosing at least one conduit following the treating of at least one conduit. In an aspect, one of the conduits can be a fallopian tube of a mammal. In an aspect, two of the conduits can be a fallopian tube of a mammal.

In an aspect of a method for diagnosing and treating at least a portion of one or two conduits in a human or animal body, delivering an effective amount of a composition comprising a diagnostic material and delivering an effective amount of a composition comprising a therapeutic material.

In an aspect of a method for diagnosing and treating at least a portion of one or two conduits in a human or animal body, delivering an effective amount of a composition comprising a diagnostic material and delivering an effective amount of a composition comprising a therapeutic material can occur sequentially or can occur simultaneously.

In an aspect of a method for diagnosing and treating at least a portion of one or two conduits in a human or animal body, a composition comprising a diagnostic material and the composition comprising a therapeutic material can be the same composition or can be different compositions.

In an aspect of a method for diagnosing and treating at least a portion of one or two conduits in a human or animal body, the introducer shaft can have one exit port and one catheter, and one or more compositions can be provided into and through the one catheter.

A method of the present invention comprises use of devices disclosed herein is to deliver an effective amount of one or more compositions disclosed herein to a body structure such as a fallopian tube by delivery of one or more compositions to the uterine cornua near the tubal ostia.

Disclosed herein is a method for treating cancer, comprising, (a) providing a delivery system that delivers an effective amount of a composition comprising an anti-cancer or chemotherapeutic material, wherein the delivery system comprises a delivery device comprising an introducer shaft comprising one or two exit ports for providing one or two catheters, one or two catheters each comprising an end structure on a delivery end, a composition comprising an anti-cancer or chemotherapeutic material, and a means for providing the composition comprising an anti-cancer or chemotherapeutic material into and through the one or two catheters; (b) delivering an effective amount of the composition comprising an anti-cancer or a chemotherapeutic material at or near a target site such that the anti-cancer or chemotherapeutic material contacts at least one fallopian tube, at least one ovary, the peritoneum, or a combination thereof.

In an aspect, the anti-cancer or chemotherapeutic material can comprise paclitaxel, cisplatin, platinum-taxane, carboplatin, cyclophosphamide, or docetaxel. In an aspect, the anti-cancer or chemotherapeutic material can comprise an anti-cancer or chemotherapeutic material known to the art.

Disclosed herein are biodegradable cyanoacrylate compositions comprising three components; 1) a cyanoacrylate component; 2) a stabilizer component and 3) a polymerization inhibitor component. In an aspect, a composition may comprise, a) at least about 80 wt % (weight percent) or higher of the cyanoacrylate component; b) from about 500 ppm to about 1,500 ppm of the stabilizer component; and c) from about 4,000 ppm to about 7,000 ppm of the polymerization inhibitor component, wherein the cyanoacrylate component may comprise one or more cyanoacryalates. Such biodegradable cyanoacrylate compositions may be sterile compositions. It is understood that the compositions disclosed herein are formulated as liquid compositions and that after the liquid composition is provided to a target site, such as the cornua of a uterus near the tubal ostia, the liquid composition undergoes polymerization and forms a solid material that is the result of the reactions of the components in the liquid formulation. Further, as the disclosed compositions are biodegradable (also known as absorbable or resorbable compositions), the solid material is transformed over time into its breakdown products. It will be clear to those of skill in the art in the disclosure herein where the liquid formulation is intended, where the polymerized material is intended and where the break down products are intended.

Disclosed herein are biodegradable cyanoacrylate compositions consisting essentially of three components; 1) a cyanoacrylate component; 2) a stabilizer component and 3) a polymerization inhibitor component. In an aspect, a composition may consist essentially of, a) about 90 weight percent or higher of the cyanoacrylate component; b) from about 500 ppm to about 1,500 ppm of the stabilizer component; and c) from about 4,000 ppm to about 7,000 ppm of the polymerization inhibitor component, wherein the cyanoacrylate component may comprise one or more cyanoacrylates. Such biodegradable cyanoacrylate compositions may be sterile compositions.

In an aspect, a biodegradable cyanoacrylate composition can comprise: a) about 80.0 wt %, 80.5 wt %, 81 wt %, 81.5 wt %, 82 wt %; 82.5 wt %; 83 wt %; 83.5 wt %; 84 wt %; 84.5 wt %, 86 wt %; 86.5 wt %; 87 wt %; 87.5% wt %, 88 wt %; 88.5 wt %, 89 wt %, 89.5 wt %, 90 wt %, 90.5 wt %, 91 wt %, 91.5 wt %, 92 wt %; 92.5 wt %; 93 wt %; 93.5 wt %; 94 wt %; 94.5 wt %, 96 wt %; 96.5 wt %; 97 wt %; 97.5 wt %, 98 wt %; 98.5 wt %, 99 wt %, 99.5 wt %, 99.9 wt % or in a range from 80 to 99.9 wt %, 80 to 95 wt %, 80 to 81 wt %, 80 to 82 wt %, 80 to 85 wt %, 84 to 86 wt %, 85 to 87 wt %, 86 to 88 wt %, 87 to 89 wt %, 88 to 90 wt %, 90 to 92 wt %, 91 to 93 wt %, 90.5 to 92.5 wt %, 91 to 93 wt %, 92 to 94 wt %, 93 to 95 wt %, 95.5 to 97.5 wt %, 94 to 96 wt %, 95 to 98 wt %, 96 to 99 wt %, 90 to 97 wt %, 90 to 95 wt % and 90 to 99.9 wt % of the cyanoacrylate component; b) about 500 ppm to about 550 ppm; 500 ppm to about 600 ppm; about 500 ppm to about 650 ppm; about 500 ppm to about 700 ppm; about 500 ppm to about 750 ppm; about 500 ppm to about 800 ppm; about 500 ppm to about 850 ppm; about 500 ppm to about 900 ppm; about 500 ppm to about 950 ppm; about 500 ppm to about 1000 ppm; about 500 ppm to about 1100 ppm; about 500 ppm to about 1200 ppm; about 500 ppm to about 1300 ppm; about 500 ppm to about 1400 ppm; or about 500 ppm to about 1500 ppm of the stabilizer component; and c) about 4,000 ppm to about 4,500 ppm; 4,000 ppm to about 5,000 ppm; about 4,000 ppm to about 5,500 ppm; about 4,000 ppm to about 6,000 ppm; about 4,000 ppm to about 6,500 ppm; about 4,000 ppm to about 6,500 ppm; or about 4,000 ppm to about 7,000 ppm of the polymerization inhibitor component.

In an aspect, a biodegradable cyanoacrylate composition can comprise: a) about 80.0 wt %, 80.5 wt %, 81 wt %, 81.5 wt %, 82 wt %; 82.5 wt %; 83 wt %; 83.5 wt %; 84 wt %; 84.5 wt %, 86 wt %; 86.5 wt %; 87 wt %; 87.5% wt %, 88 wt %; 88.5 wt %, 89 wt %, 89.5 wt %, 90 wt %, 90.5 wt %, 91 wt %, 91.5 wt %, 92 wt %; 92.5 wt %; 93 wt %; 93.5 wt %; 94 wt %; 94.5 wt %, 96 wt %; 96.5 wt %; 97 wt %; 97.5 wt %, 98 wt %; 98.5 wt %, 99 wt %, 99.5 wt %, 99.9 wt % or in a range from 80 to 99.9 wt %, 80 to 95 wt %, 80 to 81 wt %, 80 to 82 wt %, 80 to 85 wt %, 84 to 86 wt %, 85 to 87 wt %, 86 to 88 wt %, 87 to 89 wt %, 88 to 90 wt %, 90 to 92 wt %, 91 to 93 wt %, 90.5 to 92.5 wt %, 91 to 93 wt %, 92 to 94 wt %, 93 to 95 wt %, 95.5 to 97.5 wt %, 94 to 96 wt %, 95 to 98 wt %, 96 to 99 wt %, 90 to 97 wt %, 90 to 95 wt % and 90 to 99.9 wt % of the cyanoacrylate component; b) about 1400 ppm to about 1500 ppm; about 1300 ppm to about 1500 ppm; about 1200 ppm to about 1500 ppm; about 1100 ppm to about 1500 ppm; about 1000 ppm to about 1500 ppm; about 900 ppm to about 1500 ppm; about 800 ppm to about 1500 ppm; about 700 ppm to about 1500 ppm; or about 600 ppm to about 1500 ppm of the stabilizer component; and c) about 4,000 ppm to about 4,500 ppm; 4,000 ppm to about 5,000 ppm; about 4,000 ppm to about 5,500 ppm; about 4,000 ppm to about 6,000 ppm; about 4,000 ppm to about 6,500 ppm; about 4,000 ppm to about 6,500 ppm; or about 4,000 ppm to about 7,000 ppm of the polymerization inhibitor component.

In an aspect, biodegradable cyanoacrylate cyanoacrylate compositions can comprise: a) about 80.0 wt %, 80.5 wt %, 81 wt %, 81.5 wt %, 82 wt %; 82.5 wt %; 83 wt %; 83.5 wt %; 84 wt %; 84.5 wt %, 86 wt %; 86.5 wt %; 87 wt %; 87.5 wt %, 88 wt %; 88.5 wt %, 89 wt %, 89.5 wt %, 90 wt %, 90.5 wt %, 91 wt %, 91.5 wt %, 92 wt %; 92.5 wt %; 93 wt %; 93.5 wt %; 94 wt %; 94.5 wt %, 96 wt %; 96.5 wt %; 97 wt %; 97.5 wt %, 98 wt %; 98.5 wt %, 99 wt %, 99.5 wt %, or in a range from 80 to 99.5 wt %, 80 to 95 wt %, 80 to 81 wt %, 80 to 82 wt %, 80 to 85 wt %, 84 to 86 wt %, 85 to 87 wt %, 86 to 88 wt %, 87 to 89 wt %, 88 to 90 wt %, 90 to 92 wt %, 91 to 93 wt %, 90.5 to 92.5 wt %, 91 to 93 wt %, 92 to 94 wt %, 93 to 95 wt %, 95.5 to 97.5 wt %, 94 to 96 wt %, 95 to 98 wt %, 96 to 99 wt %, 90 to 97 wt %, 90 to 95 wt % and 90 to 99.9 wt % of the cyanoacrylate component; b) about 500 ppm to about 550 ppm; 500 ppm to about 600 ppm; about 500 ppm to about 650 ppm; about 500 ppm to about 700 ppm; about 500 ppm to about 750 ppm; about 500 ppm to about 800 ppm; about 500 ppm to about 850 ppm; about 500 ppm to about 900 ppm; about 500 ppm to about 950 ppm; about 500 ppm to about 1000 ppm; about 500 ppm to about 1100 ppm; about 500 ppm to about 1200 ppm; about 500 ppm to about 1300 ppm; about 500 ppm to about 1400 ppm; or about 500 ppm to about 1500 ppm of the stabilizer component; and c) about 4,500 ppm to about 7,000 ppm; about 5,000 ppm to about 7,000 ppm; or about 6,500 ppm to about 7,000 ppm of the polymerization inhibitor component.

In an aspect, biodegradable cyanoacrylate compositions can comprise a) about 80.0 wt %, 80.5 wt %, 81 wt %, 81.5 wt %, 82 wt %; 82.5 wt %; 83 wt %; 83.5 wt %; 84 wt %; 84.5 wt %, 86 wt %; 86.5 wt %; 87 wt %; 87.5% wt %, 88 wt %; 88.5 wt %, 89 wt %, 89.5 wt %, 90 wt %, 90.5 wt %, 91 wt %, 91.5 wt %, 92 wt %; 92.5 wt %; 93 wt %; 93.5 wt %; 94 wt %; 94.5 wt %, 96 wt %; 96.5 wt %; 97 wt %; 97.5 wt %, 98 wt %; 98.5 wt %, 99 wt %, 99.5 wt %, 99.9 wt % or in a range from 80 to 99.9 wt %, 80 to 95 wt %, 80 to 81 wt %, 80 to 82 wt %, 80 to 85 wt %, 84 to 86 wt %, 85 to 87 wt %, 86 to 88 wt %, 87 to 89 wt %, 88 to 90 wt %, 90 to 92 wt %, 91 to 93 wt %, 90.5 to 92.5 wt %, 91 to 93 wt %, 92 to 94 wt %, 93 to 95 wt %, 95.5 to 97.5 wt %, 94 to 96 wt %, 95 to 98 wt %, 96 to 99 wt %, 90 to 97 wt %, 90 to 95 wt % and 90 to 99.9 wt % of the cyanoacrylate component; b) about 1400 ppm to about 1500 ppm; about 1300 ppm to about 1500 ppm; about 1200 ppm to about 1500 ppm; about 1100 ppm to about 1500 ppm; about 1000 ppm to about 1500 ppm; about 900 ppm to about 1500 ppm; about 800 ppm to about 1500 ppm; about 700 ppm to about 1500 ppm; or about 600 ppm to about 1500 ppm of the stabilizer component; and c) about 4,500 ppm to about 7,000 ppm; about 5,000 ppm to about 7,000 ppm; or about 6,500 ppm to about 7,000 ppm of polymerization inhibitor component.

In an aspect, biodegradable cyanoacrylate compositions can comprise a) about 80.0 wt %, 80.5 wt %, 81 wt %, 81.5 wt %, 82 wt %; 82.5 wt %; 83 wt %; 83.5 wt %; 84 wt %; 84.5 wt %, 86 wt %; 86.5 wt %; 87 wt %; 87.5% wt %, 88 wt %; 88.5 wt %, 89 wt %, 89.5 wt %, 90 wt %, 90.5 wt %, 91 wt %, 91.5 wt %, 92 wt %; 92.5 wt %; 93 wt %; 93.5 wt %; 94 wt %; 94.5 wt %, 96 wt %; 96.5 wt %; 97 wt %; 97.5 wt %, 98 wt %; 98.5 wt %, 99 wt %, 99.5 wt %, 99.9 wt % or in a range from 80 to 99.9 wt %, 80 to 95 wt %, 80 to 81 wt %, 80 to 82 wt %, 80 to 85 wt %, 84 to 86 wt %, 85 to 87 wt %, 86 to 88 wt %, 87 to 89 wt %, 88 to 90 wt %, 90 to 92 wt %, 91 to 93 wt %, 90.5 to 92.5 wt %, 91 to 93 wt %, 92 to 94 wt %, 93 to 95 wt %, 95.5 to 97.5 wt %, 94 to 96 wt %, 95 to 98 wt %, 96 to 99 wt %, 90 to 97 wt %, 90 to 95 wt % and 90 to 99.9 wt % of the cyanoacrylate component; b) about 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, 1,000 ppm, 1,025 ppm, 1,050 ppm, 1,075 ppm, 1,100 ppm, 1,125 ppm, 1,150 ppm, 1,175 ppm, 1,200 ppm, 1,225 ppm, 1,250 ppm, 1,275 ppm, 1,300 ppm, 1,325 ppm, 1,350 ppm, 1,375 ppm, 1,400 ppm, 1,425 ppm, 1,450 ppm, 1,475 ppm, or 1,500 ppm of the stabilizer component; and c) about 4,000 ppm, 4,250 ppm, 4,500 ppm, 4,750 ppm, 5,000 ppm, 5,250 ppm, 5,500 ppm, 5,750 ppm, 6,000 ppm, 6,250 ppm, 6,500 ppm, 6,750 ppm, or 7,000 ppm of polymerization inhibitor component.

A disclosed biodegradable cyanoacrylate composition may be referred to herein interchangeably as a cyanoacrylate composition or an occlusive composition.

A disclosed biodegradable cyanoacrylate composition may comprise at least these disclosed components, a cyanoacrylate component, a polymerization inhibitor, and a stabilizer, in combinations that affect the desired characteristics of a cyanoacrylate composition itself, the delivery of the composition, or the material formed after curing (polymerization) of the composition. Differing cyanoacrylate monomers or differing amounts of each may be included in a biodegradable cyanoacrylate composition for the following purposes, among others: to modulate charge morphology; alter physical properties of the cyanoacrylate composition, including, but not limited to, molecular weight or viscosity; alter the interaction of the cyanoacrylate composition with certain additives and other materials, such as polymers, plastics and metals; alter tissue reaction or response to the applied composition; adjust adhesion properties of the composition, including, but not limited to, polymerization rate or heat of polymerization; adjust the degradation profile of the resultant composition, including percent degradation, degradation rate, and formaldehyde production during degradation; alter physical properties of the applied cured composition, including, but not limited to, bond strength, pliability, granularity, and cohesivity.

In an aspect a biodegradable cyanoacrylate component comprises one or more types of cyanoacrylate monomers, for example monomeric esters of 2-cyanoacrylic acid of the general formula:

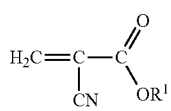

wherein R$^1$ is a hydrocarbyl or substituted hydrocarbyl group; a group having the formula:

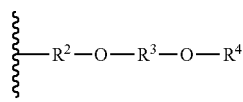

wherein R$^2$ is a 1,2-alkylene group having 2-4 carbon atoms, R$^3$ is an alkylene group having 2-12 carbon atoms, and R$^4$ is an alkyl group having 1-6 carbon atoms; or a group having the formula:

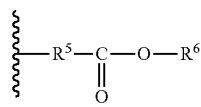

wherein R$^5$ has a formula:

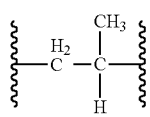

or —[C(CH$_3$)$_2$]n-, wherein n is an integer with a value of 1, 2, 3, 4, 5, 6, 7, 8, 9, 10, 11, 12, 13, or 14 and R$^6$ is an organic moiety.

In various aspects, the hydrocarbyl and substituted hydrocarbyl groups can be a straight chain or branched chain alkyl group having 1-16 carbon atoms; a straight chain or branched chain C1-C6 alkyl group substituted with an acyloxy group, a haloalkyl group, an alkoxy group, an alkyloxy group, a halogen atom, a cyano group, or a haloalkyl group; a straight chain or branched chain alkenyl group having 2 to 16 carbon atoms; a straight chain or branched chain alkynyl group having 2 to 12 carbon atoms cycloalkyl groups; an arylalkyl group; an alkylaryl group; and an aryl group. In a further aspect, the hydrocarbyl and substituted hydrocarbyl groups can be an alkyl group having 1 to 10 carbon atoms optionally substituted with a C1-C6 alkoxy group; an alkenyl group having 2 to 10 carbon atoms optionally substituted with a C1-C6 alkoxy group; a cyclohexyl group optionally substituted with a C1-C6 alkoxy group; or a phenyl group optionally substituted with a C1-C6 alkoxy group.

In an aspect, R1 is selected from methyl, ethyl, n-propyl, isopropyl, n-butyl, isobutyl, pentyl, neo-pentyl, hexyl, n-octyl, 2-octyl, methoxymethyl, methoxyethyl, methoxypropyl, methoxyisopropyl, methoxybutyl, methoxyisobutyl, allyl, methallyl, crotyl, propargyl, cyclohexyl, benzyl, phenyl, cresyl, 2-chlorobutyl, trifluorethyl, 2-methoxyethyl, 3-methoxybutyl, 2-ethoxyethyl, and 2-propoxyethyl.

The organic moiety R6 can be substituted or unsubstituted and can be a straight chain, branched or cyclic, saturated, unsaturated or aromatic. In a further aspect, such organic moieties include C1-C8 alkyl moieties, C2-C8 alkenyl moieties, C2-C8 alkynyl moieties, C3-C12 cycloaliphatic moieties, aryl moieties such as phenyl and substituted phenyl, and arylalkyl moieties such as benzyl, methylbenzyl and phenylethyl. Other organic moieties include substituted hydrocarbon moieties, such as halo (e.g., chloro-, fluoro- and bromo-substituted hydrocarbons) and oxy—(e.g., alkoxy substituted hydrocarbons) substituted hydrocarbon moieties. In a still further aspect, R6 can be an alkyl, alkenyl or alkynyl moieties having from 1 to about 8 carbon atoms, and halo-substituted derivatives thereof. In a yet further aspect, R6 can be an alkyl moiety of 4 to 8 carbon atoms.

In various aspects, R1 is an alkyl group having 1-10 carbon atoms or a group having the formula—AOR7, wherein A is a divalent straight or branched chain alkylene or oxyalkylene moiety having 2-8 carbon atoms, and R7 is a straight or branched alkyl moiety having 1-8 carbon atoms. In a further aspect, a cyanoacrylate component is 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate, methyl cyanoacrylate, ethyl cyanoacrylate, propyl cyanoacrylate, butyl cyanoacrylate, pentyl cyanoacrylate, hexyl cyanoacrylate, septyl cyanoacrylate, octyl nonyl cyanoacrylate, decyl 2-cyanoacrylate, allyl cyanoacrylate, methoxyethyl cyanoacrylate, methoxyisopropyl cyanoacrylate, methoxypropyl cyanoacrylate, methoxybutyl cyanoacrylate, or methoxypentyl cyanoacrylate, or a combination thereof. A cyanoacrylate component may comprise two or more methoxy cyanoacrylate monomers.

Cyanoacrylate monomers disclosed herein can be prepared by methods known in the art. For example, see U.S. Pat. Nos. 2,721,858, 3,254,111, 3,995,641 and 4,364,876, each of which is hereby incorporated in its entirety by reference, for example, for cyanoacrylate synthesis. Cyanoacrylate monomers for use in the present disclosure include aliphatic 2-cyanoacrylate esters, including, but not limited to, an alkyl, cycloalkyl, halogenated, alkenyl or alkoxyalkyl 2-cyanoacrylate. The alkyl group may have from 1-16 carbon atoms, 2-8 carbon atoms, or 1-4 carbon atoms. Suitable esters include the methyl, ethyl, n-propyl, isopropyl, isobutyl, n-butyl, sec-butyl, n-pentyl, isopentyl, n-hexyl, isohexyl, 2-ethylhexyl, cyclohexyl, n-heptyl, n-octyl, 2-octyl, 2-methoxyethyl, methoxypropyl, 2-ethoxyethyl, and 2-methoxyisopropyl esters of cyanoacrylic acid and the like. For use in medical or in vivo applications, monomers utilized are of high purity.

For example, a cyanoacrylate component may comprise a) about 80.0 wt %, 80.5 wt %, 81 wt %, 81.5 wt %, 82 wt %; 82.5 wt %; 83 wt %; 83.5 wt %; 84 wt %; 84.5 wt %, 86 wt %; 86.5 wt %; 87 wt %; 87.5 wt %, 88 wt %; 88.5 wt %, 89 wt %, 89.5 wt %, 90 wt %, 90.5 wt %, 91 wt %, 91.5 wt %, 92 wt %; 92.5 wt %; 93 wt %; 93.5 wt %; 94 wt %; 94.5 wt %, 96 wt %; 96.5 wt %; 97 wt %; 97.5 wt %, 98 wt %; 98.5 wt %, 99 wt %, 99.5 wt %, or in a range from 80 to 99.5 wt %, 80 to 95 wt %, 80 to 81 wt %, 80 to 82 wt %, 80 to 85 wt %, 84 to 86 wt %, 85 to 87 wt %, 86 to 88 wt %, 87 to 89 wt %, 88 to 90 wt %, 90 to 92 wt %, 91 to 93 wt %, 90.5 to 92.5 wt %, 91 to 93 wt %, 92 to 94 wt %, 93 to 95 wt %, 95.5 to 97.5 wt %, 94 to 96 wt %, 95 to 98 wt %, 96 to 99 wt %, 90 to 97 wt %, 90 to 95 wt % and 90 to 99.9 wt % of the cyanoacrylate component, may comprise up to about 100 wt % of the composition and all ranges therebetween 80 wt % and 100 wt %.

In an aspect, a cyanoacrylate component comprises a blend or admixture of two or more cyanoacrylate monomers in the wt % and/or ranges disclosed herein. For example, if one cyanoacrylate monomer is methyl cyanoacrylate and a second cyanoacrylate monomer is ethyl cyanoacrylate, a blend or admixture of the methyl cyanoacrylate monomer and the ethyl cyanoacrylate monomer could form a cyanoacrylate component such as those disclosed herein. In an aspect, a cyanoacrylate component comprises a single cyanoacrylate monomers in the wt % and/or ranges disclosed herein. For example, if one cyanoacrylate monomer is methyl cyanoacrylate, the methyl cyanoacrylate monomer forms a cyanoacrylate component such as those disclosed herein.

In an aspect, a stabilizer component of a cyanoacrylate composition is an anionic stabilizer. Examples of stabilizer components include, but are not limited to, the following: alkyl sulfides, alkyl sulfates, alkyl sulfonyls, alkyl sulfones, alkyl sulfoxides, alkyl sulfites, sultones (e.g., a-chloro-a-hydroxy-o-toluenesulfonic acid-y-sultone), sulfur dioxide, sulfur trioxide, sulfonic acid, lactone, boron trifluoride, organic acids, such as acetic acid, 3-sulfolene, mercaptan, and the like, and mixtures thereof. In certain applications, the stabilizer component is one or more of sulfur dioxide, sulfur trioxide, or sulfonic acid, or combinations thereof.

In an aspect, a cyanoacrylate composition can comprise an acidic stabilizing agent such as hydrogen sulfide, carbonic acid, triacetylmethane, acetic acid, lactic acid, benzoic acid, dinitrophenol, formic acid, nitrous acid, hydrochloric acid, hydrobromic acid, hydrofluoric acid, chloroacetic acid, phosphoric acid (including ortho, meta, or para-phosphoric acid), dichloroacetic acid, trichloroacetic acid, trinitrophenol (picric acid), trifluoroacetic acid, sulfuric acid, perchloric acid, toluenesulfonic acid, fluorosulfonic acid, and the like, and mixtures thereof, can be included in the cyanoacrylate composition.

A biodegradable cyanoacrylate composition may have one or more types of stabilizing agents, such as an anionic stabilizer and an acidic stabilizer.

A stabilizer component can be present at a concentration of about 500 to about 1,500 parts per million stabilizer component. In an aspect, a stabilizer component is present in an amount of about 500 ppm to about 550 ppm; 500 ppm to about 600 ppm; about 500 ppm to about 650 ppm; about 500 ppm to about 700 ppm; about 500 ppm to about 750 ppm; about 500 ppm to about 800 ppm; about 500 ppm to about 850 ppm; about 500 ppm to about 900 ppm; about 500 ppm to about 950 ppm; about 500 ppm to about 1000 ppm; about 500 ppm to about 1100 ppm; about 500 ppm to about 1200 ppm; about 500 ppm to about 1300 ppm; about 500 ppm to about 1400 ppm; or about 500 ppm to about 1500 ppm. In an aspect, the stabilizer component is present in an amount of about 1400 ppm to about 1500 ppm; about 1300 ppm to about 1500 ppm; about 1200 ppm to about 1500 ppm; about 1100 ppm to about 1500 ppm; about 1000 ppm to about 1500 ppm; about 900 ppm to about 1500 ppm; about 800 ppm to about 1500 ppm; about 700 ppm to about 1500 ppm; or about 600 ppm to about 1500 ppm. In an aspect, the stabilizer component is present in an amount greater than about 500 ppm; greater than about 550 pm; or greater than about 600 ppm. The stabilizer component can be present in an amount of about 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, 1,000 ppm, 1,025 ppm, 1,050 ppm, 1,075 ppm, 1,100 ppm, 1,125 ppm, 1,150 ppm, 1,175 ppm, 1,200 ppm, 1,225 ppm, 1,250 ppm, 1,275 ppm, 1,300 ppm, 1,325 ppm, 1,350 ppm, 1,375 ppm, 1,400 ppm, 1,425 ppm, 1,450 ppm, 1,475 ppm, or 1,500 ppm.

In an aspect, a polymerization inhibitor component of a cyanoacrylate composition is a free radical stabilizer. Agents suitable for use as the polymerization inhibitor component include butylated hydroxy anisole (BHA); NMP (n-methyl-pyrrolidone), hydroquinone; catechol; hydroquinone monomethyl ether and hindered phenols such as butylated hydroxyanisol; 4-ethoxyphenol; butylated hydroxytoluene (BHT, 2,6-di-tert-butyl butylphenol), 4-methoxyphenol (MP); 3-methoxyphenol; 2-tert-butyl-4-methoxyphenol; and 2,2-methylene-bis-(4-methyl-6-tert-butylphenol), and the like, and mixtures thereof. In certain applications, the polymerization inhibitor component is BHA or BHT.

A polymerization inhibitor component can be present in an amount from about 4,000 ppm to about 7,000 ppm. In an aspect, a polymerization inhibitor component is present in an amount of about 4,000 ppm to about 4,500 ppm; 4,000 ppm to about 5,000 ppm; about 4,000 ppm to about 5,500 ppm; about 4,000 ppm to about 6,000 ppm; about 4,000 ppm to about 6,500 ppm; about 4,000 ppm to about 6,500 ppm; or about 4,000 ppm to about 7,000 ppm. In an aspect, a polymerization inhibitor component is present in an amount of about 4,500 ppm to about 7,000 ppm; about 5,000 ppm to about 7,000 ppm; or about 6,500 ppm to about 7,000 ppm. In an aspect, a polymerization inhibitor component is present in an amount greater than about 4,000 ppm; greater than about 4,500 pm; or greater than about 5,000 ppm. A polymerization inhibitor component can be present in an amount of about 4,000 ppm, 4,250 ppm, 4,500 ppm, 4,750 ppm, 5,000 ppm, 5,250 ppm, 5,500 ppm, 5,750 ppm, 6,000 ppm, 6,250 ppm, 6,500 ppm, 6,750 ppm, or 7,000 ppm.

A biodegradable cyanoacrylate composition contemplated by the current disclosure may comprise additives necessary to impart the desired properties, including viscosity, color, X-ray opacity, and others. For example, compositions of the present disclosure may include at least one plasticizing agent that imparts flexibility to the delivered polymerized material. A plasticizing agent(s) preferably contain little or no moisture and should not significantly affect the polymerization of the composition. Suitable plasticizers are known in the art and include those disclosed in U.S. Pat. Nos. 2,784,127 and 4,444,933, the disclosures of which are incorporated herein by reference in their entirety. Examples of suitable plasticizers include, but are not limited to, tributyl citrate (TBC), acetyl tributyl citrate (ATBC), dimethyl sebacate, triethyl phosphate, tri(2-ethylhexyl) phosphate, tri(p-cresyl) phosphate, glyceryl triacetate, glyceryl tributyrate, diethyl sebacate, diisodecyl adipate (DIDA), dioctyl adipate (DICA), isopropyl myristate, butyl stearate, lauric acid, trioctyl trimellitate, dioctyl glutarate (DICG), dioctyl phthalate, acetyl tri-n-butyl citrate, and the like, and mixtures thereof. In an aspect, suitable plasticizers may include polymeric plasticizers, such as polyethylene glycol (PEG) esters and capped PEG esters or ethers, polyester glutarates and polyester adipates. In an aspect, a plasticizer can be butyl benzyl phthalate, dibutyl phthalate, diethyl phthalate, dimethyl phthalate, dioctylphthalate, trialkyl acylcitrates, benzoate esters of di- and poly-hydroxy branched aliphatic compounds, tri(p-cresyl) phosphate, combinations thereof and the like. In an aspect, plasticizers can be acyl trialkyl citrates independently having from 1 to 10 carbon atoms in each alkyl group. For example, acyl trialkyl acylcitrates can be trimethyl O-acetylcitrate, triethyl O-acetylcitrate, tri-n-propyl O-acetylcitrate, tri-n-butyl O-acetylcitrate, tri-n-pentyl O-acetylcitrate, tri-n-hexyl O-acetylcitrate, tri-methyl O-propionylcitrate, tri-ethyl O-propionylcitrate, tri-n-propyl O-propionylcitrate, tri-n-butyl O-propionylcitrate, tri-n-pentyl O-propionylcitrate, tri-n-hexyl O-propionylcitrate, tri-methyl O-butyrylcitrate, tri-ethyl O-butyrylcitrate, tri-n-propyl O-butyrylcitrate, tri-n-butyl O-butyrylcitrate, tri-n-pentyl O-butyrylcitrate, tri-n-hexyl O-butyrylcitrate, and the like. In an aspect, the plasticizer can tri-n-butyl O-acetylcitrate. In an aspect, tributyl citrate, diisodecyl adipate and acetyl tributyl citrate, which when present are in an amount of up to thirty percent (30%) by weight of the liquid adhesive composition. The amount to be used can be determined by one of ordinary skills in the art, using known techniques without undue experimentation.

Compositions of the present disclosure may include at least one biocompatible agent effective in reducing active formaldehyde concentration levels during degradation (for compositions subject to in vivo degradation; such compounds are referred to as "formaldehyde concentration reducing agents"). Examples of formaldehyde scavenger compounds useful in this disclosure include, but are not limited to, the following: sulfites, bisulfites, ammonium sulfite salts, amines, amides, imides, nitriles, carbamates, alcohols; mercaptans, proteins, active methylene compounds such as cyclic ketones and compounds having a b-dicarbonyl group, certain heterocyclic ring compounds, and the like, and mixtures thereof. Bisulfites and sulfites useful as the formaldehyde scavenger include alkali metal salts and ammonium salts. Examples of useful amines include the aliphatic and aromatic amines, such as aniline, benzidine, aminopyrimidine, toluene-di amine, triethylenediamine, diphenylamine, diaminodiphenylamine, hydrazines, hydrazide, and the like, and mixtures thereof. Suitable proteins include collagen, gelatin, casein, soybean protein, vegetable protein, keratin, glue, and the like, and mixtures thereof. Suitable amides include urea, cyanamide, acrylamide, benzamide, and acetamide. Suitable alcohols include phenols, 1,4-butanediol, d-sorbitol, and polyvinyl alcohol. Examples of suitable compounds having a b-dicarbonyl group include malonic acid, acetylacetone, ethylacetone, acetate, malonamide, diethylmalonate, or another malonic ester and the like, and mixtures thereof.

Biodegradable cyanoacrylate compositions of the present disclosure may contain one or more adjuvant substances, such as thickening agents, medicaments, or the like to improve the medical or veterinary utility for the particular application.

Suitable thickeners include, for example, polycyanoacrylates, polylactic acid, poly-1,4-dioxa-2-one, polyoxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, polymethyl methacrylate and copolymers of alkyl methacrylates, butadiene, and the like, and mixtures thereof. Examples of alkyl methacrylates and acrylates are poly(2-ethylhexyl methacrylate) and poly(2-ethylhexyl acrylate), also poly(butylmethacrylate) and poly(butylacrylate), also copolymers of various acrylate and methacrylate monomers, such as poly(butylmethacrylate-co-methylacrylate), and the like, and mixtures thereof. In an aspect, a thickener can include a partial polymer of cyanoacrylate as disclosed in U.S. patent application Ser. No. 12/214,791, and triblock copolymers of polyoxyalkylene as disclosed in U.S. patent application Ser. No. 12/214,794. In many applications, it is desirable that the thickening agent is miscible in cyanoacrylate monomer compositions at room temperature.

In an aspect, a biodegradable cyanoacrylate composition, with or without a thickening agent, has a viscosity such that the liquid composition stops flowing beyond the intended application site or is substantially prevented from dripping. For example, a composition disclosed herein may have a viscosity of less than 100 cP, less than 50 cP, less than 30 cP, less than 20 cP, less than 15 cP, or the viscosity in the range of from about 10 cps to about 20 cP, from about 10 cP to about 30 cP, or from about 20 cP to about 30 cP, from about 10 cP to about 40 cP, from about 20 cP to about 40 cP. Standards and devices are known for measuring viscosity, such a viscometer, and cone and plate. As the biodegradable cyanoacrylate composition is provided pre-mixed and sterile, the initial biodegradable cyanoacrylate composition may have a lower viscosity than does a biodegradable cyanoacrylate composition after sterilization or a biodegradable cyanoacrylate composition during its usable period and/or nearing the end of its shelf-life. For example, an initial mixed sterilized biodegradable cyanoacrylate composition may have a viscosity that is less than or equal to 19 cP, or less than or equal to 18 cP, or less than or equal to 17 cP, less than or equal to 16 cP, or less than or equal to 15 cP, whereas a mixed sterilized biodegradable cyanoacrylate composition after a time during its usable shelf-life may have a viscosity that is less than or equal to 30 cP, or less than or equal to 29 cP, or less than or equal to 28 cP, less than or equal to 27 cP, or less than or equal to 26 cP, less than or equal to 25 cP, less than or equal to 24 cP, less than or equal to 23 cP, less than or equal to 22 cP, less than or equal to 21 cP, less than or equal to 20 cP.

Many known cyanoacrylate compositions have components that must be kept separated until the moment of use. For example, many adhesives require that two components be mixed and then immediately used as polymerization occurs at the point of mixing and application of the composition must occur before the polymerization is rapidly completed. This requires provision of ampules or separate containers for the components, to prevent polymerization in the containers provided.

Unlike these cyanoacrylate compositions, biodegradable cyanoacrylate compositions disclosed herein are provided in a mixed state, such that the biodegradable cyanoacrylate composition is provided in one container wherein the cyanoacrylate component, along with the other components such as the stabilizing component and the polymerization inhibitor component, are provided in one container and no mixing to initiate polymerization needs to be performed by the user before providing the biodegradable cyanoacrylate composition to the target site. The cyanoacrylate component may comprise one or more cyanoacrylate monomers therein. This mixed condition of the disclosed compositions may also be referred to herein as "pre-mixed" in contrast to cyanoacrylate compositions that must be immediately mixed at time of use to initiate polymerization. As can be understood, should a user wish to add components to the biodegradable cyanoacrylate composition, such as sonolucent particles, the particles may be mixed into the biodegradable cyanoacrylate composition, but this mixing is not performed to initiate polymerization of the cyanoacrylate monomers.

In an aspect, biodegradable cyanoacrylate compositions disclosed herein may be provided in a liquid state by providing a composition in containers, such as the containers disclosed herein. As referred to herein, disclosed biodegradable cyanoacrylate compositions are formulated by, for example, admixing two cyanoacrylate monomers, and the composition remains liquid, in an unpolymerized state, during shipping and storage until use. The biodegradable cyanoacrylate composition remains in a liquid state until application to a moisture-containing environment, such as a body lumen or surface. The disclosed biodegradable cyanoacrylate compositions have an extended shelf-life, during which time the composition meets the criteria and standards for use. For example, a biodegradable cyanoacrylate composition disclosed herein may have a shelf life of 0.5 year or longer, of 0.6 year or longer, of 0.7 year or longer, of 0.8 year or longer, of 0.9 year or longer, of 1.0 year or longer, or 1.2 year or longer, or 1.5 year or longer. For example, a biodegradable cyanoacrylate composition disclosed herein may have a shelf life of 0.5 year, 0.7 year, 0.9 year, 1.0 year, 1.2 year, or 1.5 year. The biodegradable cyanoacrylate composition may adequately function for longer periods than healthcare regulations permit for the provision of the compositions. To improve cohesive strength of a formed biodegradable cyanoacrylate composition, crosslinking agents known in the art may be added. Reference is made to U.S. Pat. No. 3,940,362 which is hereby incorporated by reference herein.

For certain applications, a biodegradable cyanoacrylate composition may further contain small amounts of colorants such as dyes or pigments. Suitable dyes include derivatives of anthracene and other complex structures, specifically, without limitation, 1-hydroxy-4-[4-methylphenylamino]-9,10 anthracenedione (D&C violet No. 2); 9-(ocarboxyphenyl)-6-hydroxy-2,4,5,7-tetraiodo-3H-xanthen-3-one-, disodium salt, monohydrate (FD&C Red No. 3); disodium salt of 6-hydroxy-5-[(4-sulfophenyl)axo]-2-naphthalene-sulfonic acid (FD&C Yellow No. 6); 2-(1,3 dihydro-3-oxo-5-sulfo-2H-indole-2-ylidine)-2,3-dihydro-3oxo-1H-ind-ole-5 sulfonic acid disodium salt (FD&C Blue No. 2); and 1,4-bis(4-methylanilino)anthracene-9,10-dione (D&C Green No. 6). In an aspect, the dyes are D&C Violet No. 2, FD&C Blue No. 2, and D&C Green No. 6.

In an aspect, a biodegradable cyanoacrylate composition may comprise sonolucent or radiopaque compounds or particles so that the occlusion can be monitored by sonography, fluoroscopy, or x-ray techniques.

In an aspect, a biodegradable cyanoacrylate composition can further comprise additional stabilizing or preservative agents such as alkyl parabens and salts thereof, ethylparaben, methylparaben, methylparaben sodium, propylparaben sodium, propylparaben, butylparaben, and the like. Other suitable preservatives include hydroquinone, pyrocatechol, resorcinol, 4-n-hexyl resorcinol, benzoic acid, benzyl alcohol, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, cresols, phenylmercuric compounds such as phenylmercuric borate, and phenylmercuric nitrate.

In an aspect, a biodegradable cyanoacrylate composition can further comprise an antimicrobial agent in an effective amount. Suitable antimicrobial agents include antibacterial agents such as chlorhexidine and its salts, typical antibiotics, copolymers of vinylpyrrolidone and vinyl acetate, antiseptics, the iodine containing polymer such as povidone iodine, biguanidine compounds, phenol compounds such as 5-chloro-2-(2,4-dichlorophenoxy)phenol, acridine compounds, quaternary ammonium compounds such as benzalkonium chloride, cetylpridospores and zephiran, copolymers of vinylpyrrolidone and vinyl acetate cross-linked with polyisocyanates, heavy metal salts such as silver nitrate, and aldehyde compounds such as glutaraldehyde.

For certain applications, a biodegradable cyanoacrylate composition may additionally contain polymerization initiators or accelerators that are activated by heat, light, or other modification on delivery to the site of action. Such initiators and accelerators are known in the art. Reference is made to U.S. Pat. No. 6,143,805 which is hereby incorporated by reference herein. For example, polymerization accelerators may be selected from calixarenes and oxacalixarenes, silacrowns, crown ethers, cyclodextrin and its derivatives, polyethers, aliphatic alcohol, various aliphatic carboxylic acid esters, benzoyl peroxide, amine compounds such as are triethyl amine, diethyl amine, butyl amine, isopropyl amine, tributyl amine, N,N,-dimethyl aniline, N,N-diethyl aniline, N,N-dimethyl-p-toluidine, N,N-dimethyl-m-toluidine, N,Ndimethyl-o-toluidine, dimethyl benzyl amine, pyridine, picoline, vinyl pyridine, ethanolamine, propanolamine and ethylene diamine, quaternary ammonium salts such as alkyl ammonium salts, amide-bonded ammonium salts, ester-bonded ammonium salts, ether-bonded ammonium salts and alkylimidazolinium salts, cyclosulfur compounds and derivatives, and polyalkylene oxides and derivatives.

In an aspect, a crown ether as the accelerator may be included in a cyanoacrylate composition. Examples of crown ethers include, but are not limited to, 15-crown-5, 18-crown-6, dibenzo-18-crown-6, tribenzo-18-crown-6, dicyclohexyl-18-crown-6, benzo-15-crown5, dibenzo-24-crown-8, dibenzo-30-crown-10, asym-dibenzo-22-crown-6, dimethylsila-11 crown-4, dimethylsila-14-crown-5, dimethylsila-17-crown-6, dibenzo-14-crown-4, dicyclohexyl24-crown-8, asym-dibenzo-22-crown-6, cyclohexyl-12-crown-4,1,2-decalyl-15-crown-5,1,2-naphtho-15-crown-5,3,4,5-naphthyl-16-crown-5,1,2-methyl-benzo-18-crown-6,1,2-methylbenzo-5,6-methylbenzo-18-crown-6,1,2-t-butyl-18-crown-6,1,2-vinylbenzo-15-crown-5,1,2-vinylbenzo-18-crown-6,1,2-t-butyl-cyclohexyl-18-crown-6, and 1,2-benzo-1,4-benzo-5oxygen-20-crown-7.

In an aspect, the amount of polymerization accelerator that is added to a cyanoacrylate composition is in the amount of about 10 ppm-6000 ppm. For example, the polymerization accelerator can be present in the amount of about 40 ppm-5000 ppm, and more preferably about 60 ppm-4000 ppm of the liquid adhesive composition. The amount of polymerization accelerator to be used can be determined by one of ordinary skill in the art using known techniques without undue experimentation.

Though not wishing to be bound by any particular theory, it is believed that disclosed biodegradable cyanoacrylate compositions induce a cellular and/or tissue reaction in two layers of a conduit, for example, to both the epithelial layer and to the myosalpinx (muscular layer) of a body conduit, such as a fallopian tube. The cellular and/or tissue reaction induced by chemical and physical contact of the polymerized cyanoacrylate composition with these body layers may occur over a duration of weeks to several months. While it performs its function of a prolonged reaction to the tissues over time, the biodegradable cyanoacrylate composition gradually degrades. Though not wishing to be bound by any particular theory, it is thought that the degradation process begins at the interface of the solidified (polymerized) composition and the epithelial layer. Over time, chemical bonds of the polymerized composition at the epithelial layer will be continually exposed to moisture and secretions generated by the secretary cells of the mucosa. The exposure leads to a gradual breakdown and removal of the polymerized composition. Along with degradation and expulsion of the polymerized composition, the exposed and reacting muscle layers of the conduit, for example those on opposing sides of the conduit, come into direct contact with each other, and in healing, anneal together to form a lasting occlusion and close off the conduit. The polymerized cyanoacrylate forms the initial occlusion of the conduit, and though the cyanoacrylate composition degrades and leaves the conduit, the affected tissue forms the lasting occlusion.

Though not wishing to be bound by any particular theory, it is believed that a cyanoacrylate composition disclosed herein is primarily degraded by ester hydrolysis. For example, methoxypropyl cyanoacrylate was found by Shalaby and Shalaby (Chapter 5, Cyanoacrylate-based Systems as Tissue Adhesives. Absorbable and Biodegradable Plymers, 2004. CRC Press LLC) to be a more hydrophilic cyanoacrylate than cyanoacrylates that degrade by the chain scission degradation pathway. Methoxypropyl cyanoacrylates under hydrolysis of their ester group, produce water-soluble by-products, without formation of formaldehyde. Polymerization of methoxypropyl cyanoacrylate is based on hydrolysis of chain pendent ester groups and formation of water-soluble, excretable by-products. Some by-products are alcohols, with no detectable acetate production and/or very low levels of formaldehyde.

A biodegradable cyanoacrylate composition may be placed into and stored in a container, including, but not limited to containers made of plastic, aluminum or glass. Examples of containers include, but are not limited to, pouches, vials, applicators such as swabs or an applicator tip on a container holding a composition therein, ampoules, syringes, pipettes, and components of medical devices capable of delivering the cyanoacrylate composition.

In an aspect, a biodegradable cyanoacrylate composition comprises a cyanoacrylate component comprising a one cyanoacrylate compound or monomer or a blend or admixture of cyanoacrylate compounds or monomers, referred to herein as a cyanoacrylate or cyanoacrylates. For example, a cyanoacrylate component may comprise one cyanoacrylate or more than one cyanoacrylate in a blend or admixture of cyanoacrylates. A cyanoacrylate component of the present disclosure may comprise one or more cyanoacrylates that have long side groups, relatively slow polymerization and slow degradation, in comparison to methyl-2-cyanoacrylate, which has a short side group, fast polymerization and fast degradation, and in comparison to a blend of 2-octyl cyanoacrylate and butyl lactoyl cyanoacrylate, which has a long side group, slow polymerization and very slow degradation.

In an aspect, a biodegradable cyanoacrylate composition consists of a cyanoacrylate component consisting of 30 wt % (±5%) 2-butyoxyethyl cyanoacrylate and 70 wt % (±5%) pentyl cyanoacrylate, a stabilizing component consisting of lactone, in an amount from amount from about 500 ppm to about 700 ppm, and a polymerization inhibitor component consisting of dinitrophenol, in an amount from about 4000 ppm to 6000 ppm.

In an aspect, a biodegradable cyanoacrylate composition consists of a cyanoacrylate component consisting of 60 wt % (±5%) nonyl cyanoacrylate and 40 wt % (±5%) 2-octyl cyanoacrylate, a stabilizing component consisting of carbonic acid, in an amount from amount from about 400 ppm to about 800 ppm, and a polymerization inhibitor component consisting of hydroquinone, in an amount from about 4000 ppm to 6000 ppm.

In an aspect, a biodegradable cyanoacrylate composition consists of a cyanoacrylate component consisting of 50 wt % (±5%) n-butyl-2-cyanoacrylate and 50 wt % (±5%) septyl cyanoacrylate, a stabilizing component consisting of sulfur dioxide, in an amount from amount from about 400 ppm to about 800 ppm, and a polymerization inhibitor component consisting of butylated hydroxyanisole, in an amount from about 4000 ppm to 6000 ppm.

In an aspect, a biodegradable cyanoacrylate composition consists of a cyanoacrylate component consisting of 50 wt % (±5%) methoxy-n-propyl cyanoacrylate and 50 wt % (±5%) methoxy-iso-propyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 6000 ppm.

In an aspect, a biodegradable cyanoacrylate composition consists of a cyanoacrylate component consisting of 30 wt % (±5%) methoxy-n-propyl cyanoacrylate and 70 wt % (±5%) methoxy-iso-propyl cyanoacrylate, a stabilizing component consisting of sulfur dioxide, in an amount from amount from about 600 ppm to about 700 ppm, and a polymerization inhibitor component consisting of butylated hydroxyanisole, in an amount from about 5000 ppm to 6000 ppm.

In an aspect, a biodegradable cyanoacrylate composition consists of a cyanoacrylate component consisting of 70 wt % (±5%) methoxy-n-propyl cyanoacrylate and 30 wt % (±5%) methoxy-iso-propyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 6000 ppm.

In an aspect, a biodegradable cyanoacrylate composition consists of a cyanoacrylate component consisting of 40 wt % (±5%) 2-isopropoxethyl cyanoacrylate and 60 wt % (±5%) pentyl cyanoacrylate, a stabilizing component consisting of acetic acid, in an amount from amount from about 600 ppm to about 700 ppm, and a polymerization inhibitor component consisting of butylated hydroxyanisole, in an amount from about 5000 ppm to 7000 ppm.

In an aspect, a biodegradable cyanoacrylate composition comprises a cyanoacrylate component consisting of greater than 95 wt %, or greater than 99 wt %, of methoxypropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition comprises a cyanoacrylate component comprising greater than 95 wt %, or greater than 99 wt %, of methoxypropyl cyanoacrylate, a stabilizing component comprising sulfur dioxide, in an amount from amount from about 500 ppm to about 700 ppm, and a polymerization inhibitor component comprising butylated hydroxyanisole, in an amount from about 4000 ppm to 7000 ppm.

In an aspect, a biodegradable cyanoacrylate composition consists of a cyanoacrylate component consisting of greater than 95 wt %, or greater than 99 wt %, of methoxypropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition comprises a cyanoacrylate component consisting of greater than 95 wt %, or greater than 99 wt %, of methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition comprises a cyanoacrylate component comprises greater than 95 wt %, or greater than 99 wt %, of methoxyisopropyl cyanoacrylate, a stabilizing component consisting of sulfur dioxide, in an amount from amount from about 500 ppm to about 700 ppm, and a polymerization inhibitor component consisting of butylated hydroxyanisole (BHA), in an amount from about 4000 ppm to 7000 ppm.

In an aspect, a biodegradable cyanoacrylate composition consists of a cyanoacrylate component consisting of greater than 95 wt %, or greater than 99 wt %, of methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition consists of a cyanoacrylate component consisting of 70 wt % (±5%) methoxypropyl cyanoacrylate and 30 wt % (±5%) methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition comprises a cyanoacrylate component comprising at least 70 wt % (±5%) methoxypropyl cyanoacrylate and at least 30 wt % (±5%) methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition consists of a cyanoacrylate component consisting of 30 wt % (±5%) methoxypropyl cyanoacrylate and 70 wt % (±5%) methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition comprises a cyanoacrylate component comprising at least 30 wt % (±5%) methoxypropyl cyanoacrylate and at least 70 wt % (±5%) methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition consists of a cyanoacrylate component consisting of 50 wt % (±5%) methoxypropyl cyanoacrylate and 50 wt % (±5%) methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition comprises a cyanoacrylate component comprising at least 50 wt % (±5%) methoxypropyl cyanoacrylate and at least 50 wt % (±5%) methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition consists of a cyanoacrylate component consisting of 60 wt % (±5%) 2-isopropoxethyl cyanoacrylate and 40 wt % (±5%) pentyl cyanoacrylate, a stabilizing component consisting of acetic acid, in an amount from amount from about 600 ppm to about 700 ppm, and a polymerization inhibitor component consisting of catechol, in an amount from about 5000 ppm to 7000 ppm.

In an aspect, a biodegradable cyanoacrylate composition consists of a cyanoacrylate component consisting of 50 wt % (±5%) 2-isopropoxethyl cyanoacrylate and 50 wt % (±5%) pentyl cyanoacrylate, a stabilizing component consisting of acetic acid, in an amount from amount from about 600 ppm to about 700 ppm, and a polymerization inhibitor component consisting of catechol, in an amount from about 5000 ppm to 7000 ppm.

A biodegradable cyanoacrylate composition disclosed herein can be defined by functional characteristics. A biodegradable cyanoacrylate composition suitable for methods of conduit occlusion in human and animals comprises a composition that passes on or all biocompatibility characterizing tests, for example, as measured by ISO standards, and fails cytotoxicity testing, for example, as measured by ISO 10993-5:2009.

Biodegradable cyanoacrylate compositions of the present disclosure comprise a cyanoacrylate component, a stabilizing component and a polymerization inhibitor component and passes two or more biocompatibility tests for sensitization (for example, as measured by ISO 10993-10:2010), irritation (for example, as measured by ISO 10993-10:2010), vaginal irritation (for example, as measured by ISO 10993-10:2010), pyrogenicity (for example, as measured by ISO 10993-11:2010), systemic acute toxicity (for example, as measured by ISO 10993-11:2010), systemic sub-chronic toxicity (for example, as measured by ISO 10993-11:2010), genotoxicity (for example, as measured by ISO 10993-3:2003), rodent blood micronucleus assay (for example, as measured by ISO 10993-3:2003), and mouse lymphoma mutagenesis (for example, as measured by ISO 10993-3:2003), and fails cytotoxicity testing (for example, as measured by ISO 10993-5:2009). Compositions used for human or animal treatments must pass these listed biocompatibility tests to be considered safe for use, thus in an aspect, a disclosed biodegradable cyanoacrylate composition must pass each of these tests (sensitization, irritation, vaginal irritation, pyrogenicity, systemic acute toxicity, systemic sub-chronic toxicity, genotoxicity, rodent blood micronucleus assay, and mouse lymphoma mutagenesis, and fail the cytotoxicity test.

A composition disclosed herein, for example, for conduit occlusion, comprises a cyanoacrylate component, a stabilizer component and a polymerization inhibitor component and fails cytotoxicity testing, for example, as measured by ISO 10993-5:2009, and passes biocompatibility testing for genotoxicity, for example, as measured by ISO 10993-3:2003. A composition for conduit occlusion comprises a cyanoacrylate component, a stabilizer component and a polymerization inhibitor component and fails cytotoxicity testing, for example, as measured by ISO 10993-5:2009, and passes at least biocompatibility testing for genotoxicity, for example, as measured by ISO 10993-3:2003.

In an aspect, a biodegradable cyanoacrylate composition disclosed herein has a low heat of polymerization, for example, compared to a known cyanoacrylate composition, Histoacryl. Histoacryl, available from commercial suppliers such as Aesculap AG, Am AESCULAP-Platz, D-78532 Tuttlingen/Donau, AT, is a cyanoacrylate composition comprising butyl cyanoacrylate. In an example, using a pig skin pouch to simulate a body conduit, the increase in temperature (herein the heat of polymerization) found after administration of the biodegradable cyanoacrylate composition to the pig skin was less than 1° C. (i.e., at approximately 0.7°

C.), whereas the increase in temperature (herein the heat of polymerization) of Histoacryl was 6.7° C. In an aspect, a composition disclosed herein, for example, for conduit occlusion, comprises a cyanoacrylate component, a stabilizer component and a polymerization inhibitor component and has a low heat of polymerization temperature of less than 6° C., of less than 5° C., of less than 4° C., of less than 3° C., of less than 2° C., of less than 1° C., or in a range from about 0.5° C. to about 6° C., and all ranges therein between. In an aspect, a biodegradable cyanoacrylate composition disclosed herein, for example, for conduit occlusion, comprises a cyanoacrylate component, a stabilizer component and a polymerization inhibitor component and has a low heat of polymerization temperature in a range of from 0.5° C. to 1.0° C. Heat of polymerization may be measured by differential scanning calorimetry, for example, based on ASTM D3418-12e1.

In an aspect, a biodegradable cyanoacrylate composition disclosed herein, for example, for conduit occlusion, comprises a cyanoacrylate component, a stabilizer component and a polymerization inhibitor component, that has a rapid in vitro cure time or setting time but does not release deleterious heat. Cure time or setting time refers to the rate of polymerization of at least a portion of the composition. For example, biodegradable cyanoacrylate compositions disclosed herein were tested in pig fallopian tubes and a complete curing of the administered biodegradeable cyanoacrylate composition was seen at 2 minutes. In an aspect, a biodegradable cyanoacrylate composition disclosed herein has a cure time of at least a portion of the administered composition of greater than or equal to 10 seconds, of greater than or equal to 15 seconds, of greater than or equal to 20 seconds, of greater than or equal to 30 seconds, of greater than or equal to 40 seconds, of greater than or equal to 50 seconds, of greater than or equal to 60 seconds, of greater than or equal to 70 seconds, of greater than or equal to 80 seconds, of greater than or equal to 90 seconds, of greater than or equal to 100 seconds, of greater than or equal to 110 seconds, or of greater than or equal to 120 seconds. In an aspect, biodegradable cyanoacrylate composition disclosed herein has a cure time of 2 minutes or less, of less than 110 seconds, of less than 100 seconds, of less than 90 seconds, of less than 80 seconds, of less than 70 seconds, of less than 60 seconds, of less than 50 seconds, of less than 40 seconds, of less than 30 seconds, of less than 25 seconds, of less than 20 seconds, of less than 15 seconds, or of less than 10 seconds. In an aspect, a biodegradable cyanoacrylate composition disclosed herein has a cure time (or setting time) of between 10 seconds and 120 seconds.

In an aspect, a biodegradable cyanoacrylate composition disclosed herein is pliable when polymerized. Pliability may be assessed by a free-bend test, wherein a composition is polymerized into a rod and the rod is bent 180°. The extent of damage or change is documented by fracture, surface condition and cracking of the rod. In an experiment, a polymerized rod of a disclosed biodegradable cyanoacrylate composition was compared to a polymerized rod of Histoacryl Blue (butyl cyanoacrylate), the disclosed biodegradable cyanoacrylate composition bent 180 degrees without damage or significant change whereas the Histoacryl Blue rod broke in pieces before reaching 180 degrees of bending. In an aspect, a biodegradable cyanoacrylate composition disclosed herein is pliable, as measured by this test, after polymerization.

In an aspect, a biodegradable cyanoacrylate composition disclosed herein, for example, for conduit occlusion, comprises a cyanoacrylate component, a stabilizer component and a polymerization inhibitor component, that passes at least a biocompatibility test for genotoxicity, fails a biocompatibility test for cytotoxicity, has a low heat of polymerization temperature in a range of from 0.5° C. to 1.0° C., has a viscosity of less than or equal to 30 cP, a cure or setting time between 10 seconds and 30 seconds, is pliable, and a shelf-life of greater than 0.5 year, and optionally, the composition may be sterilized.

Biodegradable cyanoacrylate compositions of the present disclosure are suitable for use in medical and veterinary applications. Biodegradable cyanoacrylate compositions for such applications are preferably sterile. Thus, the present disclosure comprises sterile biodegradable cyanoacrylate compositions as described herein. Biodegradable cyanoacrylate compositions disclosed herein may be sterilized by common techniques. Sterilization of the cyanoacryolate adhesive compositions is accomplished by methods including, but not limited to, chemical, physical, and irradiation methods. Examples of chemical methods include, but are not limited to, exposure to ethylene oxide. Examples of irradiation methods include, but are not limited to, gamma irradiation, electron beam irradiation, and microwave irradiation. Preferred methods of sterilization are chemical sterilization and electron beam sterilization. For example, a suitable container containing a disclosed biodegradable cyanoacrylate composition may be sterilized by 10-20 kGy does electron beam processing. Such sterilization methods are known in the art, and for example, taught by ISO 11137-2. In general, methods of the present disclosure comprise providing and/or administering or applying biodegradable cyanoacrylate compositions, comprising at least a cyanoacrylate component, a stabilizer component and a polymerization inhibitor component, to site on or in a body, for example, in or near a conduit for occluding a conduit. In an aspect, disclosed herein are exemplary compositions for occlusion of conduits, for example, of the reproductive tracts of mammals. Such compositions can be used in other physiological systems and biological sites of humans or other animals, whether such sites are naturally there or have been created, for example, by surgical means, and such uses are contemplated by the present disclosure.

One aspect of the present disclosure comprises methods of contraception for mammalian females that administer a biodegradable cyanoacrylate composition to a target site, for example, from the cornual aspect of the uterus into each fallopian tube, wherein the biodegradable cyanoacrylate composition is capable of creating an occlusion in each fallopian tube.

For example, in an aspect a method comprises delivering, using a catheter or delivery system comprising one or more catheters, into the uterine cavity cornua, and directed to the fallopian tubes, a liquid biodegradable cyanoacrylate composition. An effective amount of a biodegradable cyanoacrylate composition disclosed herein is delivered, and may comprise from about 0.3 to 1.0 mL of liquid cyanoacrylate composition, or 0.3, 0.4, 0.5, 0.6, 0.7, 0.8, 0.9, 1.0 mL may be delivered. Larger or smaller amounts may be delivered, but the method is not contemplated to fill the entire fallopian tube, but to deliver minimally, for example, to the interstitial (intramural) portion of the tube and to form an occlusion in the proximal portion of the fallopian tube. The biodegradable cyanoacrylate composition polymerizes (solidifies) upon contact with the tissue and fluids in the uterine cavity and fallopian tube(s). It is believed that the biodegradable cyanoacrylate composition adheres primarily to the epithelial lining of the corneal region and luminal circumference due to chemical bonding and physical contact of the polymerized cyanoacrylate composition. The biodegradable cyanoacrylate composition occupies spaces within the undulating structure of the epithelium.

It is believed that the biodegradable cyanoacrylate composition is substantially confined to the target areas during and after the polymerization process. This may be due, in part, to delivering the cyanoacrylate composition in a controlled, (e.g., slow) manner and in a discrete volume. One of skill in the art would understand how to deliver a polymerizable composition.

It is believed that a disclosed biodegradable cyanoacrylate composition induces cellular and/or tissue inflammatory-type reactions in both the epithelial lining and to the myosalpinx (muscular layer) of the fallopian tube. The cellular and/or tissue reaction is induced by chemical and physical contact with the tubal lining circumference and may last for several weeks. Prolonged cellular and/or tissue reaction prevents typical regeneration healing actions that could occur for shorter durations of cell injury, especially in the myosalpinx which regenerates more slowly than the endosalpinx. Without typical fibrinolysis that repairs short term inflammation, the reacting tissues will not heal with functional tissue, and instead, formation of nonfunctional scar tissue takes place. While the polymerized biodegradable cyanoacrylate composition is providing a prolonged reaction to the tissues over several weeks, the biodegradable cyanoacrylate composition is gradually degrading. It is thought that with time, the surface bonds of the polymerized biodegradable cyanoacrylate composition will be continually exposed to moisture and secretions generated by secretory cells of the mucous membrane. This exposure leads to a gradual breakdown and removal of the biodegradable cyanoacrylate composition. Once the biodegradable cyanoacrylate composition is removed from an area of the fallopian tube, occlusion occurs by luminal obliteration and scarring. It is expected that as the polymerized biodegradable cyanoacrylate composition degrades, the degradation products and/or solid pieces of the polymerized material which break off, will travel in the direction of the uterine cavity by the tubal fluid and by the pro-uterine ciliary beat, and then out the vagina.

In order to provide for successful occlusion of a fallopian tube with a biodegradable cyanoacrylate composition delivered through intrauterine catheters non-surgically, the following is desirable:

a biodegradable cyanoacrylate composition that remains in liquid form when stored pre- and post-sterilization and during delivery, therefore, a biodegradable cyanoacrylate composition may be formulated to be stable and not undergo premature polymerization;

biodegradable cyanoacrylate composition may be of suitable viscosity to travel through and be delivered by intrauterine catheters directed at or into the target site, such as a fallopian tube(s);

once delivered to the target site, such as a fallopian tube(s), a biodegradable cyanoacrylate composition may polymerize quickly, e.g., within a few seconds, to prevent movement from the target site, e.g., fallopian tubes;

the resulting cured polymer (polymerized biodegradable cyanoacrylate composition material) may elicit a localized reaction, while the polymer begins to degrade, breakdown, and/or break apart;

the resulting cured polymer (polymerized biodegradable cyanoacrylate material) may lack durability, shedding from the conduit over time allowing for a durable occlusion due to the conduit's response to the cyanoacrylate composition and its healing reaction; and a biodegradable cyanoacrylate composition is administered and the resulting cured composition is non-toxic and biocompatible for the subject to whom the occluding composition is provided, but may be deleterious to other cells such as sperm.

The biodegradable cyanoacrylate compositions may also be naturally sonolucent or may be modified to have enhanced sonolucency by the introduction of materials or bubbles such as microbubbles of air or gas. These microbubbles may be present within the composition or may be present when the composition polymerizes into a solid form.

A method disclosed herein comprises administering a biodegradable cyanoacrylate composition at or near the site for occlusion and allowing the cyanoacrylate composition to polymerize in situ in the site. A method may further comprise viewing the occluding site. A method may further comprise testing that occlusion of the site has occurred.

It must be noted that, as used herein and the appended claims, the singular forms "a", "an", and "the" include plural referents unless the context clearly dictates otherwise.

All patents, patent applications and references included herein are specifically incorporated by reference in their entireties.

It should be understood, of course, that the foregoing relates only to exemplary embodiments of the present disclosure and that numerous modifications or alterations may be made therein without departing from the spirit and the scope of the invention as set forth in this disclosure.

Although the exemplary embodiments of the present invention describe in detail methods, delivery systems, and compositions to occlude the fallopian tubes of human, the present invention is not limited to these embodiments. There are numerous modifications or alterations that may suggest themselves to those skilled in the art for use of the methods, delivery systems, and compositions herein for the occlusion of a variety of conduits in both human and non-human mammals.

PCT/US2018/017484 is herein incorporated in its entirety.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, when a compound is referred to as a monomer or a compound, it is understood that this is not interpreted as one molecule or one compound. For example, two cyanoacrylate monomers refers to two different cyanoacrylate monomers, and not two molecules.

As used herein, the terms "optional" or "optionally" means that the subsequently described event or circumstance can or cannot occur, and that the description includes instances where said event or circumstance occurs and instances where it does not.

As used herein, the terms "about," "approximate," and "at or about" mean that the amount or value in question can be the exact value designated or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, "cure" means a change in the physical, chemical, or physical and chemical properties of the cyanoacrylate material following placement or insertion at the desired site in a conduit, and as is generally understood for polymeric materials, "cure" means the composition transforms from a liquid to a solid or semi-solid.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In an aspect, a mammalian subject is a human. A patient refers to a subject afflicted with a disease or disorder. The term "patient" includes human and veterinary subjects. In some aspects of the disclosed methods, the subject has been diagnosed with a need for a treatment comprising occluding a conduit prior to the administering of the cyanoacrylate compositions. In some aspects, the subject has been diagnosed with a need for administration of the cyanoacrylate compositions prior to the administering step.

As used herein, the terms "administering" and "administration" refer to any method of providing a disclosed cyanoacrylate composition to a subject.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

The transitional phrase "consisting of" excludes any element, step, or ingredient not specified in the claim, closing the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole.

The transitional phrase "consisting essentially of" limits the scope of a claim to the specified materials or steps and those that do not materially affect the basic and novel characteristic(s) of the claimed invention. A 'consisting essentially of' claim occupies a middle ground between closed claims that are written in a 'consisting of' format and fully open claims that are drafted in a 'comprising' format. Optional additives as defined herein, at a level that is appropriate for such additives, and minor impurities are not excluded from a composition by the term "consisting essentially of".

When a composition, a process, a structure, or a portion of a composition, a process, or a structure, is described herein using an open-ended term such as "comprising," unless otherwise stated the description also includes an embodiment that "consists essentially of" or "consists of" the elements of the composition, the process, the structure, or the portion of the composition, the process, or the structure.

The articles "a" and "an" may be employed in connection with various elements and components of compositions, processes or structures described herein. This is merely for convenience and to give a general sense of the compositions, processes or structures. Such a description includes "one or at least one" of the elements or components. Moreover, as used herein, the singular articles also include a description of a plurality of elements or components, unless it is apparent from a specific context that the plural is excluded.

The term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such.

The term "or", as used herein, is inclusive; that is, the phrase "A or B" means "A, B, or both A and B". More specifically, a condition "A or B" is satisfied by any one of the following: A is true (or present) and B is false (or not present); A is false (or not present) and B is true (or present); or both A and B are true (or present). Exclusive "or" is designated herein by terms such as "either A or B" and "one of A or B", for example. As used herein, paired elements, such as material containers 103a and 103b may be referred to as material containers 103a/b, where it is meant both 103a and 103b. In some figures, a side view is shown and only one of the pair, such as 103a, is shown. It is understood that 103b, not shown, would have similar position or actions.

In the figures, it is intended for like numbers to be used throughout the figures. For example, an element marked 112 in FIG. 1 would be referred to as 212 in FIG. 2, 312 in FIG. 3 and so on.

In addition, the ranges set forth herein include their endpoints unless expressly stated otherwise. Further, when an amount, concentration, or other value or parameter is given as a range, one or more preferred ranges or a list of upper preferable values and lower preferable values, this is to be understood as specifically disclosing all ranges formed from any pair of any upper range limit or preferred value and any lower range limit or preferred value, regardless of whether such pairs are separately disclosed. The scope of the invention is not limited to the specific values recited when defining a range.

When materials, methods, or machinery are described herein with the term "known to those of skill in the art", "conventional" or a synonymous word or phrase, the term signifies that materials, methods, and machinery that are conventional at the time of filing the present application are encompassed by this description. Also encompassed are materials, methods, and machinery that are not presently conventional, but that will have become recognized in the art as suitable for a similar purpose.

Unless stated otherwise, all percentages, parts, ratios, and like amounts, are defined by weight.

What is claimed is:

1. A method for occluding at least one fallopian tube in a human or animal body, comprising,
   a) providing to the uterus of a human or animal a controlled delivery device capable of delivering an effective amount of a composition comprising an occlusive material, wherein the delivery device comprises at least an insertion tube for providing at least one catheter; at least one catheter comprising an end structure on a delivery end that maintains the delivery end in at least one uterine cornua and aids in localized delivery of the composition; a handle comprising a level, a receptacle for receiving a material cartridge and a slider for moving a catheter slide, wherein the catheter slide moves the at least one catheter in a proximal or distal direction; a system plunger controlled by a lock, wherein the lock is movable between position one and position two; wherein the system plunger is reversibly coupled to a control rod, the control rod defining two sets of parallel connecting elements, one set comprising attachment elements for moving two air syringes, and a second set comprising positioning elements, for moving material plunger actuators; wherein the lock is movable between a first position and a second position, and, when the lock is in the first position, the system plunger and the control rod are coupled such that movement of the system plunger moves the control rod, and when the lock is in the second position, the system plunger and the control rod are uncoupled such that the system plunger can move independently of the control rod and a material cartridge containing the composition comprising an occlusive material positioned within the receptacle in the handle;
   b) delivering an effective amount of the composition comprising an occlusive material through and out the at least one catheter at or near the uterine cornua such that the occlusive material occludes the lumen of the fallopian comprising the following steps:
      i) with the system plunger rigidly coupled with the control rod and the lock in the lock position one, inserting the material cartridge containing the occlusive material within the receptacle in the handle;
      ii) moving the slider from a proximal position to a distal position so that the catheter slide moves the at least one catheter so that the at least one catheter delivery end exits the insertion tube and is positioned in the uterine cornua;
      iii) distally moving the rigidly coupled system plunger and control rod so that air is moved to fill the end structure of at least one catheter;
      iv) moving the lock to the lock position two which uncouples the system plunger from the control rod so that when system plunger moves, the control rod is stationary;
      v) moving the system plunger further distally, while the control rod remains stationary, so that the occlusive material is moved from the material cartridge through and out the delivery end of at least one catheter and into at least the uterine cornua;
      vi) returning the lock to the lock position one to rigidly reengage the system plunger and the control rod;
      vii) moving the rigidly engaged system plunger and control rod in a proximal direction which deflates the end structure of at least one catheter; and
      viii) withdrawing the insertion tube from the human or animal body.

2. The method of claim 1, wherein two fallopian tubes are occluded without removal and re-introduction or substantial repositioning of the controlled delivery device.

3. The method of claim 1, wherein the composition comprising an occlusive material comprises a biodegradable cyanoacrylate composition.

4. The method of claim 3, wherein the composition, when cured, swells less than 20%.

5. The method of claim 3, wherein the composition is about 20% to about 100% substantially resorbed in a range of about 30 to about 365 days.

6. The method of claim 1, wherein the occlusion is maintained by tissue ingrowth.

7. The method of claim 1, wherein the composition further comprises tissue scarring agents, fibrosis agents, fertilization inhibitors, contraceptive agents, tissue growth promoters, hormones, polymerization inhibitors, polymerization stabilizers, emulsifying agents, echogenic agents, contrast agents, viscosity-modifying materials, plasticizers, colorants or combinations thereof.

8. The method of claim 1, wherein the composition further comprises a curable carrier for the occlusive materials, a control release agent, tissue scarring agents, fibrosis agents, fertilization inhibitors, contraceptive agents, tissue growth promoters, hormones, polymerization inhibitors, polymerization stabilizers, emulsifying agents, echogenic agents, contrast agents, viscosity-modifying materials, plasticizers, colorants or combinations thereof.

9. A method for contraception, comprising,
   a) providing to the uterus of a human or animal a controlled delivery device capable of delivering an effective amount of a composition comprising an occlusive material, wherein the delivery device comprises at least an insertion tube for providing at least one catheter; at least one catheter comprising an end structure on a delivery end that maintains the delivery end in at least one uterine cornua and aids in localized delivery of the composition; a handle comprising a level, a receptacle for receiving a material cartridge and a slider for moving a catheter slide, wherein the catheter slide moves the at least one catheter in a proximal or distal direction; a system plunger controlled by a lock, wherein the lock is movable between position one and position two; wherein the system plunger is reversibly coupled to a control rod, the control rod defining two sets of parallel connecting elements, one set comprising attachment elements for moving two air syringes, and a second set comprising positioning elements, for moving material plunger actuators; wherein the lock is movable between a first position and a second position, and, when the lock is in the first position, the system plunger and the control rod are coupled such that movement of the system plunger moves the control rod, and when the lock is in the second position, the system plunger and the control rod are uncoupled such that the system plunger can move independently of the control rod and a material cartridge containing the composition comprising an occlusive material positioned within the receptacle in the handle;
   b) delivering an effective amount of the composition comprising an occlusive material through and out the at least one catheter at or near the uterine cornua such that the occlusive material occludes the lumen of the fallopian comprising the following steps:
i) with the system plunger rigidly coupled with the control rod and the lock in the lock position one, inserting the material cartridge containing the occlusive material within the receptacle in the handle;
ii) moving the slider from a proximal position to a distal position so that the catheter slide moves the at least one catheter so that the at least one catheter delivery end exits the insertion tube and is positioned in the uterine cornua;
iii) distally moving the rigidly coupled system plunger and control rod so that air is moved to fill the end structure of at least one catheter;
iv) moving the lock to the lock position two which uncouples the system plunger from the control rod so that when system plunger moves, the control rod is stationary;
v) moving the system plunger further distally, while the control rod remains stationary, so that the occlusive material is moved from the material cartridge through and out the delivery end of at least one catheter and into at least the uterine cornua;
vi) returning the lock to the lock position one to rigidly reengage the system plunger and the control rod;
vii) moving the rigidly engaged system plunger and control rod in a proximal direction which deflates the end structure of at least one catheter; and
viii) withdrawing the insertion tube from the human or animal body.

\* \* \* \* \*

UNITED STATES PATENT AND TRADEMARK OFFICE
CERTIFICATE OF CORRECTION

| | | |
|---|---|---|
| PATENT NO. | : 11,744,729 B2 | Page 1 of 1 |
| APPLICATION NO. | : 16/402193 | |
| DATED | : September 5, 2023 | |
| INVENTOR(S) | : Kathy Lee-Sepsick and Jeremy Sipos | |

It is certified that error appears in the above-identified patent and that said Letters Patent is hereby corrected as shown below:

On the Title Page

Item (12) should read "Lee-Sepsick et al."

Item (72) add "Jeremy Sipos, Suwanee, GA"

Signed and Sealed this
First Day of October, 2024

Katherine Kelly Vidal
*Director of the United States Patent and Trademark Office*